US008541385B2

(12) United States Patent
Stoffel et al.

(10) Patent No.: US 8,541,385 B2
(45) Date of Patent: Sep. 24, 2013

(54) CHEMICALLY MODIFIED OLIGONUCLEOTIDES FOR USE IN MODULATION MICRO RNA AND USES THEREOF

(75) Inventors: Markus Stoffel, Zurich (CH); Muthiah Manoharan, Weston, MA (US); Kallanthottathil G Rajeev, Wayland, MA (US)

(73) Assignees: The Rockefeller University, New York, NY (US); Alnylam Pharmaceuticals, Inc., Cambridge, MA (US)

( * ) Notice: Subject to any disclaimer, the term of this patent is extended or adjusted under 35 U.S.C. 154(b) by 344 days.

(21) Appl. No.: 12/714,863

(22) Filed: Mar. 1, 2010

(65) Prior Publication Data

US 2010/0222413 A1 Sep. 2, 2010

Related U.S. Application Data

(63) Continuation of application No. 11/657,341, filed on Jan. 24, 2007, now abandoned, which is a continuation-in-part of application No. 11/502,158, filed on Aug. 10, 2006.

(60) Provisional application No. 60/706,866, filed on Aug. 10, 2005, provisional application No. 60/731,554, filed on Oct. 28, 2005, provisional application No. 60/763,201, filed on Jan. 26, 2006.

(51) Int. Cl.
*A61K 48/00* (2006.01)

(52) U.S. Cl.
USPC ......... 514/44; 536/24.5; 536/24.31; 536/24.1

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. | |
| 5,256,775 A | 10/1993 | Froehler | |
| 5,595,760 A | 1/1997 | Cherif-Cheikh | |
| 5,672,659 A | 9/1997 | Shalaby | |
| 5,902,880 A | 5/1999 | Thompson | |
| 6,107,094 A | 8/2000 | Crooke | |
| 6,146,886 A | 11/2000 | Thompson | |
| 6,395,713 B1 | 5/2002 | Beigelman et al. | |
| 6,727,064 B2 | 4/2004 | Karras | |
| 7,232,806 B2 | 6/2007 | Tuschl | |
| 2004/0266707 A1 | 12/2004 | Leake et al. | |
| 2005/0261218 A1* | 11/2005 | Esau et al. | 514/44 |
| 2007/0049547 A1* | 3/2007 | Esau et al. | 514/44 |

FOREIGN PATENT DOCUMENTS

| | | |
|---|---|---|
| WO | WO 93/23569 | 11/1993 |
| WO | WO 94/02595 | 2/1994 |
| WO | WO 96/10390 | 4/1996 |
| WO | WO 96/10391 | 4/1996 |
| WO | WO 96/10392 | 4/1996 |
| WO | WO 00/53722 | 9/2000 |
| WO | WO 01/36646 | 5/2001 |
| WO | WO2005/013901 | 2/2005 |
| WO | 2005/107816 | 11/2005 |

OTHER PUBLICATIONS

Olie et al. Analysis of ribosyl-modified, mixed backbone analogs of bcl-2/bcl-xL antisense oligonucleotide. Biochimica et Biophysica Acta 1576 (2002) pp. 101-109.*
Akhtar et al., "Cellular Uptake and Intracellular Fate of Antisense Oligonucleotides," *Trends in Cell Biology*, vol. 2, pp. 139-144, 1992.
Aldrian-Herrada et al., "A Peptide Nucleic Acid (PNA) is More Rapidly Internalized in Cultured Neurons When Coupled to a Retro-Inverso Delivery Peptide. The Antisense Activity Depresses the Target mRNA and Protein in Magnocellular Oxytocin Neurons," *Nucleic Acids Research*, vol. 26, pp. 4910-4916, 1998.
Ambros, "The Functions of Animal MicroRNAs," *Nature*, vol. 431, pp. 350-355, 2004.
Boado et al., "Drug Delivery of Antisense Molecules to the Brian for Treatment of Alzheimer's Disease and Cerbral AIDS," *Journal of Pharmaceutical Sciences*, vol. 87, pp. 1308-1315, 1998.
Boado, "Brain-Derived Peptides Regulate the Steady State Levels and Increase Stability of the Blood-Brain Barrier GLUT1 Glucose Transporter mRNA," *Neuroscoence Letters*, vol. 197, pp. 179-182, Sep. 15, 1995.
Boado, *Adv. Drug Delivery Rev.* 15:73-107, 1995.
Bottoni et al., "miR-15a and miR-16-1 down-regulation in pituitary adenomas," 2005, *J. Cellular Physiology* 204:280-85.
Brummelkamp et al., "Stable Suppression of Tumorigenicity by Virus-Mediated RNA Interference," *Cancer Cell*, vol. 2, pp. 243-247, 2002.
Caplen et al., "RNAi as a gene therapy approach." 2003, *Expert Opin. Biol. Ther.* 3(4):575-86.
Castillo-Davis et al, "GeneMerge-Post-Genetic Analysis, Data Mining, and Hypothesis Testing," *Bioinformatics*, vol. 19, pp. 891-892, 2003.
Chang J. et al., "miR-122, a Mammalian Liver-Specific MicroRNA is Processed from *hcr* mRNA and May Downregulate the High Affinity Cationic Amino Acid Transporter CAT-1," *RNA Biology* vol. 1, pp. 106-113, 2004.
Chen et al., "Multitarget Ribozyme Directed to Cleave at up to Nine Highly Conserved HIV-1 Env RNA Regions Inhibits HIV-1 Replication—potential Effectiveness Against Most Presently Sequenced HIV-1 Isolates," *Nucleic Acids Research*, vol. 20, pp. 4581-4589, 1992.
Cheruvallath et al ,"Use of phenylacetyl disulfide (PADS) in the synthesis of oligodeoxyribonucleotide phosphorothioates," *Nucleosides Nucleotides* 18:485-492, 1999.
Chowrira et al., "In Vitro and In Vivo comparison of Hammerhead, Hairpin, and Hepatitis Delta Virus Self-Processing Ribozyme Cassettes," Journal of Biol. Chem., vol. 269, pp. 25856-25864, 1994.
Colledge et al., "Disruption of C-mos Causes Parthenogenetic Development of Unfertilized Mouse Eggs," Nature, vol. 370, pp. 65-68, 1994.

(Continued)

*Primary Examiner* — Kimberly Chong
(74) *Attorney, Agent, or Firm* — Casimir Jones, S.C.

(57) ABSTRACT

This invention relates generally to chemically modified oligonuceotides useful for modulating expression of microRNAs and pre-microRNAs. More particularly, the invention relates to single stranded chemically modified oligonuceotides for inhibiting microRNA and pre-microRNA expression and to methods of making and using the modified oligonucleotides. Also included in the invention are compositions and methods for silencing microRNAs in the central nervous system.

12 Claims, 25 Drawing Sheets

(56) References Cited

OTHER PUBLICATIONS

Couture et al., "Anti-Gene Therapy: The Use of Ribozymes to Inhibit Gene Function," Trends in Genetics, vol. 12, pp. 510-515, 1996.
Crooke, et al., "Metabolism of Antisense Oligonucleotides in Rat Liver Homogenates," J Pharmacol Exp Ther. vol. 292, pp. 140-149, 2000.
Damha et al, Oligoribonucleotide Synthesis> The Silyl-Phosphoramidite Method, Methods Mol. Biol., vol. 20, pp. 81-114, 1993.
Davis, et al., "Improved Targeting of miRNA With Antisense Oligonucleotides," Nucleic Acids Research, vol. 34, pp. 2294-2304, 2006.
Dropulic et al., "Functional Characterization of a U5 Ribozyme: Intracellular Suppression of Human Immunodeficiency Virus Type 1 Expression," Journal of Virology, vol. 66, pp. 1432-1441, 1992.
Elbashir et al., "RNA Interference is Mediated by 21- and 22-Nucleotide RNAs," Genes and Dev., vol. 15, pp. 188-200, 2001.
Esquela-Kerscher, et al., "Oncomirs—MicroRNAs With a Role in Cancer," Nat Rev Cancer, vol. 6, pp. 259-269, 2006.
Gonzalez et al., "New Class of Polymers for the Delivery of Macromolecular Therapeutics," Bioconjugate Chem., vol. 10, pp. 1068-1074, 1999.
Good et al., "Expression of Small, Therapeutic RNAs in Human Cell Nuclei," Gene Therapy, vol. 4, pp. 45-54, 1997.
Griffiths-Jones, "The MicroRNA Registry," Nucleic Acids Research, vol. 32, D109-D111, 2004.
Grunweller, et al., "Cellular Uptake and Localization of a Cy3-Labeled siRNA Specific for the Serine/Threonine Kinase Pim-1," Oligonucleotides, vol. 13, pp. 345-352, 2003.
Hashimoto et al. "Partheogenetic Activation of Oocytes in C-Mos-Deficient Mice," Nature, vol. 370, pp. 68-71, 1994.
Hubbard et al., "Ensembl 2005," Nucleic Acids Res., vol. 33, Database issue: D447-D453, 2005.
Ishiwata et al., "Physical-Chemistry Characteristics and Blodistribution of Poly(ethylene Glycol)-Coated Liposomes Using Poly(Oxyethylene) Cholesteryl," Chemical and Pharmaceutical Bulletin (Tokyo), vol. 43, pp. 1005-1011, 1995.
Izant et al., "Constitutive and Conditional Suppression of Exogenous and Endogenous Genes by Anti-Sense RNA," Science, vol. 229, pp. 345-352, 1985.
John et al., "Human MicroRNA Targets," PLoS Biology, vol. 2, pp. 1862-1878, 2004; correction in PLoS Biology 3:1328, 2005.
Jolliet-Riant et al., "Drug Transfer Across the Blood-Brain Barrier and Improvement of Brain Delivery," Fundamental and Clinical Pharmacology, vol. 13, pp. 16-26, 1999.
Jopling, et al., "Modulation of Hepatitis C Virus RNA Abundance by a Liver-Specific MicroRNA," Science, vol. 309, pp. 1577-1581, 2005.
Kashani-Sabet et al., "Reversal of the Malignant Phenotype by an Anti-ras Ribozume," Antisense Res. Dev., vol. 2, pp. 3-15, 1992.
Kloosterman, et al., "Targeted Inhibition of miRNA Maturation with Morpholinos Reveals a Role for Mir-375 in Pancreatic Islet Development" PLos Biology, Aug. 2007, vol. 5, pp. 1738-1749.
Kloosterman, et al., "The Diverse Functions of MicroRNAs in Animal Development and Disease," Developmental Cell, vol. 11, pp. 441-450, 2006.
Krek et al., "Combinatorial MicroRNA Target Predictions," Nature Genetics, vol. 37, pp. 495-500, 2005.
Krutzfeldt, et al., "MicroRNAs: A New Class of Regulatory Genes Affecting Metabolism," Cell Metabolism, vol. 4, pp. 9-12, 2006.
Krutzfeldt, et al., "Silencing of MicroRNAs In Vivo with Antagomirs," Nature, vol. 438, pp. 685-689, 2005.
Krutzfeldt, et al., "Strategies to Determine the Biological Function of MicroRNAs," Nature Genetics, vol. 38, pp. S14-S19, 2006.
Lasic et al., "Liposomes Revisited," Science, vol. 267, pp. 1275-1276, 1995.
Lasic et al., "The 'Stealth' Liposome: A Prototypical Biomaterial," Chemical Reviews, vol. 95, pp. 2601-2628, 1995.
Lee et al., ACS Symp. Ser. 752:184-192, 2000.
Lewis et al., "Conserved Seed Pairing, Often Flanked by Adenosines, Indicates that Thousands of Human Genes are MicroRNA Targets," Cell, vol. 120, pp. 15-20, 2005.
Lim et al., "Microarray Analysis Shows that Some MicroRNAs Downregulate Large Numbers of Target mRNAs," Nature, vol. 433, pp. 769-773, 2005.
Limbach et al., "Summary: The Modified Nucleosides of RNA," Nucleic Acids Research, vol. 22, pp. 2183-2196, 1994.
Lingor, et al., "Down-Regulation of Apoptosis Mediators by RNAi Inhibits Axotomy-Induced Retinal Ganglion Cell Death In Vivo," Brain, vol. 128, pp. 550-558, 2005.
Liu et al., "Cationic Liposome-Mediated Intravenous Gene Delivery," Journal of Biological Chemistry, vol. 42, pp. 24864-24870, 1995.
Matranga, et al., "Passenger-Strand Cleavage Facilitates Assembly of siRNA into Ago2-Containing RNAi Enzyme Complexes," Cell, vol. 123, pp. 607-620, 2005.
Maurer et al., "Lipid-Based Systems for the Intracellular Delivery of Genetic Drugs," Mol. Membr. Biol., vol. 16, pp. 129-140, 1999.
McGarry et al, "Inhibition of Heat Shock Protein Synthesis by Heat-Inducible Antisense RNA," Proc. Natl. Acad. Sci. USA, vol. 83, pp. 399-403, 1986.
Nguyen, et al., "A Molecular Defect in Hepatic Cholesterol Biosynthesis in Sitosterolemia with Xanthomatosis," J. Clin. Invest., vol. 86, pp. 923-931, 1990.
Ohkawa et al., "Activities of HIV-RNA Targeted Ribozymes Transcribed from a 'Shot-Gun' Type Ribozyme-Trimming Plasmid," Nucleic Acids Symp. Ser. vol. 27, pp. 15-16, 1992.
Ojwang et al., "Inhibition of Human Immunodeficiency Virus Type 1 Expression by a Hairpin Ribozyme," Proc. Natl. Acad. Sci. USA, vol. 89, pp. 10802-10806, 1992.
Oku et al., "Real-Time Analysis of Liposomal Trafficking in Tumor-Bearing Mice by use of Positron Emission Tomography," Biochim. Biophys. Acta, vol. 1238, pp. 86-90, 1995.
Oli, et al., "Analysis of ribosyl-modified, mixed backbone analogs of bcl-2/bcl-xl antisense oligonucleotide" 2002 Biochim Biophys Acta 1576:101-109.
Pardridge et al., "Vector-Mediated Delivery of a Polyamide ("Peptide") Nucleic Acid Analogue Through the Blood-Brain Barrier In Vivo," PNAS USA, vol. 92, pp. 5592-5596, 1995.
Paroo et al, "Challenges for RNAi in vivo." 2004, Trends in Biotechnology 22(8):390-4.
Pruitt, et al., "NCBI Reference Sequence (RefSeq): A Curated Non-Redundant Sequence Database of Genomes, Transcripts and Proteins," Nucleic Aids Research, vol. 33, pp. D501-D504, 2005.
Rand, et al., "Argonaute2 Cleaves the Anti-Guide Strand of siRNA During RISC Activation," Cell, vol. 123, pp. 621-629, 2005.
Sarver et al., "Ribozymes as Potential Anti-HIV-1 Therapeutic Agents," Science, vol. 247, pp. 1222-1225, 1990.
Scanlon et al., "Ribozyme-Mediated Cleavage of C-Fos mRNA Reduces Gene Expression of DNA Synthesis Enzymes and Metallothionein," Proc. Natl. Acad. Sci. USA, vol. 88, pp. 10591-10595, 1991.
Shih, et al., "Profound Defects in Pancreatic Beta-Cell Function in Mice with Combined Heterozygous Mutations in Pdx-1, Nnf-1 Alpha, and Hnf-3beta," Proc. Natl. Acad. Sci., USA, vol. 99, pp. 3818-3823, 2002.
Soutschek, et al., "Therapeutic Silencing of an Endogenous Gene by Systemic Administration of Modified siRNAs," Nature, vol. 432, pp. 173-178, 2004.
Stankov et al., "Antisense antiviral agents: about the optimal approach," 2000, Medical Hypothesis 54(3):501-2.
Taira et al., "Construction of a Novel RNA-Transcript-Trimming Plasmid Which can be Used Both In Vitro in Place of Run-Off and (G)-Free Transcriptions and In Vivo as Multi-Sequences Transcription Vectors," Nucleic Acids Research, vol. 19, pp. 5125-5130, 1991.
Thompson et al., "Improved Accumulation and Activity of Ribozymes Expressed from a tRNA-Based RNA Polymerase III Promoter," Nucleic Acids Res., vol. 23, pp. 2259-2268, 1995.
Tyler et al., "Peptide Nucleic Acids Targeted to the Neurotensin Receptor and Administered i.p. Cross the Blood-Brain Barrier and Specifically Reduce Gene Expression," PNAS USA, vol. 96, pp. 7053-7058, 1999.

Tyler et al., "Specific Gene Blockage Shows that Peptide Nucleic Acids Readily Enter Neuronal Cells In Vivo," *FEBS Lett.*, vol. 421, pp. 280-284, 1999.

Ventura et al., "Activation of HIV-Specific Ribozyme Activity by Self-Cleavage," *Nucleic Acids Res.*, vol. 21, pp. 3249-3255, 1993.

Weerasinghe et al., "Resistance to Human Immunodeficiency Virus Type 1 (HIV-1) Infection in Human CD4+ Lymphocyte-Derived Cell Lines Conferred by Using Retroviral Vectors Expressing an HIV-1 RNA-Specific Ribozyme," *Journal of Virology*, vol. 65, pp. 5531-5534, 1991.

* cited by examiner

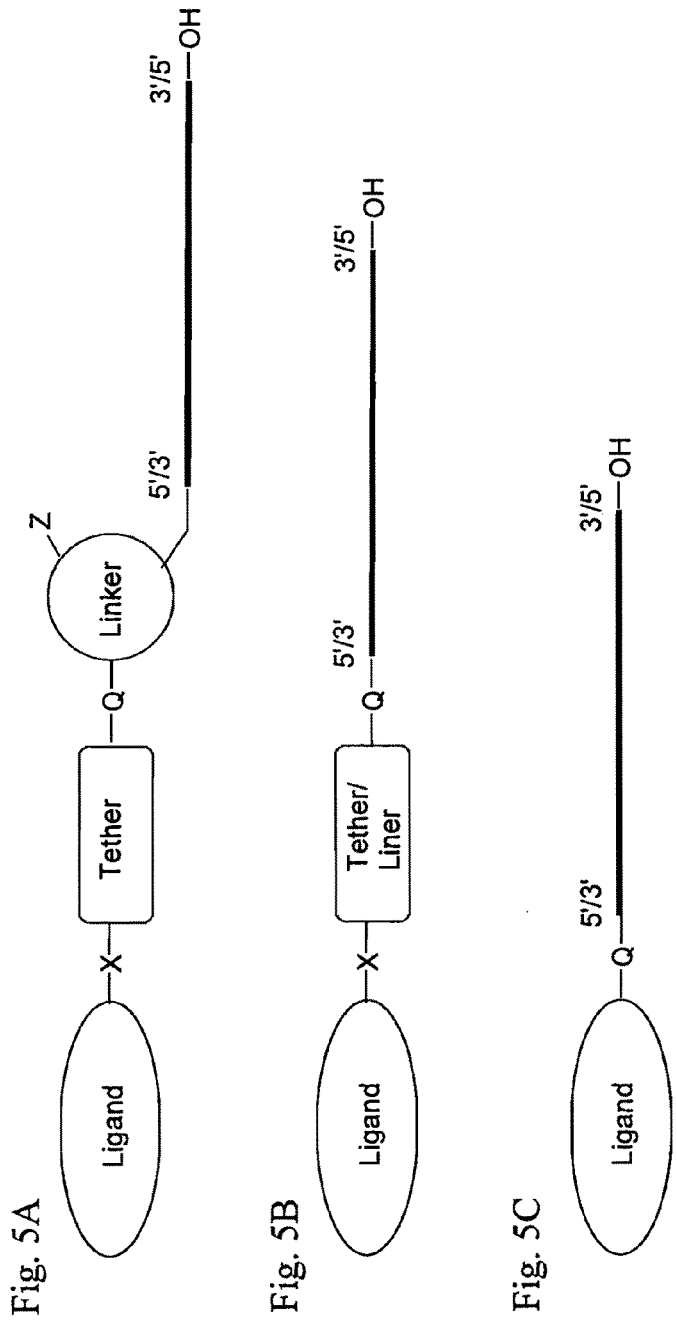

X = O, NH, NMe, S, S-S, SO, SO₂, CH₂, CONH, HNCO, CONMe, MeNCO, COO, OCO
Y = O, NH, NMe, S, S-S, SO, SO₂, CH₂, CONH, HNCO, CONMe, MeNCO, COO, OCO
Z = OH, O-P(O)(O₂)-O-RNA, O-P(O)(S)-O-RNA, NH₂, COOH, CONH₂, Ligand
Q = -O-P(O)₂O-, -O-P(O)(S)O-, -NH-P(O)₂NH-, -OP(O)₂NH-, -NH-P(O)(S)O-, -O-P(O)(S)NH-O, NH, NMe, S, S-S, SO, SO₂, CH₂, CONH, HNCO, CONMe, MeNCO, COO, OCO
-O-P(O)NHR-O-, -O-P(O)(R)-O-

X = O, NH, NMe, S, S-S, SO, SO$_2$, CH$_2$, CONH, HNCO, CONMe, MeNCO, COO, OCO
Y = O, NH, NMe, S, S-S, SO, SO$_2$, CH$_2$, CONH, HNCO, CONMe, MeNCO, COO, OCO
Z = OH, O-P(O$_2$)-O-RNA, O-P(O)(S)-O-RNA, NH$_2$, COOH, CONH$_2$, Ligand
Q = -O-P(O)$_2$O-, -O-P(O)(S)O-, -NH-P(O)$_2$O-, -OP(O)$_2$NH-, -NH-P(O)(S)O-, -O-P(O)(S)NH-
    O, NH, NMe, S, S-S, SO, SO$_2$, CH$_2$, CONH, HNCO, CONMe, MeNCO, COO, OCO
    -O-P(O)NHR-O-, -O-P(O)(R)-O-

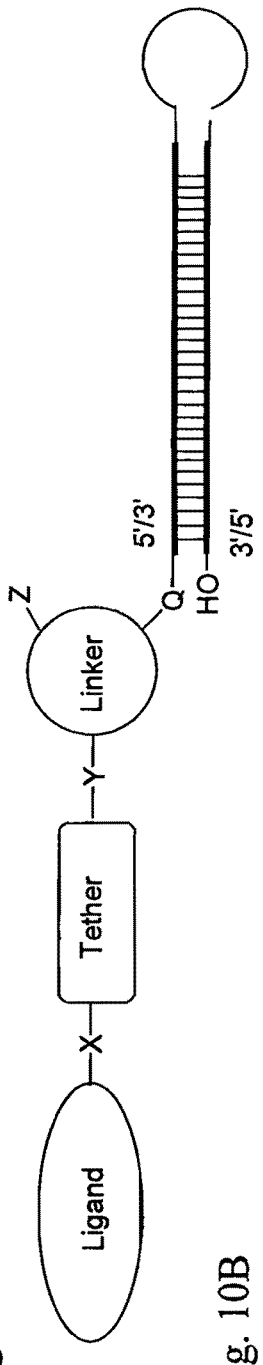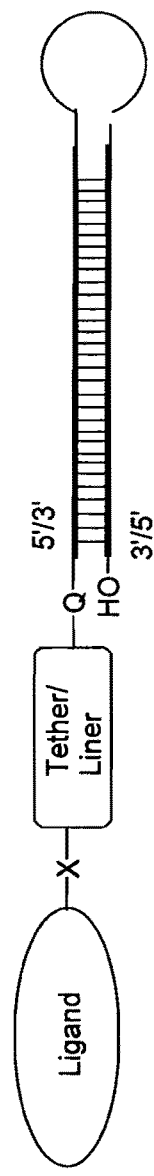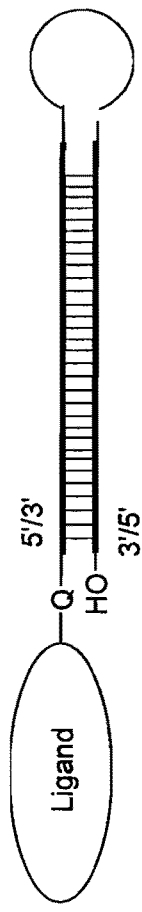
Fig. 10A
Fig. 10B
Fig. 10C
X = O, NH, NMe, S, S-S, SO, SO$_2$, CH$_2$, CONH, HNCO, CONMe, MeNCO, COO, OCO
Y = O, NH, NMe, S, S-S, SO, SO$_2$, CH$_2$, CONH, HNCO, CONMe, MeNCO, COO, OCO
Z = OH, O-P(O$_2$)-O-RNA, O-P(O)(S)-O-RNA, NH$_2$, COOH, CONH$_2$, Ligand
Q = -O-P(O)$_2$O-, -O-P(O)(S)O-, -NH-P(O)(O)$_2$O-, -OP(O)$_2$NH-, -NH-P(O)(S)O-, -O-P(O)(S)NH-, O, NH, NMe, S, S-S, SO, SO$_2$, CH$_2$, CONH, HNCO, CONMe, MeNCO, COO, OCO -O-P(O)NHR-O-, -O-P(O)(R)-O-

(a)
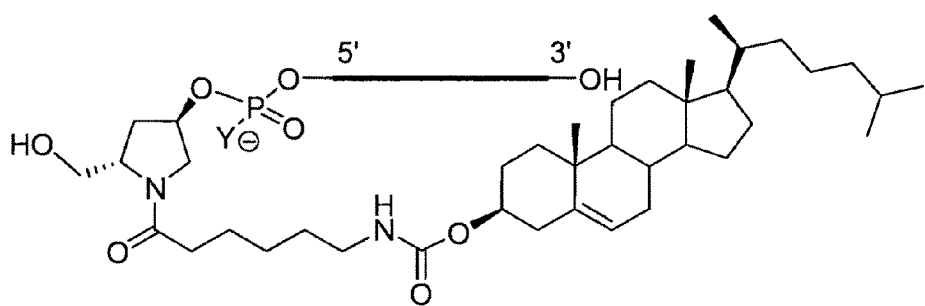
(b)
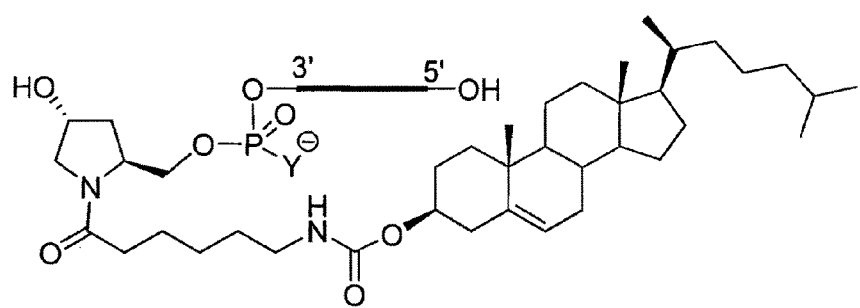
(c)
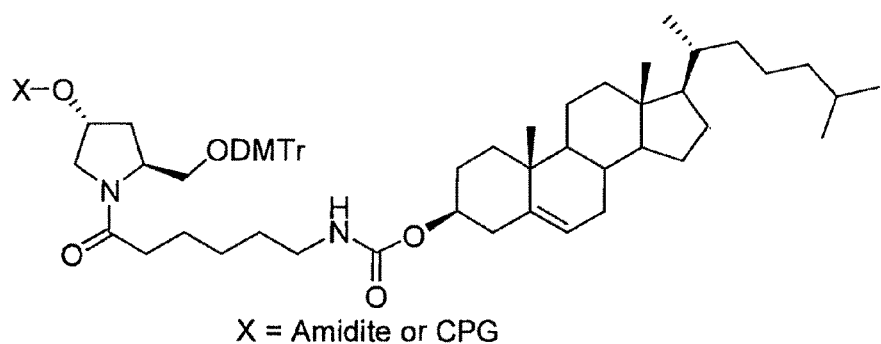
X = Amidite or CPG
Fig. 11

Fig. 17
A.
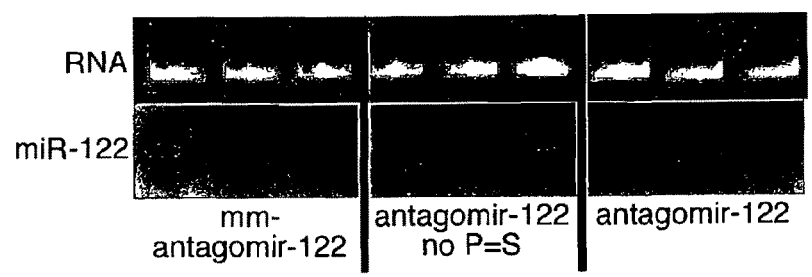
B.
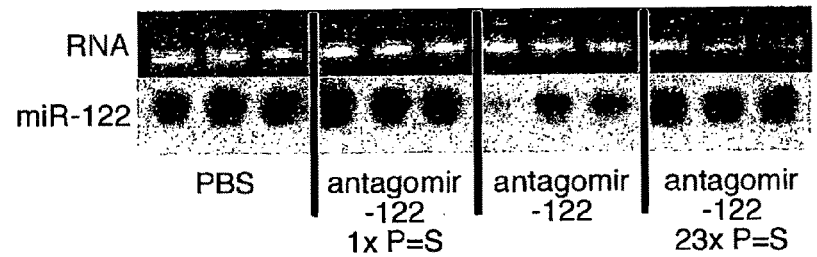
C.
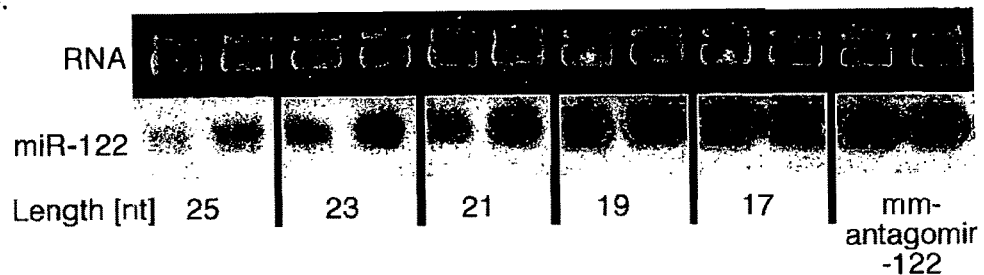

Fig. 20
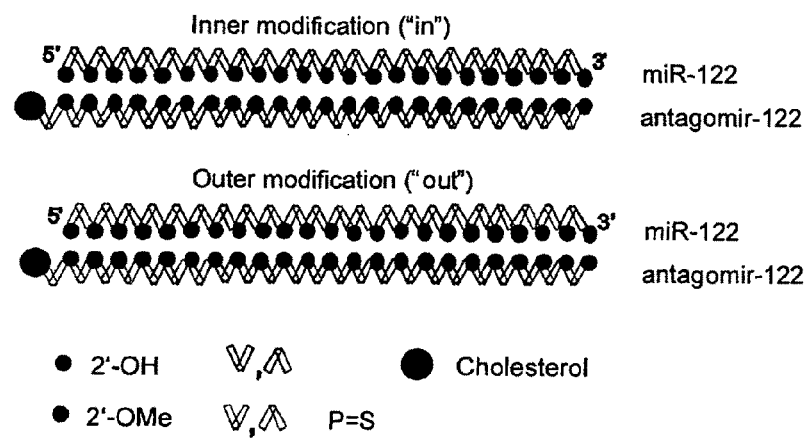
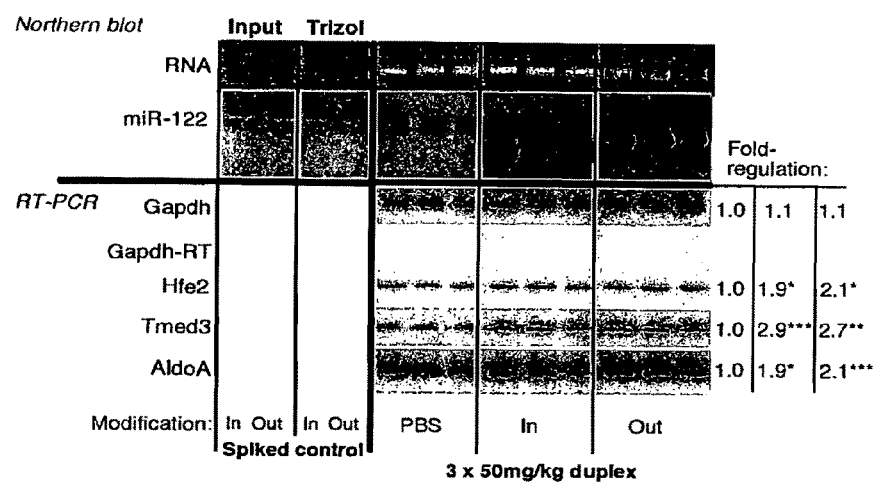

| | mm-antagomir-122 | | antagomir-122 | | n=5 | |
|---|---|---|---|---|---|---|
| | mean | SEM | mean | SEM | p-value | |
| age (weeks) | 7.7 | 0 | 7.7 | 0 | 1.000 | |
| bodyweight (g) | 16.3 | 0.3 | 16.2 | 0.3 | 0.792 | |
| glucose (mg%) | 138 | 7 | 152 | 13 | 0.429 | |
| FFA (mM) | 0.42 | 0.06 | 0.37 | 0.07 | 0.586 | |
| bile acids (μM) | 10.9 | 3.2 | 12.2 | 4.2 | 0.822 | |
| triglycerides (mg%) | 31.9 | 5.3 | 29.7 | 4.4 | 0.754 | |
| cholesterol (mg%) | 39.7 | 3.3 | 22.1 | 1.9 | 0.003 | (-44%) |
| ALT (U/l) | 23 | 7 | 26 | 4 | 0.734 | |

Fig. 25

SEQUENCE LISTING

```
<160> NUMBER OF SEQ ID NOS: 51

<210> SEQ ID NO 1
<211> LENGTH: 23
<212> TYPE: RNA
<213> ORGANISM: Mus musculus

<400> SEQUENCE: 1
uggaguguga caauguguu ugu                                            23

<210> SEQ ID NO 2
<211> LENGTH: 22
<212> TYPE: RNA
<213> ORGANISM: Mus musculus

<400> SEQUENCE: 2
uagcagcacg uaaauauugg cg                                            22

<210> SEQ ID NO 3
<211> LENGTH: 21
<212> TYPE: RNA
<213> ORGANISM: Mus musculus

<400> SEQUENCE: 3
cugaccuaug aauugacagc c                                             21

<210> SEQ ID NO 4
<211> LENGTH: 22
<212> TYPE: RNA
<213> ORGANISM: Mus musculus

<400> SEQUENCE: 4
uguaacagca acuccaugug ga                                            22

<210> SEQ ID NO 5
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
```

```
<221> NAME/KEY: modified_base
<222> LOCATION: 1, 2,  20, 21, 22, 23
<223> OTHER INFORMATION: /2'-O-methyl modification phosphorothioate
      linkage corresponding base
<220> FEATURE:
<221> NAME/KEY: modified_base
<222> LOCATION: (3)...(19)
<223> OTHER INFORMATION: 2'-O-methyl modified nucleotides corresponding
      base

<400> SEQUENCE: 5
acaaacacca uugucacacu cca                                              23

<210> SEQ ID NO 6
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 19, 20, 21, 22
<223> OTHER INFORMATION: ' 2'-O-methyl modification phosphorothioate
      linkage corresponding base
<220> FEATURE:
<221> NAME/KEY: modified_base
<222> LOCATION: (3)...(18)
<223> OTHER INFORMATION: 2'-O-methyl modified nucleotides corresponding
      base

<400> SEQUENCE: 6
cgccaauauu uacgugcugc ua                                               22

<210> SEQ ID NO 7
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 18, 19, 20, 21
<223> OTHER INFORMATION: 2'-O-methyl modification phosphorothioate
      linkage coresponding base
<220> FEATURE:
<221> NAME/KEY: modified_base
<222> LOCATION: (3)...(17)
<223> OTHER INFORMATION: 2'-O-methyl modified nucleotides corresponding
      base

<400> SEQUENCE: 7
ggcugucaau ucauagguca g                                                21

<210> SEQ ID NO 8
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2,  19, 20, 21, 22
<223> OTHER INFORMATION: 2'-O-methyl modification phosphorothioate
      linkage corresponding base
<220> FEATURE:
<221> NAME/KEY: modified_base
<222> LOCATION: (3)...(18)
<223> OTHER INFORMATION: 2'-O-methyl modified nucleotides corresponding
      base

<400> SEQUENCE: 8
uccacaugga guugcuguua ca                                               22
```

```
<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
ccccttaaat agttgtttat tggca                                              25

<210> SEQ ID NO 10
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)...(23)
<223> OTHER INFORMATION: 2'-O-Me ribo sugar modification
      phosphorothioate linkage corresponding base

<400> SEQUENCE: 10
acaaacacca uugucacacu cca                                                23

<210> SEQ ID NO 11
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 20, 21, 22, 23
<223> OTHER INFORMATION: 2'-O-Me ribo sugar modification
      phosphorothioate linkage corresponding base
<220> FEATURE:
<221> NAME/KEY: modified_base
<222> LOCATION: (3)...(19)
<223> OTHER INFORMATION: 2'-O-Me ribo sugar modification corresponding
      base

<400> SEQUENCE: 11
acaaacacca uugucacacu cca                                                23

<210> SEQ ID NO 12
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 12
uggaauguga caguuugug ugu                                                 23

<210> SEQ ID NO 13
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)...(23)
<223> OTHER INFORMATION: 2'-O-Me ribo sugar modification
      phosphorothioate linkage corresponding base

<400> SEQUENCE: 13
acacacaaca cugucacauu cca                                                23
```

```
<210> SEQ ID NO 14
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 20, 21, 22, 23
<223> OTHER INFORMATION: 2'-O-Me ribo sugar modification
      phosphorothioate linkage corresponding base
<220> FEATURE:
<221> NAME/KEY: modified_base
<222> LOCATION: (3)...(19)
<223> OTHER INFORMATION: 2'-O-Me ribo sugar modification corresponding
      base

<400> SEQUENCE: 14
acacacaaca cugucacauu cca                                              23

<210> SEQ ID NO 15
<211> LENGTH: 31
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)...(23)
<223> OTHER INFORMATION: 2'-O-Me ribo sugar modification corresponding
      base
<220> FEATURE:
<221> NAME/KEY: modified_base
<222> LOCATION: 24, 25, 26, 27
<223> OTHER INFORMATION: deoxyribo sugar modification
<220> FEATURE:
<221> NAME/KEY: modified_base
<222> LOCATION: 28, 29, 30
<223> OTHER INFORMATION: 2'-O-Me ribo sugar modification corresponding
      base
<220> FEATURE:
<221> NAME/KEY: modified_base
<222> LOCATION: 31
<223> OTHER INFORMATION: 2'-O-Me ribo sugar modification
      phosphorothioate linkage

<400> SEQUENCE: 15
acaaacacca uugucacacu ccattttugg a                                     31

<210> SEQ ID NO 16
<211> LENGTH: 31
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)...(22)
<223> OTHER INFORMATION: 2'-O-Me ribo sugar modification corresponding
      base
<220> FEATURE:
<221> NAME/KEY: modified_base
<222> LOCATION: 23, 31
<223> OTHER INFORMATION: 2'-O-Me ribo sugar modification
      phosphorothioate linkage  corresponding base
<220> FEATURE:
<221> NAME/KEY: modified_base
<222> LOCATION: 24, 25, 26, 27
<223> OTHER INFORMATION: deoxyribo sugar modification phosphorothioate
      linkage
<220> FEATURE:
<221> NAME/KEY: modified_base
<222> LOCATION: 28, 29, 30
<223> OTHER INFORMATION: 2'-O-Me ribo sugar modification corresponding
      base
```

-continued

<400> SEQUENCE: 16
acaaacacca uugucacacu ccattttugg a                                    31

<210> SEQ ID NO 17
<211> LENGTH: 7
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)...(7)
<223> OTHER INFORMATION: 2'-O-Me ribo sugar modification corresponding
      base

<400> SEQUENCE: 17 uggagug                                                                7

<210> SEQ ID NO 18
<211> LENGTH: 7
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)...(7)
<223> OTHER INFORMATION: 2'-O-Me ribo sugar modification corresponding
      base

<400> SEQUENCE: 18 gacaaug                                                                7

<210> SEQ ID NO 19
<211> LENGTH: 7
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)...(7)
<223> OTHER INFORMATION: 2'-O-Me ribo sugar modification corresponding
      base

<400> SEQUENCE: 19 uggaaug                                                                7

<210> SEQ ID NO 20
<211> LENGTH: 7
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)...(7)
<223> OTHER INFORMATION: 2'-O-Me ribo sugar modification corresponding
      base

<400> SEQUENCE: 20 gacagug                                                                7

<210> SEQ ID NO 21
<211> LENGTH: 23
<212> TYPE: RNA
<213> ORGANISM: Artificial Sequence
<220> FEATURE:
<223> OTHER INFORMATION: Synthetically generated oligonucleotide

```
<220> FEATURE:
<221> NAME/KEY: modified_base
<222> LOCATION: 1, 2, 19, 20, 21, 22
<223> OTHER INFORMATION: 2'-O-Me ribo sugar modification
      phosphorothioate linkage corresponding base
<220> FEATURE:
<221> NAME/KEY: modified_base
<222> LOCATION: (3)...(18)
<223> OTHER INFORMATION: 2'-O-Me ribo sugar modification corresponding
      base
<220> FEATURE:
<221> NAME/KEY: modified_base
<222> LOCATION: 23
<223> OTHER INFORMATION: 2'-O-Me ribo sugar modification corresponding
      base

<400> SEQUENCE: 21
uggaguguga caaugguguu ugu                                            23

<210> SEQ ID NO 22
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 19, 20, 21, 22
<223> OTHER INFORMATION: 2'-O-Me ribo sugar modification
      phosphorothioate linkage corresponding base
<220> FEATURE:
<221> NAME/KEY: modified_base
<222> LOCATION: (3)...(18)
<223> OTHER INFORMATION: 2'-O-Me ribo sugar modification corresponding
      base
<220> FEATURE:
<221> NAME/KEY: modified_base
<222> LOCATION: 23
<223> OTHER INFORMATION: 2'-O-Me ribo sugar modification corresponding
      base

<400> SEQUENCE: 22
uggaauguga caguguugug ugu                                            23

<210> SEQ ID NO 23
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)..(22)
<223> OTHER INFORMATION: 2'-O-Me ribo sugar modification
      phosphorothioate linkage corresponding base
<220> FEATURE:
<221> NAME/KEY: modified_base
<222> LOCATION: 23
<223> OTHER INFORMATION: 2'-O-Me ribo sugar modification corresponding
      base

<400> SEQUENCE: 23
acaaacacca uugucacacu cca                                            23

<210> SEQ ID NO 24
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 19, 20, 21, 22
<223> OTHER INFORMATION: 2'-O-Me ribo sugar modification
```

```
        phosphorothioate linkage corresponding base
<220> FEATURE:
<221> NAME/KEY: modified_base
<222> LOCATION: (3)...(18)
<223> OTHER INFORMATION: 2'-O-Me ribo sugar modification corresponding
        base
<220> FEATURE:
<221> NAME/KEY: modified_base
<222> LOCATION: 23
<223> OTHER INFORMATION: 2'-O-Me ribo sugar modification corresponding
        base

<400> SEQUENCE: 24
acaaacacca uugucacacu cca                                                23

<210> SEQ ID NO 25
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 19, 20, 21, 22
<223> OTHER INFORMATION: 2'-O-Me ribo sugar modification
        phosphorothioate linkage corresponding base
<220> FEATURE:
<221> NAME/KEY: modified_base
<222> LOCATION: (3)...(18)
<223> OTHER INFORMATION: 2'-O-Me ribo sugar modification corresponding
        base

<400> SEQUENCE: 25
cgccaauauu uacgugcugc ua                                                 22

<210> SEQ ID NO 26
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 18, 20, 21
<223> OTHER INFORMATION: 2'-O-Me ribo sugar modification
        phosphorothioate linkage corresponding base
<220> FEATURE:
<221> NAME/KEY: modified_base
<222> LOCATION: (3)...(17
<223> OTHER INFORMATION: 2'-O-Me ribo sugar modification corresponding
        base

<400> SEQUENCE: 26
ggcugucaau ucauagguca g                                                  21

<210> SEQ ID NO 27
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 19, 20, 21, 22
<223> OTHER INFORMATION: 2'-O-Me ribo sugar modification
        phosphorothioate linkage corresponding base
<220> FEATURE:
<221> NAME/KEY: modified_base
<222> LOCATION: (3)...(18)
<223> OTHER INFORMATION: 2'-O-Me ribo sugar modification corresponding
        base

<400> SEQUENCE: 27
```

```
uccacaugga guugcuguua ca                                           22

<210> SEQ ID NO 28
<211> LENGTH: 22
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 19, 20, 21, 22
<223> OTHER INFORMATION: 2'-O-Me ribo sugar modification
      phosphorothioate linkage corresponding base
<220> FEATURE:
<221> NAME/KEY: modified_base
<222> LOCATION: (3)...(18)
<223> OTHER INFORMATION: 2'-O-Me ribo sugar modification corresponding
      base

<400> SEQUENCE: 28
ucacgcgagc cgaacgaaca aa                                           22

<210> SEQ ID NO 29
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 10, 12, 13
<223> OTHER INFORMATION: n = inosine

<400> SEQUENCE: 29
uggngugugn cnnugguguu ugu                                          23

<210> SEQ ID NO 30
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)..(23)
<223> OTHER INFORMATION: 2'-O-Me ribo sugar modification corresponding
      base

<400> SEQUENCE: 30
acaaacacca uugucacacu cca                                          23

<210> SEQ ID NO 31
<211> LENGTH: 25
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 22, 23, 24, 25
<223> OTHER INFORMATION: 2'-O-Me ribo sugar modification
      phosphorothioate linkage  corresponding base
<220> FEATURE:
<221> NAME/KEY: modified_base
<222> LOCATION: (3)...(21
<223> OTHER INFORMATION: 2'-O-Me ribo sugar modification corresponding
      base

<400> SEQUENCE: 31
cacaaacacc auugucacac uccac                                        25
```

-continued

```
<210> SEQ ID NO 32
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 18, 19, 20, 21
<223> OTHER INFORMATION: 2'-O-Me ribo sugar modification
      phosphorothioate linkage corresponding base
<220> FEATURE:
<221> NAME/KEY: modified_base
<222> LOCATION: (3)...(17
<223> OTHER INFORMATION: 2'-O-Me ribo sugar modification corresponding
      base

<400> SEQUENCE: 32
caaacaccau ugucacacuc c                                              21

<210> SEQ ID NO 33
<211> LENGTH: 19
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (1)..(15)
<223> OTHER INFORMATION: 2'-O-Me ribo sugar modification corresponding
      base
<220> FEATURE:
<221> NAME/KEY: modified_base
<222> LOCATION: 16, 17, 18, 19
<223> OTHER INFORMATION: 2'-O-Me ribo sugar modification
      phosphorothioate linkage corresponding base

<400> SEQUENCE: 33
aaacaccauu gucacacuc                                                 19

<210> SEQ ID NO 34
<211> LENGTH: 17
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: (3)..(13)
<223> OTHER INFORMATION: 2'-O-Me ribo sugar modification corresponding
      base
<220> FEATURE:
<221> NAME/KEY: modified_base
<222> LOCATION: 1, 2, 14,15, 16, 17
<223> OTHER INFORMATION: 2'-O-Me ribo sugar modification
      phosphorothioate linkage corresponding base

<400> SEQUENCE: 34
aacaccauug ucacacu                                                   17

<210> SEQ ID NO 35
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 20, 21, 22, 23
<223> OTHER INFORMATION: 2'-O-Me ribo sugar modification
      phosphorothioate linkage corresponding base
<220> FEATURE:
<221> NAME/KEY: modified_base
<222> LOCATION: (3)...(19)
```

```
<223> OTHER INFORMATION: 2'-O-Me ribo sugar modification corresponding
      base

<400> SEQUENCE: 35
acaaacaaca cugucacauu cca                                              23

<210> SEQ ID NO 36
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 36
acaaacacca cugucacauu cca                                              23

<210> SEQ ID NO 37
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 20, 21, 22, 23
<223> OTHER INFORMATION: 2'-O-Me ribo sugar modification
      phosphorothioate linkage corresponding base
<220> FEATURE:
<221> NAME/KEY: modified_base
<222> LOCATION: (3)...(19)
<223> OTHER INFORMATION: 2'-O-Me ribo sugar modification corresponding
      base

<400> SEQUENCE: 37
acaaacacca uugucacauu cca                                              23

<210> SEQ ID NO 38
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 20, 21, 22, 23
<223> OTHER INFORMATION: 2'-O-Me ribo sugar modification
      phosphorothioate linkage corresponding base
<220> FEATURE:
<221> NAME/KEY: modified_base
<222> LOCATION: (2)...(19)
<223> OTHER INFORMATION: 2'-O-Me ribo sugar modification corresponding
      base

<400> SEQUENCE: 38
acaaacacca uugucacacu cca                                              23

<210> SEQ ID NO 39
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 20, 21, 22, 23
<223> OTHER INFORMATION: 2'-O-Me ribo sugar modification
      phosphorothioate linkage corresponding base
<220> FEATURE:
<221> NAME/KEY: modified_base
<222> LOCATION: (2)...(19)
<223> OTHER INFORMATION: 2'-O-Me ribo sugar modification corresponding
      base
```

<400> SEQUENCE: 39
acacacaaca cugucacauu cca                                                    23

<210> SEQ ID NO 40
<211> LENGTH: 23
<212> TYPE: RNA
<213> ORGANISM: Artificial Sequence
<220> FEATURE:
<223> OTHER INFORMATION: Synthetically generated oligonucleotide

<400> SEQUENCE: 40
acaaacacca uugucacacu cca                                                    23

<210> SEQ ID NO 41
<211> LENGTH: 21
<212> TYPE: RNA
<213> ORGANISM: Artificial Sequence
<220> FEATURE:
<223> OTHER INFORMATION: Synthetically generated oligonucleotide

<400> SEQUENCE: 41
uaaggcacgc ggugaaugcc a                                                      21

<210> SEQ ID NO 42
<211> LENGTH: 35
<212> TYPE: DNA
<213> ORGANISM: Artificial Sequence
<220> FEATURE:
<223> OTHER INFORMATION: Primer

<400> SEQUENCE: 42
agtcagatgt acagttataa gcacaagagg accag                                       35

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
ttattcaaga tcccggggct cttcc                                                  25

<210> SEQ ID NO 44
<211> LENGTH: 25
<212> TYPE: DNA
<213> ORGANISM: Artificial Sequence
<220> FEATURE:
<223> OTHER INFORMATION: Primer

<400> SEQUENCE: 44
ccagagctga actaaggctg ctcca                                                  25

<210> SEQ ID NO 45
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 23
<223> OTHER INFORMATION: 2'-O-methyl modification phosphorothioate
      linkage corresponding base
<220> FEATURE:
<221> NAME/KEY: modified_base
<222> LOCATION: (1)...(22)

<223> OTHER INFORMATION: 2'-O-methyl modified nucleotides corresponding
      base

<400> SEQUENCE: 45
acaaacacca uugucacacu cca                                              23

<210> SEQ ID NO 46
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 20, 21, 22, 23
<223> OTHER INFORMATION: 2'-O-Me ribo sugar modification
      phosphorothioate linkage corresponding base
<220> FEATURE:
<221> NAME/KEY: modified_base
<222> LOCATION: (3)...(19)
<223> OTHER INFORMATION: 2'-O-Me ribo sugar modification corresponding
      base

<400> SEQUENCE: 46
ccaaacacca uugucacacu cca                                              23

<210> SEQ ID NO 47
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 20, 21, 22, 23
<223> OTHER INFORMATION: 2'-O-Me ribo sugar modification
      phosphorothioate linkage corresponding base
<220> FEATURE:
<221> NAME/KEY: modified_base
<222> LOCATION: (3)...(19)
<223> OTHER INFORMATION: 2'-O-Me ribo sugar modification corresponding
      base

<400> SEQUENCE: 47
acaaacacca cugucacacu cca                                              23

<210> SEQ ID NO 48
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 13, 14
<223> OTHER INFORMATION: 2'-O-Me ribo sugar modification corresponding
      base

<400> SEQUENCE: 48
uggaguguga caauguguuu ugu                                              23

<210> SEQ ID NO 49
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 2, 20, 21, 22
<223> OTHER INFORMATION: 2'-O-Me ribo sugar modification
      phosphorothioate linkage corresponding base

```
<400> SEQUENCE: 49
uggaguguga caaugguguu ugu                                           23

<210> SEQ ID NO 50
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 20, 21, 22, 23
<223> OTHER INFORMATION: 2'-O-Me ribo sugar modification
      phosphorothioate linkage corresponding base

<400> SEQUENCE: 50
acaaacacca uugucacacu cca                                           23

<210> SEQ ID NO 51
<211> LENGTH: 23
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: modified_base
<222> LOCATION: 1, 20, 21, 22, 23
<223> OTHER INFORMATION: 2'-O-Me ribo sugar modification
      phosphorothioate linkage corresponding base

<400> SEQUENCE: 51
acacacaaca cugucacauu cca                                           23
```

CHEMICALLY MODIFIED OLIGONUCLEOTIDES FOR USE IN MODULATION MICRO RNA AND USES THEREOF

CROSS-REFERENCE TO RELATED APPLICATIONS

This application is a Continuation of prior U.S. patent application Ser. No. 11/657,341, filed Jan. 24, 2007, which is a Continuation In Part of U.S. patent application Ser. No. 11/502,158, filed Aug. 10, 2006, which are entitled to priority under 35 U.S.C. §119(e) to U.S. Provisional Patent Application No. 60/706,866, filed Aug. 10, 2005, U.S. Provisional Patent Application No. 60/731,554, filed Oct. 28, 2005, and U.S. Provisional Patent Application No. 60/763,201, filed Jan. 26, 2006. The contents of each of these priority applications are incorporated herein by reference in their entirety.

GOVERNMENT SUPPORT

This invention was made with government support under NIH Grant No. 1 P01 GM073047-01, awarded by the National Institutes of Health. The government has certain rights in the invention.

TECHNICAL FIELD

This invention relates generally to chemically modified oligonucleotides (antagomirs) useful for modulating expression of microRNAs. More particularly, the invention relates to single stranded, double stranded, partially double stranded and hairpin structured chemically modified oligonucleotides for inhibiting microRNA expression and to methods of making and using the modified oligonucleotides.

BACKGROUND

A variety of nucleic acid species are capable of modifying gene expression. These include antisense RNA, siRNA, microRNA, RNA and DNA aptamers, and decoy RNAs. Each of these nucleic acid species can inhibit target nucleic acid activity, including gene expression.

MicroRNAs (miRNAs) are a class of 18-24 nt non-coding RNAs (ncRNAs) that exist in a variety of organisms, including mammals, and are conserved in evolution. miRNAs are processed from hairpin precursors of 70 nt (pre-miRNA) which are derived from primary transcripts (pri-miRNA) through sequential cleavage by the RNAse III enzymes drosha and dicer. Many microRNAs can be encoded in intergenic regions, hosted within introns of pre-mRNAs or within ncRNA genes. Many miRNAs also tend to be clustered and transcribed as polycistrons and often have similar spatial temporal expression patterns. MiRNAs have been found to have roles in a variety of biological processes including developmental timing, differentiation, apoptosis, cell proliferation, organ development, and metabolism.

miRNAs are an abundant class of non-coding RNA ranging from 20 to 23 nucleotides of length that are post-transcriptional regulators of gene expression. miRNAs have been mainly associated with developmental processes in metazoa such as *Caenorhabditis elegans* or *Drosophila melanogaster* (Ambros, 2004 *Nature* 431:350-5). However, evidence also suggests a role for miRNAs in a wide range of functions in mammals, including insulin secretion, heart, skeletal muscle and brain development (Kloosterman, et al., 2006 *Dev Cell* 11:441-50, and Krutzfeldt, et al., 2006 *Cell Metab* 4:9-12).

Furthermore, miRNAs have been implicated in diseases such as cancer (Esquela-Kerscher, et al., 2006 *Nat Rev Cancer* 6:259-69) and hepatitis C (Jopling, et al., 2005 *Science* 309: 1577-81), which make them attractive new drug targets. In contrast to the widely used RNAi technology using small interfering RNA (siRNA) duplexes, strategies to inhibit miRNAs have been less well investigated. Reverse-complement 2'-O-methyl sugar modified RNA is frequently being used to block miRNA function in cell-based systems (Krutzfeldt, et al., 2006 *Nat Genet* 38:S14-9). The use of miRNA inhibitors, however, remains challenging. Thus, there is a long felt need in the art for efficient and directed means of inhibiting miRNA. The present invention satisfies this need.

SUMMARY

The present invention is based in part on the discovery that expression of endogenous microRNAs (miRNAs) or pre-microRNAs (pre-miRNAs) can be inhibited by an agent herein defined as an antagomir, e.g., through systemic or local administration of the antagomir, as well as by parenteral administration of such agents. However, the invention should not be limited to any particular route of administration, The present invention provides specific compositions and methods that are useful in reducing miRNA and pre-miRNA levels, in e.g., a mammal, such as a human. In particular, the present invention provides specific compositions and methods that are useful for reducing levels of the miRNAs miR-122, miR-16, miR-192, and miR-194.

In one aspect, the invention features antagomirs. Antagomirs are single stranded, double stranded, partially double stranded and hairpin structured chemically modified oligonucleotides that target a microRNA. FIGS. 5-11 provides repsresentative structures of antagomirs.

An antagomir consisting essentially of or comprising at least 12 or more contiguous nucleotides substantially complementary to an endogenous miRNA and more particularly agents that include 12 or more contiguous nucleotides substantially complementary to a target sequence of an miRNA or pre-miRNA nucleotide sequence. Preferably, an antagomir featured in the invention includes a nucleotide sequence sufficiently complementary to hybridize to a miRNA target sequence of about 12 to 25 nucleotides, preferably about 15 to 23 nucleotides. More preferably, the target sequence differs by no more than 1, 2, or 3 nucleotides from a sequence shown in Table 1, and in one embodiment, the antagomir is an agent shown in Table 2a-e, Table 4, and Table 7. In one embodiment, the antagomir includes a non-nucleotide moiety, e.g., a cholesterol moiety. The non-nucleotide moiety can be attached, e.g., to the 3' or 5' end of the oligonucleotide agent. In a preferred embodiment, a cholesterol moiety is attached to the 3' end of the oligonucleotide agent.

Antagomirs are stabilized against nucleolytic degradation such as by the incorporation of a modification, e.g., a nucleotide modification. In another embodiment, the antagomir includes a phosphorothioate at least the first, second, or third internucleotide linkage at the 5' or 3' end of the nucleotide sequence. In yet another embodiment, the antagomir includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In a particularly preferred embodiment, the antagomir includes at least one 2'-O-methyl-modified nucleotide, and in some embodiments, all of the nucleotides of the antagomir include a 2'-O-methyl modification.

In one aspect, antagomirs are RNA-like oligonucleotides that harbor various modifications for RNase protection and pharmacologic properties such as enhanced tissue and cellular uptake. A preferred antagomir differs from normal RNA by having complete 2'-O-methylation of sugar, phosphorothioate backbone and a cholesterol-moiety at 3'-end. Phosphorothioate modifications provide protection against RNase activity and their lipophilicity contributes to enhanced tissue uptake. In a preferred embodiment, the antagomir includes six phosphorothioate backbone modifications; two phosphorothioates are located at the 5'-end and four at the 3'-end.

Antagomirs of the present invention can also be modified with respect to their length or otherwise the number of nucleotides making up the antagomir. In some instances, it is preferred that the antagomirs of the present invention are of at least 19 nucleotides in length for optimal function.

An antagomir that is substantially complementary to a nucleotide sequence of an miRNA can be delivered to a cell or a human to inhibit or reduce the activity of an endogenous miRNA, such as when aberrant or undesired miRNA activity, or insufficient activity of a target mRNA that hybridizes to the endogenous miRNA, is linked to a disease or disorder. In one embodiment, an antagomir featured in the invention has a nucleotide sequence that is substantially complementary to miR-122 (see Table 1), which hybridizes to numerous RNAs, including aldolase A mRNA, N-myc downstram regulated gene (Ndrg3) mRNA, IQ motif containing GTPase activating protein-1 (Iqgap1) mRNA, HMG-CoA-reductase (Hmgcr) mRNA, and citrate synthase mRNA and others. In a preferred embodiment, the antagomir that is substantially complementary to miR-122 is antagomir-122 (Table 2a-e, Table 4, and Table 7). Aldolase A deficiencies have been found to be associated with a variety of disorders, including hemolytic anemia, arthrogryposis complex congenita, pituitary ectopia, rhabdomyolysis, hyperkalemia. Humans suffering from aldolase A deficiencies also experience symptoms that include growth and developmental retardation, midfacial hypoplasia, hepatomegaly, as well as myopathic symptoms. Thus a human who has or who is diagnosed as having any of these disorders or symptoms is a candidate to receive treatment with an antagomir that hybridizes to miR-122.

In some embodiments, an antagomir featured in the invention has a nucleotide sequence that is substantially complementary to miR-16, miR-192, or miR-194.

In one aspect, the invention features a method of reducing the levels of an miRNA or pre-miRNA in a cell of a subject, e.g., a human subject. In another aspect, the invention includes reducing the level of an miRNA or pre-miRNA in a cell of the central nervous system. The method includes the step of administering an antagomir to the subject, where the antagomir is substantially single-stranded and includes a sequence that is substantially complementary to 12 to 23 contiguous nucleotides, and preferably 15 to 23 contiguous nucleotides, of a target sequence of an miRNA or pre-miRNA nucleotide sequence. Preferably, the target sequence differs by no more than 1, 2, or 3 nucleotides from a microRNA or pre-microRNA sequence, such as a microRNA sequence shown in Table 1.

In one embodiment, the methods featured in the invention are useful for reducing the level of an endogenous miRNA (e.g., miR-122, miR-16, miR-192 or miR-194) or pre-miRNA in a cell, e.g, in a cell of a subject, such as a human subject. Preferably, the cell is a cell of the central nervous system. Such methods include contacting the cell with an antagomir described herein for a time sufficient to allow uptake of the antagomir into the cell.

In another aspect, the invention features a pharmaceutical composition including an antagomir described herein, and a pharmaceutically acceptable carrier. In a preferred embodiment, the antagomir included in the pharmaceutical composition hybridizes to miR-122, miR-16, miR-192, or miR-194.

In another aspect the invention features a method of inhibiting miRNA expression (e.g., miR-122, miR-16, miR-192, or miR-194 expression) or pre-miRNA expression in a cell, e.g., a cell of a subject. Preferably, the cell is a cell of the central nervous system. The method includes contacting the cell with an effective amount of an antagomir described herein, which is substantially complementary to the nucleotide sequence of the target miRNA or the target pre-miRNA. Such methods can be performed on a mammalian subject by administering to a subject one of the oligonucleotide agents/pharmaceutical compositions described herein.

In another aspect the invention features a method of increasing levels of an RNA or protein that are encoded by a gene whose expression is down-regulated by an miRNA, e.g., an endogenous miRNA, such as miR-122, miR-16, miR-192 or mir-194. The method includes contacting the cell with an effective amount of an antagomir described herein, which is substantially complementary to the nucleotide sequence of the miRNA that binds to and effectively inhibits translation of the RNA transcribed from the gene. For example, the invention features a method of increasing aldolase A protein levels in a cell. Similarly, the invention features a method of increasing Ndrg3, Iqgap1, Hmgcr, and/or citrate synthase protein levels in a cell. The methods include contacting the cell with an effective amount of an antagomir described herein (e.g., antagomir-122, described in Table 2a-e, Table 4, and Table 7), which is substantially complementary to the nucleotide sequence of miR-122 (see Table 1).

In another aspect, the invention provides methods of increasing expression of a target gene by providing an antagomir to which a lipophilic moiety is conjugated, e.g., a lipophilic conjugated antagomir described herein, to a cell. The antagomir preferably hybridizes to an miRNA (e.g., miR-122, miR-16, miR-192, or miR-194) or a pre-miRNA. In a preferred embodiment the conjugated antagomir can be used to increase expression of a target gene in an organism, e.g., a mammal, e.g., a human, or to increase expression of a target gene in a cell line or in cells which are outside an organism. An mRNA transcribed from the target gene hybridizes to an endogenous miRNA, which consequently results in down-regulation of mRNA expression. An antagomir featured in the invention hybridizes to the endogenous miRNA and consequently causes an increase in mRNA expression. In the case of a whole organism, the method can be used to increase expression of a gene and treat a condition associated with a low level of expression of the gene. For example, an antagomir that targets miR-122 (e.g., antagomir-122) can be used to increase expression of an aldolase A gene to treat a subject having, or at risk for developing, hemolytic anemia, arthrogryposis complex congenita, pituitary ectopia, rhabdomyolysis, hyperkalemia, or any other disorder associated with aldolase A deficiency. Administration of an antagomir that targets miR-122 (e.g., antagomir-122) can be also be used to increase expression of an Ndrg3, Iqgap1, Hmgcr, or citrate synthase gene to treat a subject having, or at risk for developing, a disorder associated with a decreased expression of any one of these genes.

DESCRIPTION OF DRAWINGS

For the purpose of illustrating the invention, there are depicted in the drawings certain embodiments of the invention. However, the invention is not limited to the precise arrangements and instrumentalities of the embodiments depicted in the drawings.

FIG. 5 depicts ligand conjugated oligonucleotide to modulate expression of miRNA: (a) ligand of interest is conjugated to the oligonucleotide via a tether and linker; (b) ligand of interest is conjugated to the oligonucleotide via a linker without a tether or tether without an additional linker and (c) a ligand of interest is attached directly to the oligonucleotide.

FIG. 10 depicts ligand conjugated hairpin oligonucleotides to modulate expression of miRNA. (a) ligand of interest is conjugated to either 3' or 5' end of the hairpin via a tether and linker; (b) ligand of interest is conjugated to the hairpin via a linker without a tether or tether without an additional linker and (c) a ligand of interest is attached directly to the oligonucleotide. The hairpin is comprised of nucleotides or non-nucleotide linkages.

FIG. 11 depicts cholesterol conjugated oligonucleotides to modulate expression of miRNA. (a) 5' cholesterol conjugate; (b) 3' cholesterol conjugate and (c) cholesterol conjugate building blocks for oligonucleotide synthesis. The oligonucleotide can be miRNA, anti-miRNA, chemically modified RNA or DNA; DNA or DNA analogues for antisense application.

FIG. 17, comprising FIGS. 17A through 17C, is a series of charts demonstrating the impact of antagomir phosphorothioate modifications and antagomir length on miR-122 levels. FIG. 17 comprises Northern blots of total RNA isolated from livers of mice that were treated with different antagomir-122 chemistries at 3×20 mg/kg bw. FIG. 17A demonstrates the impact of mm-antagomir-122, antagomir-122 (no phosphorothioate modification), and antagomir-122 on the RNA level of miR-122. FIG. 17B demonstrates the impact of different phosphorothioate modifications to the antagomir on the RNA level of miR-122. FIG. 17C demonstrates the impact of different lengths to the antagomir on the RNA level of miR-122. "P=S" indicates phosphorothioate modification.

FIGS. 18A and 18B, is a series of charts demonstrating dose- and time-dependency of miR-122 target regulation by antagomir-122. FIG. 18A depicts a dose-dependent study. FIG. 18B is a time-course experiment. Also depicted in FIGS. 18A and 18B are the steady-state mRNA levels of miR-122 target genes in livers of mice treated with the indicated amounts or duration of antagomir-122. The glyceraldehyde-3-phosphate dehydrogenase gene (Gapdh) was used as a loading control. The upper row in each chart shows a Northern blot of liver RNA for miR-122.

FIGS. 19A and 19B, is a series of charts demonstrating sequence discrimination of antagomir-122. FIG. 19 depicts steady-state mRNA levels of miR-122 target genes in livers of mice treated with the indicated amounts of antagomir-122 or antagomir-122 that harbored 4, 2 or 1 nucleotide mismatches (FIG. 19A), or 1 nucleotide mismatch at different positions (FIG. 19B).

FIG. 20, comprising FIGS. 20A and 20B, is a series of charts demonstrating the regulation of miR-122 targets by chemically protected antagomir-122/miR-122-duplexes. FIG. 20A is a schematic description of two different duplexes used. FIG. 20B depicts the steady-state mRNA levels of miR-122 target genes in livers of mice treated with the indicated modified antagomir-122/miR-122-duplexes. Fold-regulation indicates the ratio of expression levels of the means of mice treated with antagomir-122/miR-122 duplex compared to the PBS group. The upper row shows a Northern blot of liver RNA for miR-122. As controls, duplexes were added to 5 µg total kidney RNA and loaded on polyacrylamide gels before ("input") or after the Trizol protocol ("Trizol"). *:$p<0.05$; :$p<0.01$; *:$p<0.001$; student's t-test compared to PBS.

FIGS. 21A through 21C, is a series of charts that demonstrate localization of antagomir-122 and miR-122 in hepatocytes. Liver tissue from mice that were treated with 3×80 mg/kg Q570-labeled mm-antagomir-122 was fractionated on a sucrose gradient following ultracentrifugation. Localization of Q570-labeled mm-antagomir-122 was analyzed by spectrophotometry (FIG. 21A). Localization of t-RNA and miR-122 were analyzed using Northern blotting of total RNA isolated from each fraction (FIG. 21B). For subcellular localization of antagomirs and P-bodies in mouse liver, mice were treated with Q570-labeled antagomir-122 and a DNA-plasmid expressing a GFP-GW182 hybrid. P-body and Q570-antagomir localizations were visualized using laser-scanning microscopy (FIG. 21C).

FIG. 25 is a chart demonstrating metabolic parameters of antagomir-122 treated mice.

Figure 23:
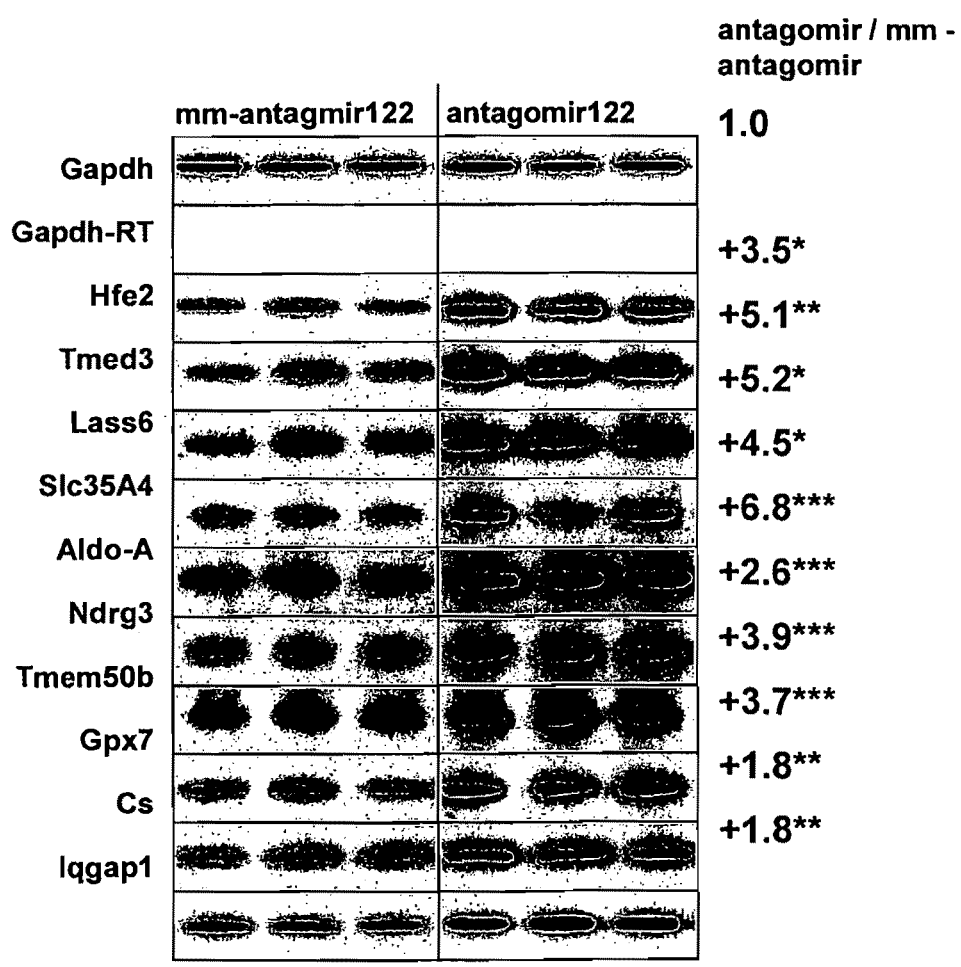
FIG. 23 is a chart demonstrating that miR-122 regulates mRNA levels of many targets.
Figure 24:
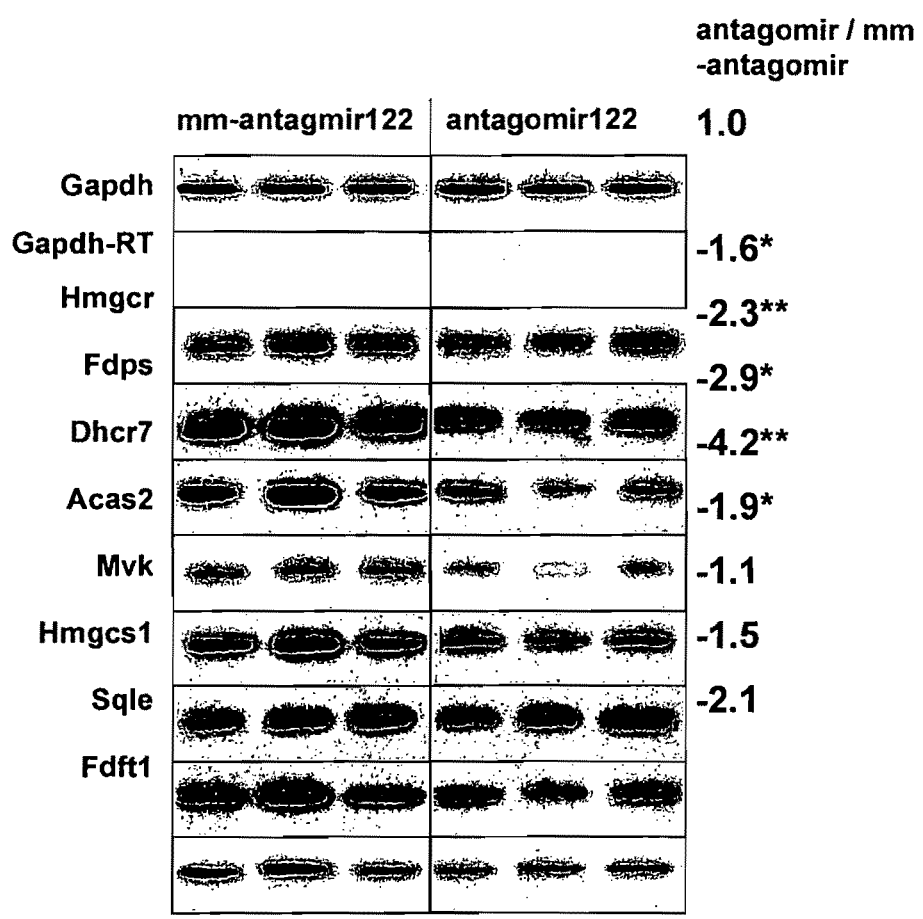
FIG. 24 is a chart demonstrating that miR-122 regulates the expression of cholesterol biosynthesis genes.

The following experiments are designed to study miRNA function in vivo. Typically, gene expression profiling, bioinformatics analysis, metabolic profiling, and biochemical target validation is performed. Using methods discussed elsewhere herein, miR-122 was observed to regulate levels of many target genes (FIG. 23). Moreover, miR-122 was observed to regulate the expression of cholesterol biosynthesis genes (FIG. 24). Based on the genes observed to be regulated by miR-122, metabolic parameters of antagomir-122 treated mice were evaluated. The results demonstrated that mice treated with antagomir-122 exhibited a decrease in cholesterol as compared with mice treated with mm-antagomir. The results presented herein characterize the inhibition of miRNAs with antagomirs in vivo and their therapeutic use with respect to cholesterol levels.

DETAILED DESCRIPTION

The present invention is based in part on the discovery that expression of endogenous microRNAs (miRNAs) or pre-microRNAs (pre-miRNAs) can be inhibited by an antagomir, e.g., through systemic administration of an antagomir, as well as by parenteral administration of such agents. Based on these findings, the present invention provides specific compositions and methods that are useful in reducing miRNA and pre-miRNA levels, in e.g., a mammal, such as a human. In particular, the present invention provides specific compositions and methods that are useful for reducing levels of the miRNAs miR-122, miR-16, miR-192, and miR-194, herein defined as antagomirs.

In one aspect, the invention features antagomirs. An antagomir is a single-stranded, double stranded, partially double stranded or hairpin structured chemically modified oligonucleotide agents that consisting of, consisting essentially of or comprising at least 12 or more contiguous nucleotides substantially complementary to an endogenous miRNA and more particularly agents that include 12 or more contiguous nucleotides substantially complementary to a target sequence of an miRNA or pre-miRNA nucleotide sequence. As used herein partially double stranded refers to double stranded structures that contain less nucleotides than the complementary strand. In general, such partial double stranded agents will have less than 75% double stranded structure, preferably less than 50%, and more preferably less than 25%, 20% or 15% double stranded structure. FIGS. 5-11 provides representative structures of antagomirs.

Preferably, an antagomir featured in the invention includes a nucleotide sequence sufficiently complementary to hybridize to an miRNA target sequence of about 12 to 25 nucleotides, preferably about 15 to 23 nucleotides. More preferably, the target sequence differs by no more than 1, 2, or 3 nucleotides from a sequence shown in Table 1, and in one embodiment, the antagomir is an agent shown in Table 2a-e, Table 4 and Table 7. In one embodiment, the antagomir includes a non-nucleotide moiety, e.g., a cholesterol moiety. The non-nucleotide moiety can be attached, e.g., to the 3' or 5' end of the oligonucleotide agent. In a preferred embodiment, a cholesterol moiety is attached to the 3' end of the oligonucleotide agent.

In another aspect, the length of the antagimor can contribute to the biochemical function of the antagimor with respect to the ability to decrease expression levels of a desired miRNA. An miRNA-type antagomir can be, for example, from about 12 to 30 nucleotides in length, preferably about 15 to 28 nucleotides in length (e.g., 16, 17, 18, 19, 20, 21, 22, 23, 24, 25, 26, or 27 nucleotides in length). In some instances, antagomirs may require at least 19 nucleotides in length for optimal function.

The antagomir is further stabilized against nucleolytic degradation such as by the incorporation of a modification, e.g., a nucleotide modification. The antagomir includes a phosphorothioate at least the first, second, or third internucleotide linkage at the 5' or 3' end of the nucleotide sequence. In one embodiment, the antagomir includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In a particularly preferred embodiment, the antagomir includes at least one 2'-O-methyl-modified nucleotide, and in some embodiments, all of the nucleotides of the antagomir include a 2'-O-methyl modification. In yet another preferred embodiment, the antagomir includes six phosphorothioate backbone modifications; two phosphorothioates are located at the 5'-end and four at the 3'-end. In a preferred embodiment, the antagimor comprises 19 nucleotides and six phosphorothioate backbone modifications.

The antagomir is further modified so as to be attached to a ligand that is selected to improve stability, distribution or cellular uptake of the agent, e.g., cholesterol. In a preferred embodiment, the antagimor comprises 19 nucleotides, six phosphorothioate backbone modifications and a ligand to improve stability, distribution or cellular uptake of the antagomir. The oligonucleotide antagomir can further be in isolated form or can be part of a pharmaceutical composition used for the methods described herein, particularly as a pharmaceutical composition formulated for parental administration. The pharmaceutical compositions can contain one or more oligonucleotide agents, and in some embodiments, will contain two or more oligonucleotide agents, each one directed to a different miRNA.

An antagomir that is substantially complementary to a nucleotide sequence of an miRNA can be delivered to a cell or a human to inhibit or reduce the activity of an endogenous miRNA, such as when aberrant or undesired miRNA activity, or insufficient activity of a target mRNA that hybridizes to the endogenous miRNA, is linked to a disease or disorder. In one embodiment, an antagomir featured in the invention has a nucleotide sequence that is substantially complementary to miR-122 (see Table 1), which hybridizes to numerous RNAs, including aldolase A mRNA, N-myc downstream regulated gene (Ndrg3) mRNA, 1Q motif containing GTPase activating protein-1 (Iqgap1) mRNA, HMG-CoA-reductase (Hmgcr) mRNA, and citrate synthase mRNA and others. In a preferred embodiment, the antagomir that is substantially complementary to miR-122 is antagomir-122 (Table 2a-e, Table 4 and Table 7). Aldolase A deficiencies have been found to be associated with a variety of disorders, including hemolytic anemia, arthrogryposis complex congenita, pituitary ectopia, rhabdomyolysis, hyperkalemia. Humans suffering from aldolase A deficiencies also experience symptoms that include growth and developmental retardation, midfacial hypoplasia, hepatomegaly, as well as myopathic symptoms. Thus a human who has or who is diagnosed as having any of these disorders or symptoms is a candidate to receive treatment with an antagomir, such as a single-stranded oligonucleotide agent, that hybridizes to miR-122.

In some embodiments, an antagomir featured in the invention has a nucleotide sequence that is substantially complementary to miR-16, miR-192, or miR-194 (see Table 1).

In one embodiment, the antagomiris selected from those shown in Table 2a-e, Table 4 and Table 7. The single-stranded oligonucleotide agents of Table 2a-e, Table 4 and Table 7 are complementary to and hybridize to the corresponding miRNAs of Table 1.

TABLE 1

Exemplary miRNAs identified in *mus musculus*

| miRNA | Sequence | SEQ ID NO: |
|---|---|---|
| miR-122 | 5'-UGGAGUGUGACAAUGGUGUUUGU-3' | 1 |
| miR-16 | 5'-UAGCAGCACGUAAAUAUUGGCG-3' | 2 |
| miR-192 | 5'-CUGACCUAUGAAUUGACAGCC-3' | 3 |
| miR-194 | 5'-UGUAACAGCAACUCCAUGUGGA-3' | 4 |

TABLE 2a

Oligonucleotide agents targeting *mus musculus* miRNAs

| RNA | Sequence | SEQ ID NO: |
|---|---|---|
| antagomir-122 | 5'-a$_s$c$_s$aaacaccauugucacacu$_s$c$_s$c$_s$a$_s$-Chol-3' | 5 |
| antagomir-16 | 5'-c$_s$g$_s$ccaauauuuacgugcug$_s$c$_s$u$_s$a$_s$-Chol-3' | 6 |
| antagomir-192 | 5'-g$_s$g$_s$cugucaauucauaggu$_s$c$_s$a$_s$g$_s$-Chol-3' | 7 |
| antagomir-194 | 5'-u$_s$c$_s$cacauggaguugcuguu$_s$a$_s$c$_s$a$_s$-Chol-3' | 8 | lower case letters represent 2'-O-methyl modified nucleotides;
subscript 's' represents a phosphorothioate linkage;
"Chol" indicates cholesterol conjugate TABLE 2b Double stranded oligonucleotides to modulate microRNAs

| Duplex ID | Sequence ID and sequence |
|---|---|
| AL-DP-3018 | AL-SQ-3035: UGGAGUGUGACAAUGGUGUUUGU (SEQ ID NO: 1)<br>AL-SQ-3037:<br>oAsoCsoAsoAsoAsoCsoAsoCsoCsoAsoUsoUsoGsoUsoCsoAsoCsoAsoCsoUsoCsoCsoAs-Chol (SEQ ID NO: 10) |
| AL-DP-3019 | AL-SQ-3035: UGGAGUGUGACAAUGGUGUUUGU (SEQ ID NO: 1)<br>AL-SQ-3038: oAsoCsoAoAoAoCoAoCoCoAoUoUoGoUoCoAoCoAoCoUsoCsoCsoAs-Chol (SEQ ID NO: 11) |
| AL-DP-3020 (mismatch) | AL-SQ-3036: UGGAAUGUGACAGUGUUGUGUGU (SEQ ID NO: 12)<br>AL-SQ-3039:<br>oAsoCsoAsoCsoAsoCsoAsoAsoCsoAsoCsoUsoGsoUsoCsoAsoCsoAsoUsoUsoCsoCsoAs-Chol (SEQ ID NO: 13) |
| AL-DP-3021 (mismatch) | AL-SQ-3036: UGGAAUGUGACAGUGUUGUGUGU (SEQ ID NO: 12)<br>AL-SQ-3040: oAsoCsoAoCoAoCoAoAoCoAoCoUoGoUoCoAoCoAoUoUsoCsoCsoAs-Chol (SEQ ID NO: 14) |

Note:
oN represents 2'-O-Me ribo sugar modification,
dN represents deoxyribo sugar modification and 's' stands for phosphorothioate linkage

TABLE 2c

Partial double stranded and hairpin structured oligonucleotides to modulate microRNA-122

| Sequence ID | Sequence |
|---|---|
| AL-SQ-3384 | oAoCoAoAoAoCoAoCoCoAoUoUoGoUoCoAoCoAoCo UoCoCoAdTdTdTdToUoGoGoAs-Chol (SEQ ID NO: 15) |
| AL-SQ-3385 | oAoCoAoAoAoCoAoCoCoAoUoUoGoUoCoAoCoAoCo UoCoCoAsdTsdTsdTsdTsoUoGoGoAs-Chol (SEQ ID NO: 16) |

Note:
oN represents 2'-O-Me ribo sugar modification, dN represents deoxyribo sugar modification and 's' stands for phosphorothioate linkage

TABLE 2d

Partial double stranded oligonucleotides to modulate microRNA-122

| Duplex ID | Sequence ID and sequence | SEQ ID NO: |
|---|---|---|
| AL-DP-3043 | AL-SQ-3038: oAsoCsoAoAoAoCoAoCoCoAoUoUoGoUoCoAoCoAoCoUsoCsoCsoAs-Chol | 11 |
| | AL-SQ-3400: oUoGoGoAoGoUoG (7-mer at the 3'-end) | 17 |
| AL-DP-3044 | AL-SQ-3038: oAsoCsoAoAoAoCoAoCoCoAoUoUoGoUoCoAoCoAoCoUsoCsoCsoAs-Chol | 11 |
| | AL-SQ-3401: oGoAoCoAoAoUoG (7-mer at nts 9-15) | 18 |
| AL-DP-3045 | AL-SQ-3040: oAsoCsoAoCoAoCoAoAoCoAoCoUoGoUoCoAoCoAoUoUsoCsoCsoAs-Chol | 14 |
| | AL-SQ-3402: oUoGoGoAoAoUoG (7-mer at the 3'-end) | 19 |
| AL-DP-3046 | AL-SQ-3040: oAsoCsoAoCoAoCoAoAoCoAoCoUoGoUoCoAoCoAoUoUsoCsoCsoAs-Chol | 14 |
| | AL-SQ-3403: oGoAoCoAoGoUoG (7-mer at nts 9-15) | 20 |

Note:
oN represents 2'-O-Me ribo sugar modification, dN represents deoxyribo sugar modification and 's' stands for phosphorothioate linkage

TABLE 2e

Single stranded oligonucleotides to modulate microRNAs

| Sequence ID | Sequence | SEQ ID NO: |
|---|---|---|
| AL-SQ-3035 | UGGAGUGUGACAAUGGUGUUUGU | 1 |
| AL-SQ-3036 | UGGAAUGUGACAGUGUUGUGUGU | 12 |
| AL-SQ-3037 | oAsoCsoAsoAsoAsoCsoAsoCsoCsoAsoUsoUsoGsoUsoCsoAsoCsoAsoCsoUsoCsoCsoAs-Chol | 10 |
| AL-SQ-3038 | oAsoCsoA oAoAoC oAoCoC oAoUoU oGoUoC oAoCoA oCoUsoCs oCsoAs-chol | 11 |
| AL-SQ-3039 | oAsoCsoAsoCsoAsoCsoAsoAsoCsoAsoCsoUsoGsoUsoCsoAsoCsoAsoUsoUsoCsoCsoAs-Chol | 13 |
| AL-SQ-3040 | oAsoCsoA oCoAoC oAoAoC oAoCoU oGoUoC oAoCoA oUcUsoCs oCsoAs-chol | 14 |
| AL-SQ-3223 | oUsoGsoG oAoGoU oGoUoG oAoCoA oAoUoG oGoUoG oUoUsoUs oGsoUs-chol | 21 |
| AL-SQ-3224 | oUsoGsoG oAoAoU oGoUoG oAoCoA oGoUoG oUoUoG oUoGsoUs oGsoUs-chol | 22 |
| AL-SQ-3225 | oAsoCsoAs oAsoAsoCs oAsoCsoCs oAsoUsoUs oGsoUsoCs oAsoCsoAs oCsoUsoCs oCsoA | 23 |
| AL-SQ-3226 | oAsoCsoA oAoAoC oAoCoC oAoUoU oGoUoC oAoCoA oC*oU*oC* oC*Oa | 24 |
| AL-SQ-3227 | oCsoGsoC oCoAoA oUoAoU oUoUoA oCoGoU oGoCoU oG*oC*oU* oA*-chol | 25 |
| AL-SQ-3228 | oGsoGsoC oUoGoU oCoAoA oUoUoC oAoUoA oGoGoU* oC*oA*oG*-chol | 26 |
| AL-SQ-3229 | oUsoCsoC oAoCoA oUoGoG oAoGoU oUoGoC oUoGoU oU*oA*oC* oA*-chol | 27 |
| AL-SQ-3230 | oUsoCsoA oCoGoC oGoAoG oCoCoG oAoAoC oGoAoA oCsoAsoAs oAs-chol | 28 |

TABLE 2e-continued

Single stranded oligonucleotides to modulate microRNAs

| Sequence ID | Sequence | SEQ ID NO: |
|---|---|---|
| AL-SQ-3344 | UGGIGUGUGICIIUGGUGUUUGU | 29 |
| AL-SQ-3350 | oAoCoAoAoAoCoAoCoCoAoUoUoGoUoCoAoCoAoCoUoCoCoA-Chol | 30 |
| AL-SQ-3351 | oCsoAsoCoAoAoCoAoCoCoAoUoUoGoUoCoAoCoAoCoUoCsoCsoAsoCs-Chol | 31 |
| AL-SQ-3352 | oCsoAsoAoAoCoAoCoCoAoUoUoGoUoCoAoCoAoCsoUsoCsoCs-Chol | 32 |
| AL-SQ-3353 | oAsoAsoAoCoAoCoCoAoUoUoGoUoCoAoCoAsoCsoUsoCs-Chol | 33 |
| AL-SQ-3354 | oAsoAsoCoAoCoCoAoUoUoGoUoCoAoCsoAsoCsoUs-Chol | 34 |
| AL-SQ-3355 | oAsoCsoAoAoCoAoAoCoAoCoUoGoUoCoAoCoAoUoUsoCsoCsoAs-Chol | 35 |
| AL-SQ-3356 | oAsoCsoAoAoCoAoCoCoAoCoUoGoUoCoAoCoAoUoUsoCsoCsoAs-Chol | 36 |
| AL-SQ-3357 | oAsoCsoAoAoCoAoCoCoAoUoUoGoUoCoAoCoAoUoUsoCsoCsoAs-Chol | 37 |
| AL-SQ-3358 | Cy-5-soAsoCoAoAoCoAoCoCoAoUoUoGoUoCoAoCoAoCoUsoCsoCsoAs-Chol | 38 |
| AL-SQ-3359 | Cy-3-soAsoCoAoCoAoCoAoAoCoAoCoUoGoUoCoAoCoAoUoUsoCsoCsoAs-Chol | 39 |

Cy-5 and Cy-3 are dyes used for localization studies.

TABLE 2f

Description of sequences listed in Table 2b-2e

| Sequence # | Description |
|---|---|
| AL-SQ-3035 | complementary to antagomir-122 |
| AL-SQ-3036 | complementary to mm-antagomir-122 |
| AL-SQ-3037 | antagomir-122-fullyPS |
| AL-SQ-3038 | antagomir-122 |
| AL-SQ-3039 | mm-antagomir-122-fullyPS |
| AL-SQ-3040 | mm-antagomir-122 |
| AL-SQ-3223 | complementary to antagomir-122 |
| AL-SQ-3224 | complementary to mm-antagomir-122 |
| AL-SQ-3225 | anti-122fs |
| AL-SQ-3226 | anti-122ps |
| AL-SQ-3227 | antagomir-16 |
| AL-SQ-3228 | antagomir-192 |
| AL-SQ-3229 | antagomir-194 |
| AL-SQ-3230 | antagomir-375 |
| AL-SQ-3344 | complementary to antagomir-122 with A->I modification |
| AL-SQ-3350 | antagomir-122-noPS |
| AL-SQ-3351 | antagomir-122-25mer |
| AL-SQ-3352 | antagomir-122-21mer |
| AL-SQ-3353 | antagomir-122-19mer |
| AL-SQ-3354 | antagomir-122-17mer |
| AL-SQ-3355 | mismatch-antagomir-122-3mm |
| AL-SQ-3356 | mismatch-antagomir-122-2mm |
| AL-SQ-3357 | mismatch-antagomir-122-1mm |
| AL-SQ-3358 | antagomir-122-5'-Cy5 |
| AL-SQ-3359 | antagomir-122-5'-Cy3 |
| AL-SQ-3400 | 7-mer complementary to 3'-end of antagomir-122 |
| AL-SQ-3401 | 7-mer complementary to nucleotides 9-15 of antagomir-122 |
| AL-SQ-3402 | 7-mer complementary to 3'-end of mismatch-antagamir-122 |
| AL-SQ-3403 | 7-mer complementary to nucleotides 9-15 of mismatch-antagomir-122 |

In one aspect, the invention features an antagomir, such as a single-stranded oligonucleotide agent, that includes a nucleotide sequence that is substantially identical to a nucleotide sequence of an miRNA, such as an endogenous miRNA listed in Table 1. An oligonucleotide sequence that is substantially identical to an endogenous miRNA sequence is 70%, 80%, 90%, or more identical to the endogenous miRNA sequence. Preferably, the agent is identical in sequence with an endogenous miRNA. An antagomir that is substantially identical to a nucleotide sequence of an miRNA can be delivered to a cell or a human to replace or supplement the activity of an endogenous miRNA, such as when an miRNA deficiency is linked to a disease or disorder, or aberrant or unwanted expression of the mRNA that is the target of the endogenous miRNA is linked to a disease or disorder. In one embodiment, an antagomir agent featured in the invention can have a nucleotide sequence that is substantially identical to miR-122 (see Table 1). An miR-122 binds to numerous RNAs including aldolase A mRNA, which has been shown to be overexpressed in different cancers, including lung cancer and breast cancer, and is overexpressed in adenocarcinomas of various different tissues origins. Thus a single stranded antagomir that is substantially identical to miR-122 can be administered as a therapeutic composition to a subject having or at risk for developing lung cancer or breast cancer, for example.

An miR-122 binds other mRNAs, including N-myc downstream regulated gene (Ndrg3) mRNA, IQ motif containing GTPase activating protein-1 (Iqgap1) mRNA, HMG-CoA-reductase (Hmgcr) mRNA, and citrate synthase mRNA. Iqgap1 overexpression is associated with gastric cancer and colorectal cancer. Thus a single stranded antagomir that is substantially identical to miR-122 can be useful for down-regulating Iqgap1 expression, and can be administered as a therapeutic composition to a subject having or at risk for developing gastric cancer and colorectal cancer. Hmgcr inhibitors are useful to treat hyperglycemia and to reduce the risk of stroke and bone fractures. Thus a single stranded antagomir that is substantially identical to miR-122 can be useful for downregulating Hmgcr expression, and can be administered as a therapeutic composition to a subject having or at risk for developing hyperglycemia, stroke, or a bone fracture. A single stranded antagomir that is substantially identical to miR-122 can be administered as a therapeutic composition to a subject having or at risk for developing a disorder characterized by the aberrant or unwanted expression of any of these genes, or any other gene downregulated by miR-122.

In one embodiment, an antagomir, such as a single-stranded oligonucleotide agent, can have a nucleotide sequence that is substantially identical to miR-16, miR-192, or miR-194. Single-stranded oligonucleotide agents that are substantially identical to at least a portion of an miRNA, such as those described above, can be administered to a subject to treat the disease or disorder associated with the downregulation of an endogenous miRNA, or the aberrant or unwanted expression of an mRNA target of the endogenous miRNA.

In one aspect, the invention features a method of reducing the levels of an miRNA or pre-miRNA in a cell of a subject, e.g., a human subject. The method includes the step of administering an antagomir to the subject, where the antagomir is substantially single-stranded and includes a sequence that is substantially complementary to 12 to 23 contiguous nucleotides, and preferably 15 to 23 contiguous nucleotides, of a target sequence of an miRNA or pre-miRNA nucleotide sequence. Preferably, the target sequence differs by no more than 1, 2, or 3 nucleotides from a microRNA or pre-microRNA sequence, such as a microRNA sequence shown in Table 1.

The antagomir may be administered into a recipient in a wide variety of ways. Preferred modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter.

In one embodiment, the methods featured in the invention are useful for reducing the level of an endogenous miRNA (e.g., miR-122, miR-16, miR-192 or miR-194) or pre-miRNA in a cell, e.g, in a cell of a subject, such as a human subject. Such methods include contacting the cell with an antagomir, such as a single-stranded oligonucleotide agent, described herein for a time sufficient to allow uptake of the antagomir into the cell.

In another aspect, the invention features a method of making an antagomir, such as a single-stranded oligonucleotide agent, described herein. In one embodiment, the method includes synthesizing an oligonucleotide agent, including incorporating a nucleotide modification that stabilizes the antagomir against nucleolytic degradation.

In another aspect, the invention features a pharmaceutical composition including an antagomir, such as a single-stranded oligonucleotide agent, described herein, and a pharmaceutically acceptable carrier. In a preferred embodiment, the antagomir, such as a single-stranded oligonucleotide agent, included in the pharmaceutical composition hybridizes to miR-122, miR-16, miR-192, or miR-194.

In another aspect the invention features a method of inhibiting miRNA expression (e.g., miR-122, miR-16, miR-192, or miR-194 expression) or pre-miRNA expression in a cell, e.g., a cell of a subject. The method includes contacting the cell with an effective amount of an antagomir, such as a single-stranded oligonucleotide agent, described herein, which is substantially complementary to the nucleotide sequence of the target miRNA or the target pre-miRNA. Such methods can be performed on a mammalian subject by administering to a subject one of the oligonucleotide agents/pharmaceutical compositions described herein.

In another aspect the invention features a method of increasing levels of an RNA or protein that are encoded by a gene whose expression is down-regulated by an miRNA, e.g., an endogenous miRNA, such as miR-122, miR-16, miR-192 or miR-194. The method includes contacting the cell with an effective amount of an antagomir, such as a single-stranded oligonucleotide agent, described herein, which is substantially complementary to the nucleotide sequence of the miRNA that binds to and effectively inhibits translation of the RNA transcribed from the gene. For example, the invention features a method of increasing aldolase A protein levels in a cell. Similarly, the invention features a method of increasing Ndrg3, Iqgap1, Hmgcr, and/or citrate synthase protein levels in a cell. The methods include contacting the cell with an effective amount of an antagomir described herein (e.g., antagomir-122, described in Table 2a-e, Table 4 and Table 7), which is substantially complementary to the nucleotide sequence of miR-122 (see Table 1).

Preferably, an antagomir, such as a single-stranded oligonucleotide agent, (a term which is defined below) will include a ligand that is selected to improve stability, distribution or cellular uptake of the agent. Compositions featured in the invention can include conjugated single-stranded oligonucleotide agents as well as conjugated monomers that are the components of or can be used to make the conjugated oligonucleotide agents. The conjugated oligonucleotide agents can modify gene expression by targeting and binding to a nucleic acid, such as an miRNA (e.g., miR-122, miR-16, miR-192, or miR-194) or pre-miRNA.

In a preferred embodiment, the ligand is a lipophilic moiety, e.g., cholesterol, which enhances entry of the antagomir, such as a single-stranded oligonucleotide agent, into a cell, such as a hepatocyte, synoviocyte, myocyte, keratinocyte, leukocyte, endothelial cell (e.g., a kidney cell), B-cell, T-cell, epithelial cell, mesodermal cell, myeloid cell, neural cell, neoplastic cell, mast cell, or fibroblast cell. In some embodiments, a myocyte is a smooth muscle cell or a cardiac myocyte. A fibroblast cell can be a dermal fibroblast, and a leukocyte can be a monocyte. In another embodiment, the cell is from an adherent tumor cell line derived from a tissue, such as bladder, lung, breast, cervix, colon, pancreas, prostate, kidney, liver, skin, or nervous system (e.g., central nervous system).

In another aspect, the invention provides methods of increasing expression of a target gene by providing an antagomir to which a lipophilic moiety is conjugated, e.g., a lipophilic conjugated antagomir described herein, to a cell. The antagomir preferably hybridizes to an miRNA (e.g., miR-122, miR-16, miR-192, or miR-194) or a pre-miRNA. In a preferred embodiment the conjugated antagomir can be used to increase expression of a target gene in an organism, e.g., a mammal, e.g., a human, or to increase expression of a target gene in a cell line or in cells which are outside an organism. An mRNA transcribed from the target gene hybridizes to an endogenous miRNA, which consequently results in downregulation of mRNA expression. An antagomir, such as a single-stranded oligonucleotide agent, featured in the invention hybridizes to the endogenous miRNA and consequently causes an increase in mRNA expression. In the case of a whole organism, the method can be used to increase expression of a gene and treat a condition associated with a low level of expression of the gene. For example, an antagomir, such as a single-stranded oligonucleotide agent, that targets miR-122 (e.g., antagomir-122) can be used to increase expression of an aldolase A gene to treat a subject having, or at risk for developing, hemolytic anemia, arthrogryposis complex congenita, pituitary ectopia, rhabdomyolysis, hyperkalemia, or any other disorder associated with aldolase A deficiency. Administration of an antagomir, such as a single-stranded oligonucleotide agent, that targets miR-122 (e.g., antagomir-122) can be also be used to increase expression of an Ndrg3, Iqgap1, Hmgcr, or citrate synthase gene to treat a subject having, or at risk for developing, a disorder associated with a decreased expression of any one of these genes.

In another aspect, the invention provides compositions and methods for treating a disease, disorder or condition of the central nervous system. One such disease, disorder or condition of the central nervous system is associated with abnormal expression of a target gene or otherwise an abnormal decreased expression of a target gene when compared with the normal expression of the otherwise identical gene. Such an abnormal decreased expression of a target gene may be the result of a genetic mutation in the gene. Regardless, the term "disease, disorder or condition of the central nervous system" should also be construed to encompass other pathologies in the central nervous system which are not the result of a genetic defect per se in cells of the central nervous system, but rather are the result of infiltration of the central nervous system by cells which do not originate in the central nervous system, for example, metastatic tumor formation in the central nervous system. The term should also be construed to include stroke or trauma to the central nervous system induced by direct injury to the tissues of the central nervous system.

Diseases, disorders or conditions of the CNS also encompasses pathologies including neurodegenerative diseases, spinal cord injury, head trauma or surgery, viral infections that result in tissue, organ, or gland disfunction, and the like. Such neurodegenerative diseases include but are not limited to, AIDS dementia complex; demyelinating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supra-nucleo palsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multi-system disorder; demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Demetia of Lewy body type; Wernicke-Korsakoff syndrome; chronic alcoholism; Creutzfeldt-Jakob disease; Subacute sclerosing panencephalitis hallerrorden-Spatz disease; and Dementia pugilistica.

The invention includes compositions and methods for decreasing miRNA levels in the CNS, preferably the brain of a mammal. By way of a non-limiting example, miR-16 levels can effectively be decreased by local injection of an antagomir directed to miR-16 to a mouse brain. The decrease expression of miR-16 levels in turn can increase expression of a target gene where expression therefrom is inhibited by miR-16. Therefore, an antagimor can effectively increase expression levels of a desired target gene in the CNS of a mammal. In another aspect, the antagimor can effectively increase expression levels of a desired target gene in a cell of the CNS.

In one embodiment, the antagomir, such as a single-stranded oligonucleotide agent, to which a lipophilic moiety is conjugated is used to increase expression of a gene in a cell that is not part of a whole organism, such as when the cell is part of a primary cell line, secondary cell line, tumor cell line, or transformed or immortalized cell line. Cells that are not part of a whole organism can be used in an initial screen to determine if an antagomir, such as a single-stranded oligonucleotide agent, is effective in increasing target gene expression levels, or decreasing levels of a target miRNA or pre-miRNA. A test in cells that are not part of a whole organism can be followed by test of the antagomir in a whole animal. In some embodiments, the antagomir that is conjugated to a lipophilic moiety is administered to an organism, or contacted with a cell that is not part of an organism, in the absence of (or in a reduced amount of) other reagents that facilitate or enhance delivery, e.g., a compound which enhances transit through the cell membrane. (A reduced amount can be an amount of such reagent which is reduced in comparison to what would be needed to get an equal amount of nonconjugated antagomir into the target cell). For example, the antagomir that is conjugated to a lipophilic moiety is administered to an organism, or contacted with a cell that is not part of an organism, in the absence (or reduced amount) of (i) an additional lipophilic moiety; (ii) a transfection agent (e.g., an ion or other substance which substantially alters cell permeability to an oligonucleotide agent); or (iii) a commercial transfecting agent such as Lipofectamine™ (Invitrogen, Carlsbad, Calif.), Lipofectamine 2000™, TransIT-TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

Cationic lipid particles have been used to encapsulate oligonucleotide reagents. For e.g. Cationic lipid saturation influences intracellular delivery of encapsulated nucleic acids. Heyes, James; Palmer, Lorne; Bremner, Kaz; MacLachlan, Ian., Journal of Controlled Release (2005), 107(2), 276-287.

An analogous series of cationic lipids (1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA) and 1,2-dilinolenyloxy-N,N-dimethyl-3-aminopropane (DLenDMA)) possessing 0, 1, 2 or 3 double bonds per alkyl chain resp., was synthesized to det. the correlation between lipid satn., fusogenicity and efficiency of intracellular nucleic acid delivery. 31P-NMR anal. suggests that as satn. increases, from 2 to 0 double bonds, lamellar (L$\alpha$) to reversed hexagonal (HII) phase transition temp. increases, indicating decreasing fusogenicity. This trend is largely reflected by the efficiency of gene silencing observed in vitro when the lipids are formulated as Stable Nucleic Acid Lipid Particles (SNALPs) encapsulating small inhibitory RNA (siRNA). Uptake expts. suggest that despite their lower gene silencing efficiency, the less fusogenic particles are more readily internalized by cells. Microscopic visualization of fluorescently labeled siRNA uptake was supported by quant. data acquired using radiolabeled prepns. Since electrostatic binding is a precursor to uptake, the pKa of each cationic lipid was detd. The results support a transfection model in which endosomal release, mediated by fusion with the endosomal membrane, results in cytoplasmic translocation of the nucleic acid payload.

In a preferred embodiment, the antagomir is suitable for delivery to a cell in vivo, e.g., to a cell in an organism. In another embodiment, the antagomir is suitable for delivery to a cell in vitro, e.g., to a cell in a cell line.

An antagomir to which a lipophilic moiety is attached can target any miRNA (e.g., miR-122, miR-16, miR-192, or miR-194) or pre-miRNA described herein and can be delivered to any cell type described herein, e.g., a cell type in an organism, tissue, or cell line. Delivery of the antagomir can be in vivo, e.g., to a cell in an organism, or in vitro, e.g., to a cell in a cell line.

In another aspect, the invention provides compositions including single-stranded oligonucleotide agents described herein, and in particular, compositions including an antagomir to which a lipophilic moiety is conjugated, e.g., a lipophilic conjugated antagomir that hybridizes to miR-122, miR-16, miR-192, or miR-194. In a preferred embodiment the composition is a pharmaceutically acceptable composition.

In one embodiment the composition is suitable for delivery to a cell in vivo, e.g., to a cell in an organism. In another aspect, the antagomir is suitable for delivery to a cell in vitro, e.g., to a cell in a cell line.

An "antagomir" or "oligonucleotide agent" of the present invention referes to a single stranded, double stranded or partially double stranded oligomer or polymer of ribonucleic acid (RNA) or deoxyribonucleic acid (DNA) or both or modifications thereof, which is antisense with respect to its target. This term includes oligonucleotides composed of naturally-occurring nucleobases, sugars and covalent internucleoside (backbone) linkages and which contain at least one non-naturally-occurring portions which function similarly. Such modified or substituted oligonucleotides are preferred over native forms because of desirable properties such as, for example, enhanced cellular uptake, enhanced affinity for nucleic acid target and increased stability in the presence of nucleases. In a preferred embodiment, the antagomir does not include a sense strand, and in another preferred embodiment, the antagomir does not self-hybridize to a significant extent. An antagomir featured in the invention can have secondary structure, but it is substantially single-stranded under physiological conditions. An antagomir that is substantially single-stranded is single-stranded to the extent that less than about 50% (e.g., less than about 40%, 30%, 20%, 10%, or 5%) of the antagomir is duplexed with itself. FIGS. 5-11 provides representative structures of antagomirs.

"Substantially complementary" means that two sequences are substantially complementary that a duplex can be formed between them. The duplex may have one or more mismatches but the region of duplex formation is sufficient to down-regulate expression of the target nucleic acid. The region of substantial complementarity can be perfectly paired. In other embodiments, there will be nucleotide mismatches in the region of substantial complementarity. In a preferred embodiment, the region of substantial complementarity will have no more than 1, 2, 3, 4, or 5 mismatches.

The antagomirs featured in the invention include oligomers or polymers of ribonucleic acid (RNA) or deoxyribonucleic acid (DNA) or both or modifications thereof. This term includes oligonucleotides composed of naturally occurring nucleobases, sugars, and covalent internucleoside (backbone) linkages as well as oligonucleotides having non-naturally-occurring portions that function similarly. Such modified or substituted oligonucleotides are often preferred over native forms because of desirable properties such as, for example, enhanced cellular uptake, enhanced affinity for nucleic acid target, and/or increased stability in the presence of nucleases. The oligonucleotide agents can be about 12 to about 30 nucleotides long, e.g., about 15 to about 25, or about 18 to about 25 nucleotides long (e.g., about 19, 20, 21, 22, 23, 24 nucleotides long).

The antagomirs featured in the invention can target RNA, e.g., an endogenous pre-miRNA or miRNA of the subject or an endogenous pre-miRNA or miRNA of a pathogen of the subject. For example, the oligonucleotide agents can target an miRNA of the subject, such as miR-122, miR-16, miR-192, or miR-194. Such single-stranded oligonucleotide can be useful for the treatment of diseases involving biological processes that are regulated by miRNAs, including developmental timing, differentiation, apoptosis, cell proliferation, organ development, and metabolism.

MicroRNA-Type Oligonucleotide Agents

The antagomir featured in the invention include microRNA-type (miRNA-type) oligonucleotide agents, e.g., the miRNA-type oligonucleotide agents listed in Table 2a-f. MicroRNAs are small noncoding RNA molecules that are capable of causing post-transcriptional silencing of specific genes in cells such as by the inhibition of translation or through degradation of the targeted mRNA. An miRNA can be completely complementary or can have a region of non-complementarity with a target nucleic acid, consequently resulting in a "bulge" at the region of non-complementarity. The region of noncomplementarity (the bulge) can be flanked by regions of sufficient complementarity, preferably complete complementarity to allow duplex formation. Preferably, the regions of complementarity are at least 8, 9, or 10 nucleotides long. An miRNA can inhibit gene expression by repressing translation, such as when the microRNA is not completely complementary to the target nucleic acid; or by causing target RNA degradation, which is believed to occur only when the miRNA binds its target with perfect complementarity. The invention also can include double-stranded precursors of miRNAs that may or may not form a bulge when bound to their targets.

An miRNA or pre-miRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors typically have a length of about 70-100 nucleotides and have a hairpin conformation. MicroRNAs are generated in vivo from pre-miRNAs by the enzymes Dicer and Drosha, which specifically process long pre-miRNA into functional miRNA. The miRNA-type oligonucleotide agents, or pre-miRNA-type oligonucleotide agents featured in the invention can be synthesized in vivo by a cell-based, system or in vitro by chemical synthesis. MicroRNA-type oligonucleotide agents can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism. Modifications can also increase sequence specificity, and consequently decrease off-site targeting. Methods of synthesis and chemical modifications are described in greater detail below.

Given a sense strand sequence (e.g., the sequence of a sense strand of a cDNA molecule), an miRNA-type antagomir can be designed according to the rules of Watson and Crick base pairing. The miRNA-type antagomir can be complementary to a portion of an RNA, e.g., an miRNA, pre-miRNA, or mRNA. For example, the miRNA-type antagomir can be complementary to an miRNA endogenous to a cell, such as miR-122, miR-16, miR-192, or miR-194. An miRNA-type antagomir can be, for example, from about 12 to 30 nucleotides in length, preferably about 15 to 28 nucleotides in length (e.g., 16, 17, 18, 19, 20, 21, 22, 23, 24, 25, 26, or 27 nucleotides in length).

Based on the present disclosure, the length of the antagimor can contribute to the biochemical function of the antagimor with respect to its ability to decrease the expression levels of a desired miRNA. In some instances, antagomirs may require at least 19 nucleotides in length for optimal function.

In particular, an miRNA-type antagomir featured in the invention can have a chemical modification on a nucleotide in an internal (i.e., non-terminal) region having noncomplementarity with the target nucleic acid. For example, a modified nucleotide can be incorporated into the region of an miRNA that forms a bulge. The modification can include a ligand attached to the miRNA, e.g., by a linker. The modification can, for example, improve pharmacokinetics or stability of a therapeutic miRNA-type oligonucleotide agent, or improve hybridization properties (e.g., hybridization thermodynamics) of the miRNA-type antagomir to a target nucleic acid. In some embodiments, it is preferred that the orientation of a modification or ligand incorporated into or tethered to the bulge region of an miRNA-type antagomir is oriented to occupy the space in the bulge region. For example, the modification can include a modified base or sugar on the nucleic acid strand or a ligand that functions as an intercalator. These are preferably located in the bulge. The intercalator can be an aromatic, e.g., a polycyclic aromatic or heterocyclic aromatic compound. A polycyclic intercalator can have stacking capabilities, and can include systems with 2, 3, or 4 fused rings. The universal bases described below can be incorporated into the miRNA-type oligonucleotide agents. In some embodiments, it is preferred that the orientation of a modification or ligand incorporated into or tethered to the bulge region of an miRNA-type antagomir is oriented to occupy the space in the bulge region. This orientation facilitates the improved hybridization properties or an otherwise desired characteristic of the miRNA-type oligonucleotide agent.

In one embodiment, an miRNA-type antagomir or a pre-miRNA can include an aminoglycoside ligand, which can cause the miRNA-type antagomir to have improved hybridization properties or improved sequence specificity. Exemplary aminoglycosides include glycosylated polylysine; galactosylated polylysine; neomycin B; tobramycin; kanamycin A; and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. In some embodiments the guanidine analog (the guanidinoglycoside) of an aminoglycoside ligand is tethered to an oligonucleotide agent. In a guanidinoglycoside, the amine group on the amino acid is exchanged for a guanidine group. Attachment of a guanidine analog can enhance cell permeability of an oligonucleotide agent.

In one embodiment, the ligand can include a cleaving group that contributes to target gene inhibition by cleavage of the target nucleic acid. Preferably, the cleaving group is tethered to the miRNA-type antagomir in a manner such that it is positioned in the bulge region, where it can access and cleave the target RNA. The cleaving group can be, for example, a bleomycin (e.g., bleomycin-$A_5$, bleomycin-$A_2$, or bleomycin-$B_2$), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to an miRNA or a pre-miRNA to promote cleavage of the target RNA, e.g., at the bulge region. For example, 1,8-dimethyl-1,3,6,8,10,13-hexaazacyclotetradecane(cyclam) can be conjugated to a peptide (e.g., by an amino acid derivative) to promote target RNA cleavage. The methods and compositions featured in the invention include miRNA-type oligonucleotide agents that inhibit target gene expression by a cleavage or non-cleavage dependent mechanism.

An miRNA-type antagomir or pre-miRNA-type antagomir can be designed and synthesized to include a region of non-complementarity (e.g., a region that is 3, 4, 5, or 6 nucleotides long) flanked by regions of sufficient complementarity to form a duplex (e.g., regions that are 7, 8, 9, 10, or 11 nucleotides long) with a target RNA, e.g., an miRNA, such as miR-122, miR-16, miR-192, or miR-194.

For increased nuclease resistance and/or binding affinity to the target, the single-stranded oligonucleotide agents featured in the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to the target. The inclusion of pyranose sugars in the oligonucleotide backbone can also decrease endonucleolytic cleavage. An antagomir can be further modified by including a 3' cationic group, or by inverting the nucleoside at the terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

With respect to phosphorothioate linkages that serve to increase protection against RNase activity, the antagomir can include a phosphorothioate at least the first, second, or third internucleotide linkage at the 5' or 3' end of the nucleotide sequence. In one embodiment, the antagomir includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In a preferred embodiment, the antagomir includes at least one 2'-O-methyl-modified nucleotide, and in some embodiments, all of the nucleotides of the antagomir include a 2'-O-methyl modification. In yet another the preferred embodiment, the antagomir includes six phosphorothioate backbone modifications; two phosphorothioates are located at the 5'-end and four at the 3'-end.

The 5'-terminus can be blocked with an aminoalkyl group, e.g., a 5'-O-alkylamino substituent. Other 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5' end of the oligonucleotide. Even small alkyl chains, aryl groups, or heterocyclic conjugates or modified sugars (D-ribose, deoxyribose, glucose etc.) can block 3'-5'-exonucleases.

In one embodiment, an antagomir, such as a single-stranded oligonucleotide agent, includes a modification that improves targeting, e.g. a targeting modification described herein. Examples of modifications that target single-stranded oligonucleotide agents to particular cell types include carbohydrate sugars such as galactose, N-acetylgalactosamine, mannose; vitamins such as folates; other ligands such as RGDs and RGD mimics; and small molecules including naproxen, ibuprofen or other known protein-binding molecules.

An antagomir, such as a single-stranded oligonucleotide agent, featured in the invention can be constructed using chemical synthesis and/or enzymatic ligation reactions using procedures known in the art. For example, an antagomir can be chemically synthesized using naturally occurring nucleotides or variously modified nucleotides designed to increase the biological stability of the molecules or to increase the physical stability of the duplex formed between the antagomir and target nucleic acids, e.g., phosphorothioate derivatives and acridine substituted nucleotides can be used. Other appropriate nucleic acid modifications are described herein. Alternatively, the antagomir can be produced biologically using an expression vector into which a nucleic acid has been subcloned in an antisense orientation (i.e., RNA transcribed from the inserted nucleic acid will be of an antisense orientation to a target nucleic acid of interest (e.g., an miRNA or pre-miRNA)).

Chemical Definitions

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —NH(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a R$_3$SiO-radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic,or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl, and decalin.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic,or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, SO$_3$H, sulfate, phosphate, perfluoroalkyl, perfluoroalkoxy, methylenedioxy, ethylenedioxy, carboxyl, oxo, thioxo, imino (alkyl, aryl, aralkyl), S(O)$_n$alkyl (where n is 0-2), S(O)$_n$ aryl (where n is 0-2), S(O)$_n$ heteroaryl (where n is 0-2), S(O)$_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

Antagomir Structure

An antagomir, such as a single-stranded oligonucleotide agent, featured in the invention includes a region sufficient complementarity to the target nucleic acid (e.g., target miRNA, pre-miRNA or mRNA), and is of sufficient length in terms of nucleotides, such that the antagomir forms a duplex with the target nucleic acid. The antagomir can modulate the function of the targeted molecule. For example, when the targeted molecule is an miRNA, such as miR-122, miR-16, miR-192, or miR-194, the antagomir can inhibit the gene silencing activity of the target miRNA, which action will up-regulate expression of the mRNA targeted by the target miRNA. When the target is an mRNA, the antagomir can replace or supplement the gene silencing activity of an endogenous miRNA.

For ease of exposition the term nucleotide or ribonucleotide is sometimes used herein in reference to one or more monomeric subunits of an oligonucleotide agent. It will be understood herein that the usage of the term "ribonucleotide" or "nucleotide" herein can, in the case of a modified RNA or nucleotide surrogate, also refer to a modified nucleotide, or surrogate replacement moiety at one or more positions.

An antagomir featured in the invention is, or includes, a region that is at least partially, and in some embodiments fully, complementary to the target RNA. It is not necessary that there be perfect complementarity between the antagomir and the target, but the correspondence must be sufficient to enable the oligonucleotide agent, or a cleavage product thereof, to modulate (e.g., inhibit) target gene expression.

An antagomir will preferably have one or more of the following properties:
(1) it will be of the Formula 1, 2, 3, or 4 described below;
(2) it will have a 5' modification that includes one or more phosphate groups or one or more analogs of a phosphate group;
(3) it will, despite modifications, even to a very large number of bases specifically base pair and form a duplex structure with a homologous target RNA of sufficient thermodynamic stability to allow modulation of the activity of the targeted RNA;
(4) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, all of the nucleotide sugars can contain e.g., 2'OMe, 2' fluoro in place of 2' hydroxyl. This deoxyribonucleotide-containing agent can still be expected to exhibit RNA-like properties. While not wishing to be bound by theory, an electronegative fluorine prefers an axial orientation when attached to the C2' position of ribose. This spatial preference of fluorine can, in turn, force the sugars to adopt a $C_3$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into hydrogen-bonding which is more characteristic of the 2'-OH moiety of a ribonucleotide than the 2'-H moiety of a deoxyribonucleotide. A preferred antagomir will: exhibit a $C_3$-endo pucker in all, or at least 50, 75, 80, 85, 90, or 95% of its sugars; exhibit a $C_3$-endo pucker in a sufficient amount of its sugars that it can give rise to a the RNA-characteristic A-family-type helix; will have no more than 20, 10, 5, 4, 3, 2, or 1 sugar which is not a $C_3$-endo pucker structure.

Preferred 2'-modifications with C3'-endo sugar pucker include:
2'-OH, 2'-O—Me, 2'-O-methoxyethyl, 2'-O-aminopropyl, 2'-F, 2'-O—CH2CO—NHMe, 2'-O—CH2-CH2-O—CH2-CH2-N(Me)2, and LNA.

Preferred 2'-modifications with a C2'-endo sugar pucker include:
2'-H, 2'-Me, 2'-S—Me, 2'-Ethynyl, 2'-ara-F.

Sugar modifications can also include L-sugars and 2'-5'-linked sugars.

As used herein, "specifically hybridizable" and "complementary" are terms that are used to indicate a sufficient degree of complementarity such that stable and specific binding occurs between an antagomir of the invention and a target RNA molecule, e.g., an miRNA or a pre-miRNA. Specific binding requires a sufficient lack of complementarity to non-target sequences under conditions in which specific binding is desired, i.e., under physiological conditions in the case of in vivo assays or therapeutic treatment, or in the case of in vitro assays, under conditions in which the assays are performed. It has been shown that a single mismatch between targeted and non-targeted sequences are sufficient to provide discrimination for siRNA targeting of an mRNA (Brummelkamp et al., *Cancer Cell*, 2002, 2:243).

In one embodiment, an antagomir is "sufficiently complementary" to a target RNA, such that the antagomir inhibits production of protein encoded by the target mRNA. The target RNA can be, e.g., a pre-mRNA, mRNA, or miRNA endogenous to the subject. In another embodiment, the antagomir is "exactly complementary" (excluding the SRMS containing subunit(s)) to a target RNA, e.g., the target RNA and the antagomir can anneal to form a hybrid made exclusively of Watson-Crick base pairs in the region of exact complementarity. A "sufficiently complementary" target RNA can include a region (e.g., of at least 7 nucleotides) that is exactly complementary to a target RNA. Moreover, in some embodiments, the antagomir specifically discriminates a single-nucleotide difference. In this case, the antagomir only down-regulates gene expression if exact complementarity is found in the region of the single-nucleotide difference.

Oligonucleotide agents discussed herein include otherwise unmodified RNA and DNA as well as RNA and DNA that have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al. (*Nucleic Acids Res.*, 1994, 22:2183-2196). Such rare or unusual RNAs, often termed modified RNAs, are typically the result of a post-transcriptional modification and are within the term unmodified RNA as used herein. Modified RNA, as used herein, refers to a molecule in which one or more of the components of the nucleic acid, namely sugars, bases, and phosphate moieties, are different from that which occur in nature, preferably different from that which occurs in the human body. While they are referred to as "modified RNAs" they will of course, because of the modification, include molecules that are not, strictly speaking, RNAs. Nucleoside surrogates are molecules in which the ribophosphate backbone is replaced with a non-ribophosphate construct that allows the bases to be presented in the correct spatial relationship such that hybridization is substantially similar to what is seen with a ribophosphate backbone, e.g., non-charged mimics of the ribophosphate backbone. Examples of all of the above are discussed herein.

As nucleic acids are polymers of subunits or monomers, many of the modifications described below occur at a position which is repeated within a nucleic acid, e.g., a modification of a base, or a phosphate moiety, or a non-linking O of a phosphate moiety. In some cases the modification will occur at all of the subject positions in the nucleic acid but in many, and in fact in most cases it will not. By way of example, a modification may only occur at a 3' or 5' terminal position, in a terminal region, e.g., at a position on a terminal nucleotide, or in the last 2, 3, 4, 5, or 10 nucleotides of a strand. The ligand can be attached at the 3' end, the 5' end, or at an internal position, or at a combination of these positions. For example, the ligand can be at the 3' end and the 5' end; at the 3' end and at one or more internal positions; at the 5' end and at one or more internal positions; or at the 3' end, the 5' end, and at one or more internal positions. For example, a phosphorothioate modification at a non-linking O position may only occur at one or both termini, or may only occur in a terminal region, e.g., at a position on a terminal nucleotide or in the last 2, 3, 4, 5, or 10 nucleotides of the oligonucleotide. The 5' end can be phosphorylated.

Modifications and nucleotide surrogates are discussed below.

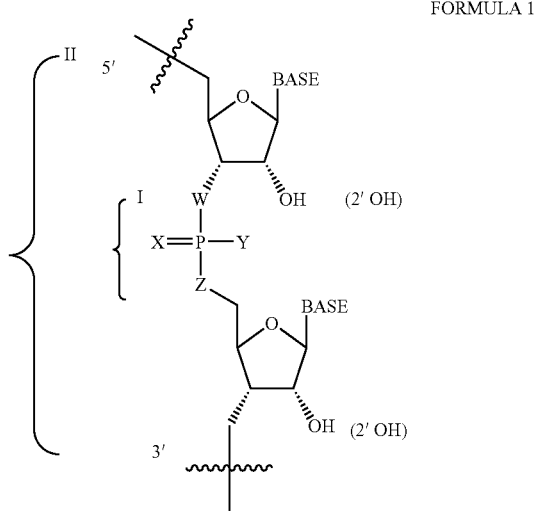

FORMULA 1

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, for example, can render oligoribonucleotides more stable to nucleases. Unmodified oligoribonucleotides may also be less than optimal in terms of offering tethering points for attaching ligands or other moieties to an oligonucleotide agent.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein);

(ii) alteration, e.g., replacement, of a constituent of the ribose sugar, e.g., of the 2' hydroxyl on the ribose sugar, or wholesale replacement of the ribose sugar with a structure other than ribose, e.g., as described herein;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, such as a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid but rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-linking oxygen atoms (i.e., X and Y in Formula 1 above). However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g., phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is preferred.

The phosphate linker can also be modified by replacement of a linking oxygen (i.e., W or Z in Formula 1) with nitrogen (bridged phosphoroamidates), sulfur (bridged phosphorothioates) and carbon (bridged methylenephosphonates). The replacement can occur at a terminal oxygen (position W (3') or position Z (5')). Replacement of W with carbon or Z with nitrogen is preferred.

Candidate agents can be evaluated for suitability as described below.

The Sugar Group

A modified RNA can include modification of all or some of the sugar groups of the ribonucleic acid. For example, the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is e.g., by a methylene bridge or ethylene bridge (e.g., 2'-4'-ethylene bridged nucleic acid (ENA)), to the 4' carbon of the same ribose sugar; amino, O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity (an SRMS) at one or more sites in the oligonucleotide agent.

Candidate modifications can be evaluated as described below.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide—mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —$(CH_2)_n$—, —$(CH_2)_n$N—, —$(CH_2)_nO$—, —$(CH_2)_nS$—, $O(CH_2CH_2O)_n$ $CH_2CH_2OH$ (e.g., n=3 or 6), abasic sugars, amide, carboxy, amine, oxyamine, oxyimine, thioether, disulfide, thiourea, sulfonamide, or morpholino, or biotin and fluorescein reagents. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine)and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+complexes of tetraazamacrocycles).

Terminal modifications can be added for a number of reasons, including as discussed elsewhere herein to modulate activity or to modulate resistance to degradation. Preferred modifications include the addition of a methylphosphonate at the 3'-most terminal linkage; a 3' C5-aminoalkyl-dT; 3' cationic group; or another 3' conjugate to inhibit 3'-5' exonucleolytic degradation.

Terminal modifications useful for modulating activity include modification of the 5' end with phosphate or phosphate analogs. E.g., in preferred embodiments oligonucleotide agents are 5' phosphorylated or include a phosphoryl analog at the 5' terminus. 5'-phosphate modifications include those which are compatible with RISC mediated gene silencing. Suitable modifications include: 5'-monophosphate ((HO)2(O)P—O-5'); 5'-diphosphate ((HO)2(O)P—O—P (HO)(O)—O-5'); 5'-triphosphate ((HO)2(O)P—O—(HO) (O)P—O—P(HO)(O)—O-5'); 5'guanosine cap (7-methylated or non-methylated) (7m-G-O-5'-(HO)(O)P—O—(HO) (O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS) (S)P—O-5'), 5'-phosphorothiolate ((HO)2(O)P—S-5'); any additional combination of oxgen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-).

Terminal modifications can also be useful for monitoring distribution, and in such cases the preferred groups to be added include fluorophores, e.g., fluorscein or an Alexa dye, e.g., Alexa 488. Terminal modifications can also be useful for enhancing uptake, useful modifications for this include cholesterol. Terminal modifications can also be useful for cross-linking anantagomir to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil(pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyl adenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Candidate modifications can be evaluated as described below.

Evaluation of Candidate Oligonucleotide Agents

One can evaluate a candidate single-stranded oligonucleotide agent, e.g., a modified candidate single-stranded oligonucleotide agent, for a selected property by exposing the agent or modified molecule and a control molecule to the appropriate conditions and evaluating for the presence of the selected property. For example, resistance to a degradent can be evaluated as follows. A candidate modified antagomir (and preferably a control single-stranded oligonucleotide agent, usually the unmodified form) can be exposed to degradative conditions, e.g., exposed to a milieu, which includes a degradative agent, e.g., a nuclease. For example, one can use a biological sample, e.g., one that is similar to a milieu, which might be encountered, in therapeutic use, e.g., blood or a cellular fraction, e.g., a cell-free homogenate or disrupted cells. The candidate and control can then be evaluated for resistance to degradation by any of a number of approaches. For example, the candidate and control could be labeled, preferably prior to exposure, with, e.g., a radioactive or enzymatic label, or a fluorescent label, such as Cy3 or Cy5. Control and modified oligonucleotide agents can be incubated with the degradative agent, and optionally a control, e.g., an inactivated, e.g., heat inactivated, degradative agent. A physical parameter, e.g., size, of the modified and control molecules are then determined. They can be determined by a physical method, e.g., by polyacrylamide gel electrophoresis or a sizing column, to assess whether the molecule has maintained its original length, or assessed functionally. Alternatively, Northern blot analysis can be used to assay the length of an unlabeled modified molecule.

A functional assay can also be used to evaluate the candidate agent. A functional assay can be applied initially or after an earlier non-functional assay, (e.g., assay for resistance to degradation) to determine if the modification alters the ability of the molecule to inhibit gene expression. For example, a cell, e.g., a mammalian cell, such as a mouse or human cell, can be co-transfected with a plasmid expressing a fluorescent protein, e.g., GFP, and a candidate antagomir homologous to the transcript encoding the fluorescent protein (see, e.g., WO 00/44914). For example, a modified antagomir homologous to the GFP mRNA can be assayed for the ability to inhibit GFP expression by monitoring for a decrease in cell fluorescence, as compared to a control cell, in which the transfection did not include the candidate oligonucleotide agent, e.g., controls with no agent added and/or controls with a non-modified RNA added. Efficacy of the candidate agent on gene expression can be assessed by comparing cell fluorescence in the presence of the modified and unmodified oligonucleotide agent.

In an alternative functional assay, a candidate antagomir homologous to an endogenous mouse gene, preferably a maternally expressed gene, such as c-mos, can be injected into an immature mouse oocyte to assess the ability of the agent to inhibit gene expression in vivo (see, e.g., WO 01/36646). A phenotype of the oocyte, e.g., the ability to maintain arrest in metaphase II, can be monitored as an indicator that the agent is inhibiting expression. For example, cleavage of c-mos mRNA by an antagomir would cause the oocyte to exit metaphase arrest and initiate parthenogenetic development (Colledge et al. Nature 370: 65-68, 1994; Hashimoto et al. Nature, 370:68-71, 1994). The effect of the modified agent on target RNA levels can be verified by Northern blot to assay for a decrease in the level of target RNA, or by Western blot to assay for a decrease in the level of target protein, as compared to a negative control. Controls can include cells in which with no agent is added and/or cells in which a non-modified RNA is added.

Preferred Oligonucleotide Agents

Preferred single-stranded oligonucleotide agents have the following structure (see Formula 2 below):

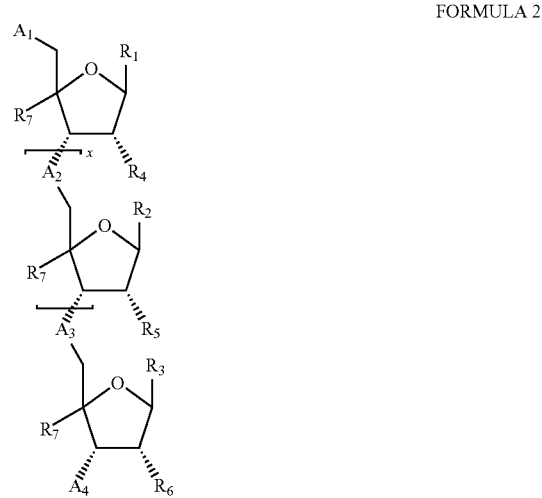

FORMULA 2

Referring to Formula 2 above, $R^1$, $R^2$, and $R^3$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl) uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine,7-deazaadenine, 7-deazaguanine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

$R^4$, $R^5$, and $R^6$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_m CH_2CH_2NHR^9$; $NHC(O)R^8$; cyano; mercapto, $SR^8$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkyl carbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido; or $R^4$, $R^5$, or $R^6$ together combine with $R^7$ to form an [—O—$CH_2$—] covalently bound bridge between the sugar 2' and 4' carbons.

$A^1$ is:

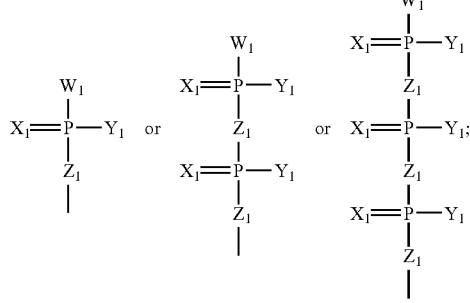

H; OH; $OCH_3$; $W^1$; an abasic nucleotide; or absent;

(a preferred A1, especially with regard to anti-sense strands, is chosen from 5'-monophosphate ($(HO)_2(O)P$—O-5'), 5'-diphosphate ($(HO)_2(O)P$—O—$P(HO)(O)$—O-5'), 5'-triphosphate ($(HO)_2(O)P$—O—$(HO)(O)P$—O—$P(HO)(O)$—O-5'), 5'-guanosine cap (7-methylated or non-methylated) (7m-G-O-5'-$(HO)(O)P$—O—$(HO)(O)P$—O—$P(HO)(O)$—O-5'), 5'-adenosine cap (Appp), and any modified or unmodified nucleotide cap structure (N—O-5'-$(HO)(O)P$—O—$(HO)(O)P$—O—$P(HO)(O)$—O-5'), 5'-monothiophosphate (phosphorothioate; $(HO)_2(S)P$—O-5'), 5'-monodithiophosphate (phosphorodithioate; $(HO)(HS)(S)P$—O-5'), 5'-phosphorothiolate ($(HO)_2(O)P$—S-5'); any additional combination of oxgen/sulfur replaced monophosphate, diphosphate and triphosphates (e.g. 5'-alpha-thiotriphosphate, 5'-gamma-thiotriphosphate, etc.), 5'-phosphoramidates ($(HO)_2(O)P$—NH-5', $(HO)(NH_2)(O)P$—O-5'), 5'-alkylphosphonates (R=alkyl=methyl, ethyl, isopropyl, propyl, etc., e.g. $RP(OH)(O)$—O-5'-, $(OH)_2(O)P$-5'-$CH_2$—), 5'-alkyletherphosphonates (R=alkylether=methoxymethyl ($MeOCH_2$—), ethoxymethyl, etc., e.g. $RP(OH)(O)$—O-5'-)).

$A^2$ is:

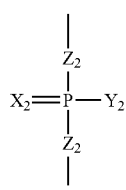

$A^3$ is:

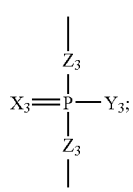

and $A^4$ is:

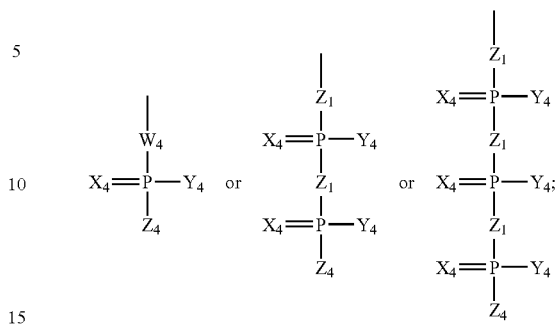

H; $Z^4$; an inverted nucleotide; an abasic nucleotide; or absent.

$W^1$ is OH, $(CH_2)_nR^{10}$, $(CH_2)_nNHR^{10}$, $(CH_2)_nOR^{10}$, $(CH_2)_n SR^{10}$; $O(CH_{2n}R^{10}$; $O(CH_2)_nOR^{10}$, $O(CH_2)_nNR^{10}$, $O(CH_2)_nSR^{10}$; $O(CH_2)_nSS(CH_2)_nOR^{10}$, $O(CH_2)_nC(O)OR^{10}$, $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}O(CH_2CH_2O)_mCH_2CH_2OR^{10}$; $O(CH_2CH_2O)_mCH_2CH_2NHR^{10}$, $NH(CH_2CH_2NH)_mCH_2CH_2NHR^{10}$; Q-$R^{10}$, O-Q-$R^{10}$N-Q-$R^{10}$, S-Q-$R^{10}$ or —O—. $W^4$ is O, $CH_2$, NH, or S.

$X^1$, $X^2$, $X^3$, and $X^4$ are each, independently, O or S.

$Y^1$, $Y^2$, $Y^3$, and $Y^4$ are each, independently, OH, $O^-$, $OR^8$, S, Se, $BH_3^-$, H, $NHR^9$, $N(R^9)_2$ alkyl, cycloalkyl, aralkyl, aryl, or heteroaryl, each of which may be optionally substituted.

$Z^1$, $Z^2$, and $Z^3$ are each independently O, $CH_2$, NH, or S. $Z^4$ is OH, $(CH_2)_nR^{10}$, $(CH_2)_nNHR^{10}$, $(CH_2)_nOR^{10}$, $(CH_2)_nSR^{10}$; $O(CH_2)_nR^{10}$; $O(CH_2)_nOR^{10}$, $O(CH_2)_nNR^{10}$, $O(CH_2)_nSR^{10}$, $O(CH_2)_nSS(CH_2)_nOR^{10}$, $O(CH_2)_nC(O)OR^{10}$; $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}$ $O(CH_2CH_2O)_mCH_2CH_2OR^{10}$, $O(CH_2CH_2O)_mCH_2CH_2NHR^{10}$, $NH(CH_2CH_2NH)_mCH_2CH_2NHR^{10}$; Q-$R^{10}$, O-Q-$R^{10}$N-Q-$R^{10}$, S-Q-$R^{10}$.

X is 5-100, chosen to comply with a length for an antagomir described herein.

$R^7$ is H; or is together combined with $R^4$, $R^5$, or $R^6$ to form an [—O—$CH_2$—] covalently bound bridge between the sugar 2' and 4' carbons.

$R^8$ is alkyl, cycloalkyl, aryl, aralkyl, heterocyclyl, heteroaryl, amino acid, or sugar; $R^9$ is $NH_2$, alkylamino, dialkylamino, heterocyclyl, arylamino, diaryl amino, heteroaryl amino, diheteroaryl amino, or amino acid; and $R^{10}$ is H; fluorophore (pyrene, TAMRA, fluorescein, Cy3 or Cy5 dyes); sulfur, silicon, boron or ester protecting group; intercalating agents (e.g. acridines), cross-linkers (e.g. psoralene, mitomycin C), porphyrins (TPPC4,texaphyrin, Sapphyrin), polycyclic aromatic hydrocarbons (e.g., phenazine, dihydrophenazine), artificial endonucleases (e.g. EDTA), lipophilic carriers (cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid,myristic acid, O3-(oleoyDlithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino; alkyl, cycloalkyl, aryl, aralkyl, heteroaryl; radiolabelled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles); or an oligonucleotide agent. M is 0-1,000,000, and n is 0-20. Q is a spacer selected from the group consisting of abasic sugar, amide, carboxy, oxyamine, oxyimine, thioether, disulfide, thiourea, sulfonamide, or morpholino, biotin or fluorescein reagents.

Preferred oligonucleotide agents in which the entire phosphate group has been replaced have the following structure (see Formula 3 below):

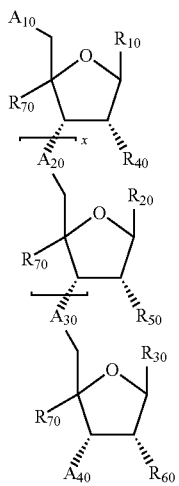

FORMULA 3

Referring to Formula 3, $A^{10}$-$A^{40}$ is L-G-L; $A^{10}$ and/or $A^{40}$ may be absent, in which L is a linker, wherein one or both L may be present or absent and is selected from the group consisting of $CH_2(CH_2)_g$; $N(CH_2)_g$; $O(CH_2)_g$; $S(CH_2)_g$. G is a functional group selected from the group consisting of siloxane, carbonate, carboxymethyl, carbamate, amide, thioether, ethylene oxide linker, sulfonate, sulfonamide, thioformacetal, formacetal, oxime, methyleneimino, methyl enemethylimino, methylenehydrazo, methylenedimethylhydrazo and methyleneoxymethylimino.

$R^{10}$, $R^{20}$, and $R^{30}$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine,7-deazaadenine, 7-deazaguanine, N6, N6-dimethyladenine, 2,6-diaminopurine, 5-amino-allyl-uracil, N3-methyluracil substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

$R^{40}$, $R^{50}$, and $R^{60}$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2R^9$; $NHC(O)R^8$; cyano; mercapto, $SR^7$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, acylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, and ureido groups; or $R^{40}$, $R^{50}$, or $R^{60}$ together combine with $R^{70}$ to form an [—O—$CH_2$—] covalently bound bridge between the sugar 2' and 4' carbons.

X is 5-100 or chosen to comply with a length for an antagomir described herein.

$R^{70}$ is H; or is together combined with $R^{40}$, $R^{50}$, or $R^{60}$ to form an [—O—$CH_2$—] covalently bound bridge between the sugar 2' and 4' carbons.

$R^8$ is alkyl, cycloalkyl, aryl, aralkyl, heterocyclyl, heteroaryl, amino acid, or sugar; and $R^9$ is $NH_2$, alkylamino, dialkylamino, heterocyclyl, arylamino, diaryl amino, heteroaryl amino, diheteroaryl amino, or amino acid. M is 0-1,000,000, n is 0-20, and g is 0-2.

Preferred nucleoside surrogates have the following structure (see Formula 4 below):

FORMULA 4

S is a nucleoside surrogate selected from the group consisting of mophilino, cyclobutyl, pyrrolidine and peptide nucleic acid. L is a linker and is selected from the group consisting of $CH_2(CH_2)_g$; $N(CH_2)_g$; $O(CH_2)_g$; $S(CH_2)_g$; —$C(O)(CH_2)_n$— or may be absent. M is an amide bond; sulfonamide; sulfinate; phosphate group; modified phosphate group as described herein; or may be absent.

$R^{100}$, $R^{200}$, and $R^{300}$ are each, independently, H (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil(pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1, 2, 4,-triazoles, 2-pyridinones, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

X is 5-100, or chosen to comply with a length for an antagomir described herein; and g is 0-2.

An antagomir can include an internucleotide linkage (e.g., the chiral phosphorothioate linkage) useful for increasing nuclease resistance. In addition, or in the alternative, an antagomir can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An antagomir can include ligand-conjugated monomer subunits and monomers for oligonucleotide synthesis. Exemplary monomers are described in co-owned U.S. application Ser. No. 10/916,185, filed on Aug. 10, 2004.

An antagomir can have a ZXY structure, such as is described in co-owned PCT Application No. PCT/US2004/07070 filed on Mar. 8, 2004.

An antagomir can be complexed with an amphipathic moiety. Exemplary amphipathic moieties for use with oligonucleotide agents are described in co-owned PCT Application No. PCT/US2004/07070 filed on Mar. 8, 2004.

In another embodiment, the antagomir can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. oligonucleotide agents complexed to a delivery agent are described in co-owned PCT Application No. PCT/US2004/07070 filed on Mar. 8, 2004.

Enhanced Nuclease Resistance

An antagomir, such as a single-stranded oligonucleotide agent, featured in the invention can have enhanced resistance to nucleases.

For increased nuclease resistance and/or binding affinity to the target, an oligonucleotide agent, e.g., the oligonucleotide agent, can include, for example, 2'-modified ribose units and/or phosphorothioate linkages. E.g., the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; amine, O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

Preferred substitutents are 2'-methoxyethyl, 2'OCH3, 2'-O-allyl, 2'-C-allyl, and 2'-fluoro.

One way to increase resistance is to identify cleavage sites and modify such sites to inhibit cleavage, as described in co-owned U.S. Application No. 60/559,917, filed on May 4, 2004. For example, the dinucleotides 5'-UA-3', 5'-UG-3', 5'-CA-3', 5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The antagomir can include at least 2, at least 3, at least 4 or at least 5 of such dinucleotides. In certain embodiments, all the pyrimidines of an antagomir carry a 2'-modification, and the antagomir therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An antagomir can be further modified by including a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

Thus, an antagomir can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the antagomir as well, e.g., the ability to interact with a protein, e.g., a transport protein, e.g., serum albumin, or a member of the RISC, or the ability of the antagomir to form a duplex with another sequence, e.g., a target molecule, such as an miRNA or pre-miRNA.

One or more different NRM modifications can be introduced into an antagomir or into a sequence of an oligonucleotide agent. An NRM modification can be used more than once in a sequence or in an oligonucleotide agent.

NRM modifications include some which can be placed only at the terminus and others which can go at any position. Some NRM modifications that can inhibit hybridization are preferably used only in terminal regions, and more preferably not at the cleavage site or in the cleavage region of the oligonucleotide agent.

Modifications which interfere with or inhibit endonuclease cleavage should not be inserted in the region which is subject to RISC mediated cleavage, e.g., the cleavage site or the cleavage region (As described in Elbashir et al., *Genes and Dev.* 15: 188, 2001, hereby incorporated by reference). Cleavage of the target occurs about in the middle of a 20 or 21 nt oligonucleotide agent, or about 10 or 11 nucleotides upstream of the first nucleotide on the target mRNA which is complementary to the oligonucleotide agent. As used herein, cleavage site refers to the nucleotides on either side of the site of cleavage, on the target mRNA or on the antagomir which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

Delivery of Single-Stranded Oligonucleotide Agents to Tissues and Cells

Formulation

The single-stranded oligonucleotide agents described herein can be formulated for administration to a subject.

For ease of exposition, the formulations, compositions, and methods in this section are discussed largely with regard to unmodified oligonucleotide agents. It should be understood, however, that these formulations, compositions, and methods can be practiced with other oligonucleotide agents, e.g., modified oligonucleotide agents, and such practice is within the invention.

A formulated antagomir composition can assume a variety of states. In some examples, the composition is at least partially crystalline, uniformly crystalline, and/or anhydrous (e.g., less than 80, 50, 30, 20, or 10% water). In another example, the antagomir is in an aqueous phase, e.g., in a solution that includes water, this form being the preferred form for administration via inhalation.

The aqueous phase or the crystalline compositions can be incorporated into a delivery vehicle, e.g., a liposome (particularly for the aqueous phase), or a particle (e.g., a microparticle as can be appropriate for a crystalline composition). Generally, the antagomir composition is formulated in a manner that is compatible with the intended method of administration.

An antagomir preparation can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the antagomir preparation includes another antagomir, e.g., a second antagomir that can downregulate expression of a second gene. Still other preparations can include at least three, five, ten, twenty, fifty, or a hundred or more different oligonucleotide species. In some embodiments, the agents are directed to the same target nucleic acid but different target sequences. In another embodiment, each antagomir is directed to a different target. In one embodiment the antagomir preparation includes a double stranded RNA that targets an RNA (e.g., an mRNA) for donwregulation by an RNAi silencing mechanism.

Treatment Methods and Routes of Delivery

A composition that includes an antagomir featured in the invention, e.g., an antagomir that targets an miRNA or premiRNA (e.g., miR-122, miR-16, miR-192, or miR-194) can be delivered to a subject by a variety of routes. Exemplary routes include inhalation, intrathecal, parenchymal, intravenous, nasal, oral, and ocular delivery.

An antagomir can be incorporated into pharmaceutical compositions suitable for administration. For example, compositions can include one or more oligonucleotide agents and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions featured in the invention may be administered in a number of ways depending upon whether local or systemic treatment is desired and upon the area to be treated. Administration may be topical (including ophthalmic, intranasal, transdermal, intrapulmonary), oral or parenteral. Parenteral administration includes intravenous drip, subcutaneous, intraperitoneal or intramuscular injection, or intrathecal or intraventricular administration.

In general, delivery of an antagomir featured in the invention directs the agent to the site of infection in a subject. The preferred means of delivery is through local administration directly to the site of infection, or by systemic administration, e.g. parental administration.

Formulations for direct injection and parenteral administration are well known in the art. Such formulations may include sterile aqueous solutions which may also contain buffers, diluents and other suitable additives. For intravenous use, the total concentration of solutes should be controlled to render the preparation isotonic.

Administration of Oligonucleotide Agents

A patient who has been diagnosed with a disorder characterized by unwanted miRNA expression (e.g., unwanted expression of miR-122, miR-16, miR-192, or miR-194) can be treated by administration of an antagomir described herein to block the negative effects of the miRNA, thereby alleviating the symptoms associated with the unwanted miRNA expression. Similarly, a human who has or is at risk for deleveloping a disorder characterized by underexpression of a gene that is regulated by an miRNA can be treated by the administration of an antagomir that targets the miRNA. For example, a human diagnosed with hemolytic anemia, and who carries a mutation in the aldolase A gene, expresses a compromised form of the enzyme. The patient can be administered an antagomir that targets endogenous miR-122, which binds aldolase A RNA in vivo, presumably to downregulate translation of the aldolase A mRNA and consequently downregulate aldolase A protein levels. Administration of an antagomir that targets the endogenous miR-122 in a patient having hemolytic anemia will decrease miR-122 activity, which will result in the upregulation of aldolase A expression and an increase in aldolase A protein levels. Although the enzyme activity of the mutant aldolase A is suboptimal, an increase in protein levels may be sufficient to relieve the disease symptoms. A human who has or who is at risk for developing arthrogryposis multiplex congenital, pituitary ectopia, rhabdomyolysis, or hyperkalemia, or who suffers from a myopathic symptom, is also a suitable candidate for treatment with an antagomir that targets miR-122. A human who carries a mutation in the aldolase A gene can be a candidate for treatment with an antagomir that targets miR-122. A human who carries a mutation in the aldolase A gene can have a symptom characterizing aldolase A deficiency including growth and developmental retardation, midfacial hypoplasia, and hepatomegaly.

In another example, a human who has or who is at risk for developing a disorder associated with overexpression of a gene regulated by an miRNA or by an miRNA deficiency, e.g., an miR-122, miR-16, miR-192, or miR-194 deficiency, can be treated by the administration of an antagomir, such as a single-stranded oligonucleotide agent, that is substantially identical to the deficient miRNA.

The single-stranded oligonucleotide agents featured in the invention can be administered systemically, e.g., orally or by intramuscular injection or by intravenous injection, in admixture with a pharmaceutically acceptable carrier adapted for the route of administration. An antagomir can include a delivery vehicle, such as liposomes, for administration to a subject, carriers and diluents and their salts, and/or can be present in pharmaceutically acceptable formulations. Methods for the delivery of nucleic acid molecules are described in Akhtar et al., *Trends in Cell Bio.* 2:139, 1992; Delivery Strategies for Antisense Oligonucleotide Therapeutics, ed. Akhtar, 1995; Maurer et al., *Mol. Membr. Biol.,* 16:129, 1999; Hofland and Huang, *Handb. Exp. Pharmacol.* 137:165, 1999; and Lee et al., *ACS Symp. Ser.* 752:184, 2000, all of which are incorporated herein by reference. Beigelman et al., U.S. Pat. No. 6,395,713 and Sullivan et al., PCT WO 94/02595 further describe the general methods for delivery of nucleic acid molecules. Nucleic acid molecules can be administered to cells by a variety of methods known to those of skill in the art, including, but not restricted to, encapsulation in liposomes, by ionophoresis, or by incorporation into other vehicles, such as hydrogels, cyclodextrins (see for example Gonzalez et al., *Bioconjugate Chem.* 10:1068, 1999), biodegradable nanocapsules, and bioadhesive microspheres, or by proteinaceous vectors (O'Hare and Normand, International PCT Publication No. WO 00/53722).

In the present methods, the antagomir can be administered to the subject either as a naked oligonucleotide agent, in conjunction with a delivery reagent, or as a recombinant plasmid or viral vector which expresses the oligonucleotide agent. Preferably, the antagomir is administered as a naked oligonucleotide agent.

An antagomir featured in the invention can be administered to the subject by any means suitable for delivering the agent to the cells of the tissue at or near the area of unwanted target nucleic acid expression (e.g., target miRNA or pre-miRNA expression). For example, an antagomir that targets miR-122 can be delivered directly to the liver, or can be conjugated to a molecule that targets the liver. Exemplary delivery methods include administration by gene gun, electroporation, or other suitable parenteral administration route.

Suitable enteral administration routes include oral delivery.

Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection, intra-retinal injection, or sub-retinal injection); subcutaneous injection or deposition including subcutaneous infusion (such as by osmotic pumps); direct application to the area at or near the site of neovascularization, for example by a catheter or other placement device (e.g., a retinal pellet or an implant comprising a porous, non-porous, or gelatinous material).

An antagomir featured in the invention can be delivered using an intraocular implant. Such implants can be biodegradable and/or biocompatible implants, or may be non-biodegradable implants. The implants may be permeable or impermeable to the active agent, and may be inserted into a chamber of the eye, such as the anterior or posterior chambers, or may be implanted in the sclera, transchoroidal space, or an avascularized region exterior to the vitreous. In a preferred embodiment, the implant may be positioned over an avascular region, such as on the sclera, so as to allow for transscleral diffusion of the drug to the desired site of treatment, e.g., the intraocular space and macula of the eye. Furthermore, the site of transscleral diffusion is preferably in proximity to the macula.

An antagomir featured in the invention can also be administered topically, for example, by patch or by direct application to the eye, or by iontophoresis. Ointments, sprays, or droppable liquids can be delivered by ocular delivery systems known in the art such as applicators or eyedroppers. The compositions can be administered directly to the surface of the eye or to the interior of the eyelid. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers.

An antagomir featured in the invention may be provided in sustained release compositions, such as those described in, for example, U.S. Pat. Nos. 5,672,659 and 5,595,760. The use of immediate or sustained release compositions depends on the nature of the condition being treated. If the condition consists of an acute or over-acute disorder, treatment with an immediate release form will be preferred over a prolonged release composition. Alternatively, for certain preventative or long-term treatments, a sustained release composition may be appropriate.

An antagomir can be injected into the interior of the eye, such as with a needle or other delivery device.

An antagomir featured in the invention can be administered in a single dose or in multiple doses. Where the administration of the antagomir is by infusion, the infusion can be a single sustained dose or can be delivered by multiple infusions. Injection of the agent can be directly into the tissue at or near the site of aberrant or unwanted target gene expression (e.g., aberrant or unwanted miRNA or pre-miRNA expression). Multiple injections of the agent can be made into the tissue at or near the site.

Dosage levels on the order of about 1 µg/kg to 100 mg/kg of body weight per administration are useful in the treatment of a disease. One skilled in the art can also readily determine an appropriate dosage regimen for administering the antagomir of the invention to a given subject. For example, the antagomir can be administered to the subject once, e.g., as a single injection or deposition at or near the site on unwanted target nucleic acid expression. Alternatively, the antagomir can be administered once or twice daily to a subject for a period of from about three to about twenty-eight days, more preferably from about seven to about ten days. In a preferred dosage regimen, the antagomir is injected at or near a site of unwanted target nucleic acid expression once a day for seven days. Where a dosage regimen comprises multiple administrations, it is understood that the effective amount of antagomir administered to the subject can include the total amount of antagomir administered over the entire dosage regimen. One skilled in the art will appreciate that the exact individual dosages may be adjusted somewhat depending on a variety of factors, including the specific antagomir being administered, the time of administration, the route of administration, the nature of the formulation, the rate of excretion, the particular disorder being treated, the severity of the disorder, the pharmacodynamics of the oligonucleotide agent, and the age, sex, weight, and general health of the patient. Wide variations in the necessary dosage level are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known in the art. The precise therapeutically effective dosage levels and patterns are preferably determined by the attending physician in consideration of the above-identified factors.

In addition to treating pre-existing diseases or disorders, oligonucleotide agents featured in the invention (e.g., single-stranded oligonucleotide agents targeting miR-122, miR-16, miR-192, or miR-194) can be administered prophylactically in order to prevent or slow the onset of a particular disease or disorder. In prophylactic applications, an antagomir is administered to a patient susceptible to or otherwise at risk of a particular disorder, such as disorder associated with aberrant or unwanted expression of an miRNA or pre-miRNA.

The oligonucleotide agents featured by the invention are preferably formulated as pharmaceutical compositions prior to administering to a subject, according to techniques known in the art. Pharmaceutical compositions featured in the present invention are characterized as being at least sterile and pyrogen-free. As used herein, "pharmaceutical formulations" include formulations for human and veterinary use. Methods for preparing pharmaceutical compositions are within the skill in the art, for example as described in Remington's Pharmaceutical Science, 18th ed., Mack Publishing Company, Easton, Pa. (1990), and The Science and Practice of Pharmacy, 2003, Gennaro et al., the entire disclosures of which are herein incorporated by reference.

The present pharmaceutical formulations include an antagomir featured in the invention (e.g., 0.1 to 90% by weight), or a physiologically acceptable salt thereof, mixed with a physiologically acceptable carrier medium. Preferred physiologically acceptable carrier media are water, buffered water, normal saline, 0.4% saline, 0.3% glycine, hyaluronic acid and the like.

Pharmaceutical compositions featured in the invention can also include conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions can be packaged for use in liquid form, or can be lyophilized.

For solid compositions, conventional non-toxic solid carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can include any of the carriers and excipients listed above and 10-95%, preferably 25%-75%, of one or more single-stranded oligonucleotide agents featured in the invention.

By "pharmaceutically acceptable formulation" is meant a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as PluronicP85), which can enhance entry of drugs into the CNS (Jolliet-Riant and Tillement, *Fundam. Clin. Pharmacol.* 13:16, 1999); biodegradable polymers, such as poly (DL-lactide-coglycolide) microspheres for sustained release delivery. Other non-limiting examples of delivery strategies for the nucleic acid molecules featured in the instant invention include material described in Boado et al., *J. Pharm. Sci.* 87:1308, 1998; Tyler et al., *FEBS Lett.* 421:280, 1999; Pardridge et al., *PNAS USA.* 92:5592, 1995; Boado, *Adv. Drug Delivery Rev.* 15:73, 1995; Aldrian-Herrada et al., *Nucleic Acids Res.* 26:4910, 1998; and Tyler et al., *PNAS USA* 96:7053, 1999.

The invention also features the use of a composition that includes surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al., *Chem. Rev.* 95:2601, 1995; Ishiwata et al., *Chem. Phare. Bull.* 43:1005, 1995).

Such liposomes have been shown to accumulate selectively in tumors, presumably by extravasation and capture in the neovascularized target tissues (Lasic et al., *Science* 267:1275, 1995; Oku et al., *Biochim. Biophys. Acta* 1238:86, 1995). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 42:24864, 1995; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also features compositions prepared for storage or administration that include a pharmaceutically effective amount of the desired oligonucleotides in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Alternatively, certain single-stranded oligonucleotide agents featured in the instant invention can be expressed within cells from eukaryotic promoters (e.g., Izant and Weintraub, *Science* 229:345, 1985; McGarry and Lindquist, *Proc. Natl. Acad. Sci. USA* 83:399, 1986; Scanlon et al., *Proc. Natl. Acad. Sci. USA* 88:10591, 1991; Kashani-Sabet et al., *Antisense Res. Dev.* 2:3, 1992; Dropulic et al., *J. Virol.* 66:1432, 1992; Weerasinghe et al., *J. Virol.* 65:5531, 1991; Ojwang et al., *Proc. Natl. Acad. Sci. USA* 89:10802, 1992; Chen et al., *Nucleic Acids Res.* 20:4581, 1992; Sarver et al., *Science* 247: 1222, 1990; Thompson et al., *Nucleic Acids Res.* 23:2259, 1995; Good et al., *Gene Therapy* 4:45, 1997). Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., *Nucleic Acids Symp. Ser.* 27:156, 1992; Taira et al., *Nucleic Acids Res.* 19:5125, 1991; Ventura et al., *Nucleic Acids Res.* 21:3249, 1993; Chowrira et al., *J. Biol. Chem.* 269:25856, 1994).

In another aspect of the invention, RNA molecules of the present invention can be expressed from transcription units (see for example Couture et al., *Trends in Genetics* 12:510, 1996) inserted into DNA or RNA vectors. The recombinant vectors can be DNA plasmids or viral vectors. Oligonucleotide agent-expressing viral vectors can be constructed based on, but not limited to, adeno-associated virus, retrovirus, adenovirus, or alphavirus. In another embodiment, pol III based constructs are used to express nucleic acid molecules of the invention (see for example Thompson, U.S. Pat. Nos. 5,902,880 and 6,146,886). The recombinant vectors capable of expressing the oligonucleotide agents can be delivered as described above, and can persist in target cells. Alternatively, viral vectors can be used that provide for transient expression of nucleic acid molecules. Such vectors can be repeatedly administered as necessary. Once expressed, the antagomir interacts with the target RNA (e.g., miRNA or pre-miRNA) and inhibits miRNA activity. In a preferred embodiment, the antagomir forms a duplex with the target miRNA, which prevents the miRNA from binding to its target mRNA, which results in increased translation of the target mRNA. Delivery of oligonucleotide agent-expressing vectors can be systemic, such as by intravenous or intra-muscular administration, by administration to target cells ex-planted from a subject followed by reintroduction into the subject, or by any other means that would allow for introduction into the desired target cell (for a review see Couture et al., *Trends in Genetics* 12:510, 1996).

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the subject with no significant adverse toxicological effects on the subject.

The term "co-administration" refers to administering to a subject two or more single-stranded oligonucleotide agents. The agents can be contained in a single pharmaceutical composition and be administered at the same time, or the agents can be contained in separate formulation and administered serially to a subject. So long as the two agents can be detected in the subject at the same time, the two agents are said to be co-administered.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage

An antagomir can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmol of antagomir (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of antagomir per kg of bodyweight. The unit dose, for example, can be administered by injection (e.g., intravenous or intramuscular, intrathecally, or directly into an organ), inhalation, or a topical application.

Delivery of an antagomir directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per organ or about 0.3-3.0 mg per organ.

The dosage can be an amount effective to treat or prevent a disease or disorder.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. Because oligonucleotide agent-mediated silencing can persist for several days after administering the antagomir composition, in many instances, it is possible to administer the composition with a frequency of less than once per day, or, for some instances, only once for the entire therapeutic regimen.

In one embodiment, a subject is administered an initial dose, and one or more maintenance doses of an antagomir. The maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Following successful treatment, it may be desirable to have the patient undergo maintenance therapy to prevent the recurrence of the disease state, wherein the compound of the invention is administered in maintenance doses, ranging from 0.01 μg to 100 g per kg of body weight (see U.S. Pat. No. 6,107, 094).

The concentration of the antagomir composition is an amount sufficient to be effective in treating or preventing a disorder or to regulate a physiological condition in humans. The concentration or amount of antagomir administered will depend on the parameters determined for the agent and the method of administration, e.g. direct administration to the eye. For example, eye formulations tend to require much lower concentrations of some ingredients in order to avoid irritation or burning of the ocular tissues. It is sometimes desirable to dilute an oral formulation up to 10-100 times in order to provide a suitable ocular formulation.

Certain factors may influence the dosage required to effectively treat a subject, including but not limited to the severity of the disease or disorder, previous treatments, the general health and/or age of the subject, and other diseases present. It will also be appreciated that the effective dosage of the antagomir used for treatment may increase or decrease over the course of a particular treatment. Changes in dosage may result and become apparent from the results of diagnostic assays. For example, the subject can be monitored after administering an antagomir composition. Based on information from the monitoring, an additional amount of the antagomir composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$s found to be effective in in vitro and in vivo animal models.

Therapeutic and Applications for Treating CNS Disorders

The present invention provides a method for inhibiting expression levels of an miRNA in a mammalian CNS tissue, preferably the brain of a mammal. In addition, the invention encompasses methods for administering a desirable antagomir to a mammal suffering from a disease, disorder or condition of the CNS. A mammal can be a rodent, rabbit, primate, human, etc. The antagomir can be transplanted directly into the defective region of the brain or into the penumbral tissue, which is a tissue adjacent to a lesion or defective region. The tissue adjacent to the lesion provides a receptive environment, similar to that of a developing brain.

The compositions of the present invention can be administered into including, but not limited to ischemic brain, injured brain, injured spinal cord, and into brain that exhibits symptoms of degeneration. Administration of the comosition into the mammal can also be performed in combination with growth factors including, but not limited to brain derived neurotrophic factor (BDNF), nerve growth factor (NGF), and the like.

The present invention is based on the discovery that an antagomir directed to miR-16 efficiently decreased miR-16 levels in mouse brain when injected locally. For example, local injection of a small amount of antagomir-16 efficiently reduced expression of miR-16 in the cortex. This inhibition was specific since the expression of other miRNAs was not affected and no alteration in miR-16 levels were measured in the contra-lateral hemisphere that was injected with PBS. Based on the present disclosure, a skilled artisan would appreciate that any antagomir presented herein can decrease expression levels of the corresponding miRNA. The ability to regulate expression of a desired miRNA in vivo provides a strategy to regulate target genes that are regulated by a particular miRNA. As such, the invention encompasses inhibiting an miRNA in order to increase expression of a target gene that is regulated by the miRNA. The increase expression of a target gene can in turn increase the protein levels corresponding to the target gene.

Based on the present disclosure, the administered antagomir decreases a desired miRNA in a cell of a mammal and hence the increase expression level of a desired target gene. However, the invention should also encompass a secondary effect as a result of the targeted decreased expression level of the desired miRNA. For example, if a target gene is a factor that is secreted from a cell, than the increased expression of the target gene (e.g. secreted factor) results in the increased amount of the factor being secreted. Non-limiting factors include, but are not limited to, leukemia inhibitory factor (LIF), brain-derived neurotrophic factor (BDNF), epidermal growth factor receptor (EGF), basic fibroblast growth factor (bFGF), FGF-6, glial-derived neurotrophic factor (GDNF), granulocyte colony-stimulating factor (GCSF), hepatocyte growth factor (HGF), IFN-γ, insulin-like growth factor binding protein (IGFBP-2), IGFBP-6, IL-1ra, IL-6, IL-8, monocyte chemotactic protein (MCP-1), mononuclear phagocyte colony-stimulating factor (M-CSF), neurotrophic factors (NT3), tissue inhibitor of metalloproteinases (TIMP-1), TIMP-2, tumor necrosis factor (TNF-β), vascular endothelial growth factor (VEGF), VEGF-D, urokinase plasminogen activator receptor (uPAR), bone morphogenetic protein 4 (BMP4), IL1-a, IL-3, leptin, stem cell factor (SCF), stromal cell-derived factor-1 (SDF-1), platelet derived growth factor-BB (PDGFBB), transforming growth factors beta TGFβ-1 and TGFβ-3.

As such, the present invention also includes a method for regulating the secretion of a factor from a cell, whereby the secreted factor can have a beneficial effect on neighboring and/or distal cells. For example, in neurodegenerative disorders, the secreted factors can activate endogenous cells to proliferate and differentiate into cells of the CNS. In another aspect, the factors secreted by the cell targeted by the antagomir can serve to activate endogenous stem cells and/or epedymal cells in the brain and/or spinal cord to proliferate and differentiate into parenchymal cells, including, but not limited to neurons. Thus, the present invention includes a method of using an antigomir to directly and/or indirectly promote repair and plasticity of a CNS tissue in a mammal including, but not limited to brain and spinal cord diseases.

The mode of administration of the compositions of the invention to the CNS of the mammal may vary depending on several factors including the type of disease or disorder being treated, the age of the mammal, whether the compositions have been modified, or the like. For example, an antagomir can be introduced into the brain of a mammal by intracerebral administration. The compositions may be introduced to the desired site by direct injection, or by any other means used in the art for the introduction of compounds into the CNS.

Administration of the compositions of the present invention can be accomplished using techniques well known in the art as well as those described herein or as developed in the future. Exemplified herein are methods for administering compositions of the invention into a brain of a mammal, but the present invention is not limited to such anatomical sites. Rather, the composition can be injected into a number of sites, including the intraventricular region, the parenchyma (either as a blind injection or to a specific site by stereotaxic injections), and the subarachnoid or subpial spaces. Specific sites of injection can be portions of the cortical gray matter, white matter, basal ganglia, and spinal cord. Without wishing to be bound to any particular theory, any mammal affected by a CNS disorder, as described elsewhere herein, can be so treated by one or more of the methodologies described herein.

According to the present invention, administration of the compositions into selected regions of a mammal's brain may be made by drilling a hole and piercing the dura to permit the needle of a microsyringe to be inserted. Alternatively, the compositions can be injected intrathecally into a spinal cord region.

The types of diseases which are treatable using the compositions of the present invention are limitless. For example, among neonates and children, the compositions may be used for treatment of a number of genetic diseases of the CNS, including, but not limited to, Tay-Sachs disease and the related Sandhoffs disease, Hurler's syndrome and related mucopolysaccharidoses and Krabbe's disease. To varying extents, these diseases also produce lesions in the spinal cord and peripheral nerves. In addition, in neonates and children, treatment of head trauma during birth or following birth is treatable by introducing the compositions into the CNS of the individual. CNS tumor formation in children is also treatable using the methods of the present invention.

With respect to adult diseases of the CNS, the cells of the present invention are useful for treatment of Parkinson's disease, Alzheimer's disease, spinal cord injury, stroke, trauma, tumors, degenerative diseases of the spinal cord such as amyotropic lateral sclerosis, Huntington's disease, epilepsy and the like. Treatment of multiple sclerosis is also comtemplated.

The invention is further illustrated by the following examples, which should not be construed as further limiting.

EXAMPLES

Example 1

Single Stranded Oligonucleotide Agents Inhibited miRNA Activity

Figure 1A:
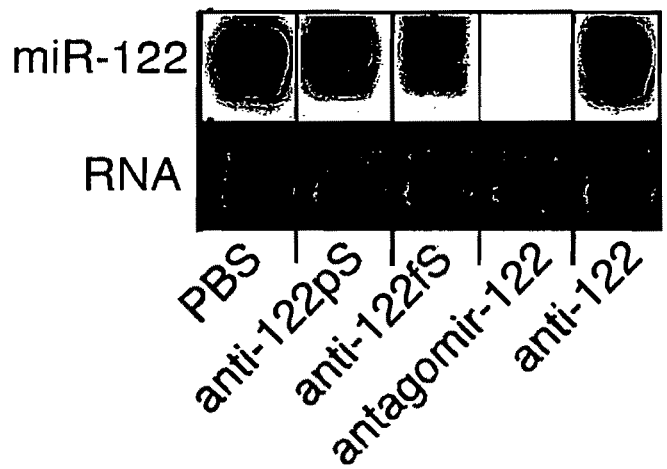
FIG. 1A is a panel of Northern blots of total RNA (15 μg) isolated from mouse liver 24 h after injection of differently modified RNAs (240 mg/kg) targeting miR-122. Samples were separated in 14%-polyacrylamide gels in the absence of formamide, and the membranes were probed for miR-122. Ethidium bromide staining of tRNA is shown as a loading control.
Figure 1B:
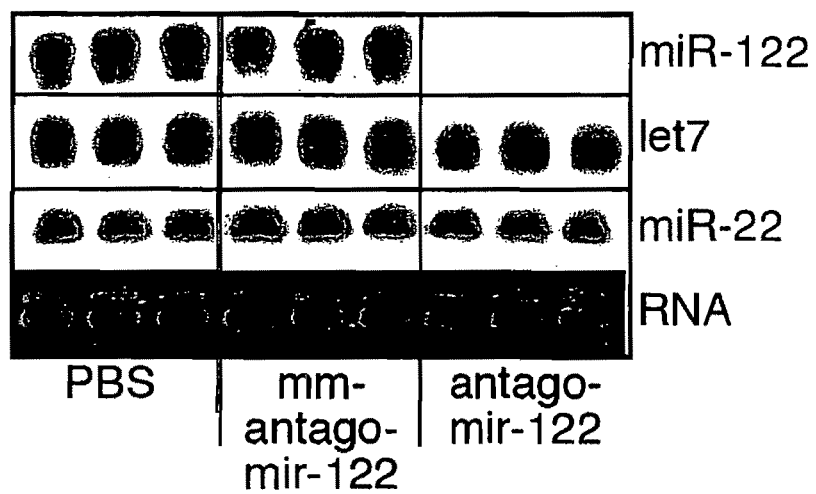
FIG. 1B is a panel of Northern blots of total RNA (15 μg) isolated from mouse liver 24 h after injection of differently modified RNAs (240 mg/kg) against miR-122. Samples were separated in 14%-polyacrylamide gels in the absence of formamide, and the membranes were probed for miR-122, let7, and miR-22 RNAs. Ethidium bromide staining of tRNA is shown as a loading control.

Chemically-stabilized, cholesterol-conjugated single-stranded RNAs complementary to miRNAs were designed and synthesized. These single-stranded modified RNAs are referred to herein as "antagomirs" (see below). To explore the potential of these synthetic RNAs to silence endogenous miRNAs, antagomir-122 was designed to target miR-122, an miRNA expressed in the liver. The sequence of antagomir-122 is shown in Table 3. Antagomir-122 was administered to mice by intravenous injection in a small volume (0.2 ml, 80 mg/kg, 3 consecutive days) and normal pressure. Administration of antagomir-122 resulted in a striking reduction of endogenous miR-122 levels as detected by Northern blot analysis (FIG. 1A). Administration of unmodified single-stranded RNA (anti-122) had no effect on hepatic miR-122 expression levels (FIG. 1A), while injection of unconjugated, but chemically-stabilized single-stranded RNAs with partial (pS) or complete (fS) phosphorothioate backbone and 2'-O-methyl sugar modifications (anti-122fS, anti-122pS, see Table 3) led to an incomplete effect (FIG. 1A). The effects of antagomir-122 were found to be specific as animals injected with a control antagomir-122 derivative that harbored four mismatch mutations (mm-antagomir-122) had no effect on miR-122 expression in the liver. Furthermore, expression levels of miR-let7 and miR-22 were unaffected in antagomir-122 and mm-antagomir-122 treated mice, suggesting that silencing was miRNA-specific (FIG. 1B). The structure of the single stranded RNAs injected into mice is described in Table 3.

TABLE 3

Antagomirs

| RNA | Sequence | AL-SQ NO: | SEQ ID NO: |
|---|---|---|---|
| Anti-122 | 5'-ACAAACACCAUUGUCACACUCCA-3' | 3033 | 40 |
| Anti-122pS | 5'-a$_s$c$_s$aaacaccauugucacac$_s$u$_s$c$_s$c$_s$a-3' | 3226 | 24 |
| Anti-122fS | 5'-a$_s$c$_s$a$_s$a$_s$a$_s$c$_s$a$_s$c$_s$c$_s$a$_s$u$_s$u$_s$g$_s$u$_s$c$_s$a$_s$c$_s$a$_s$c$_s$u$_s$c$_s$c$_s$a-3' | 3037 | 10 |
| antagomir-122 | 5'-a$_s$c$_s$aaacaccauugucacacu$_s$c$_s$c$_s$a$_s$-Chol-3' | 3038 | 5 |
| mm-antagomir-122 | 5'-a$_s$c$_s$acacaacacugucacauu$_s$c$_s$c$_s$a$_s$-Chol-3' | 3040 | 14 |
| antagomir-122(I) | 5'-u$_s$g$_s$gagugugacaaugguguu$_s$u$_s$g$_s$u$_s$-Chol-3' | 3223 | 21 |
| antagomir-122(II) | 5'-u$_s$g$_s$gaaggugacaguguuguu$_s$u$_s$g$_s$u$_s$-Chol-3' | 3224 | 22 |
| antagomir-122(III) | 5'-u$_s$c$_s$acgcgagccgaacgaac$_s$a$_s$a$_s$a$_s$-Chol-3' | 3230 | 28 |
| antagomir-16 | 5'-c$_s$g$_s$ccaauauuuacgugcug$_s$c$_s$u$_s$a$_s$-Chol-3' | 3227 | 6 |

TABLE 3-continued

Antagomirs

Figure 1C:
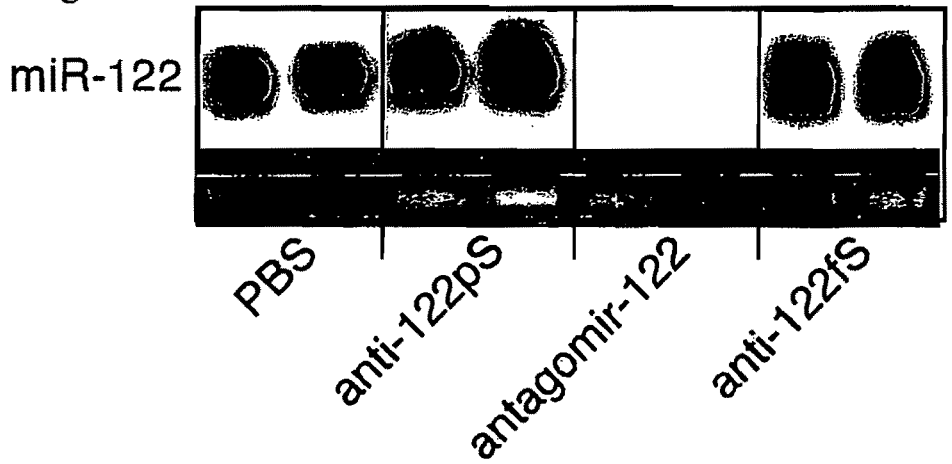
FIG. 1C is a panel of Northern blots of total RNA (15 μg) isolated from mouse liver 24 h after injection of differently modified RNAs (240 mg/kg) against miR-122. Samples were separated in 14%-polyacrylamide gels in the presence of 20% formamide, and the membranes were probed for miR-122. Ethidium bromide staining of tRNA is shown as a loading control.

| RNA | Sequence | AL-SQ NO: | SEQ ID NO: |
|---|---|---|---|
| antagomir-192 | 5'-g$_s$g$_s$cugucaauucauaggu$_s$c$_s$a$_s$g$_s$-Chol-3' | 3228 | 7 |
| antagomir-194 | 5'-u$_s$c$_s$cacauggaguugcuguu$_s$a$_s$c$_s$a$_s$-Chol-3' | 3229 | 8 | lower case letters represent 2'-O-methyl modified nucleotides;
subscript 's' represent phosphorothioate linkage;
"Chol" indicates cholesterol conjugate MiR-122 is expressed at high levels in hepatocytes with over 50,000 copies per cell (Chang J. et al., *RNA Biology* 1:2, 106-113, 2004). To determine whether the silencing of miR-122 following antagomir treatment was caused by stoichiometric duplex formation between miR-122 and antagomir-122 or by catalytic degradation of miR-122, total RNA from livers of mice treated with unconjugated single-stranded anti-miR-122 RNAs (anti-122fS, anti-122pS) or antagomir-122 were examined under stringent, formamide-containing denaturing conditions (FIG. 1C). No difference in miR-122 levels could be detected between PBS and unconjugated anti-miR-122 RNA-treated livers, showing that the decrease in miR-122 levels observed under non-stringent conditions was not caused by degradation, but instead by the formation of miR-122/RNA duplexes. In contrast, miR-122 remained undetectable in livers of mice treated with antagomir-122. These data suggest that the silencing of miRNA-122 in livers of mice treated with antagomir-122 was due to degradation of the miRNA, and the ability of antagomir-122, but not unconjugated anti-122 RNAs, to result in miR-122 degradation may be due to efficient delivery of antagomirs to hepatocytes.

Figure 2A:
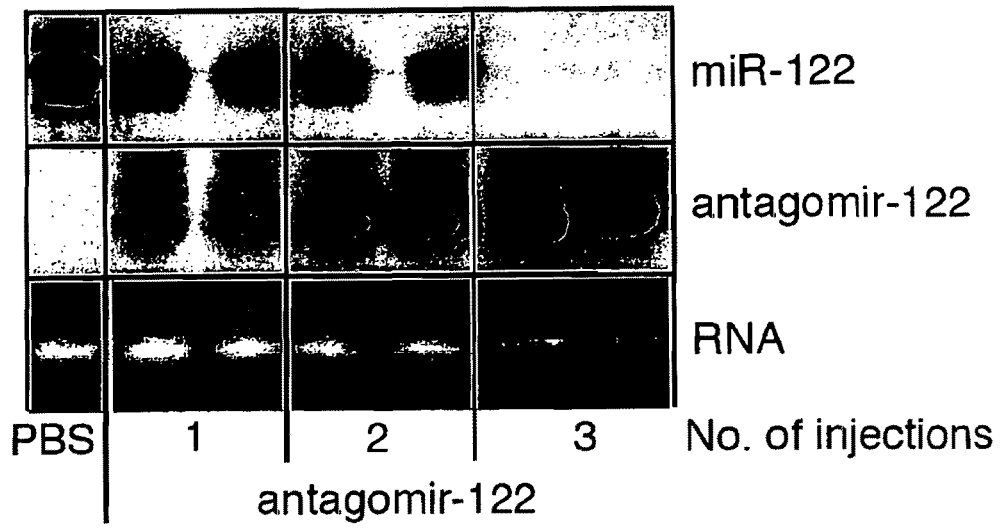
FIG. 2A is a panel of Northern blots of total RNA (15 μg) isolated from mouse livers. RNA was isolated 24 h after injection of 80 mg/kg bodyweight antagomir-122 (n=2) on 1, 2, or 3 consecutive days as indicated. Membranes were probed for both the endogenous miR-122 and the injected antagomir-122. Ethidium bromide staining of tRNA is shown as a loading control.

To determine the dose of antagomir-122 that can completely silence miR-122, mice were injected with 80, 160 or 240 mg/kg bodyweight antagomir-122 and miR-122 expression levels were measured. The highest dose (240 mg/kg bodyweight) resulted in a complete loss of miR-122 signal and was subsequently used for all other experiments (FIG. 2A).

Figure 2B:
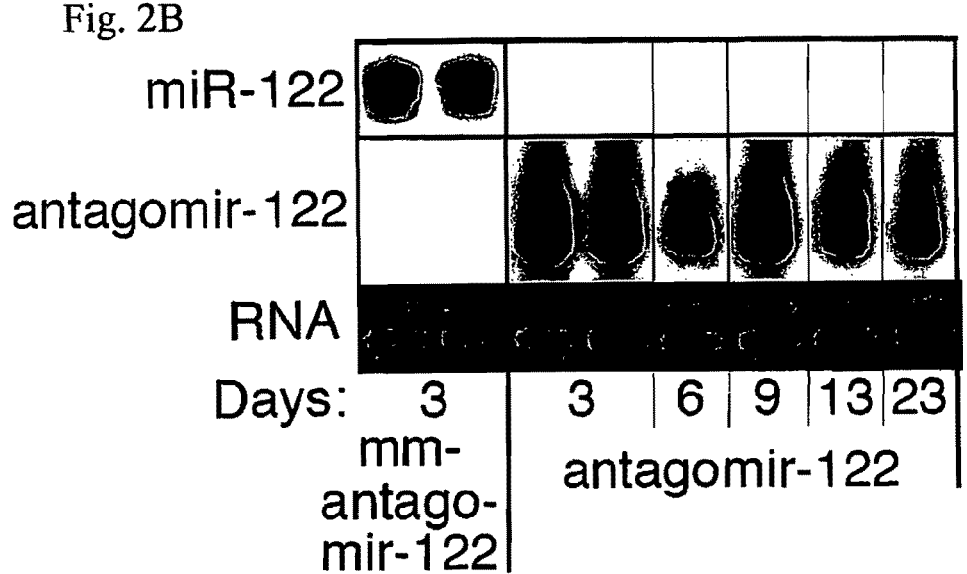
FIG. 2B is a panel of Northern blots of total RNA (15 μg) isolated from mouse livers. RNA was isolated 3, 6, 9, 13, and 23 days after injection of antagomir-122. Membranes were probed for both the endogenous miR-122 and the injected antagomir-122. Ethidium bromide staining of tRNA is shown as a loading control.
Figure 3A:
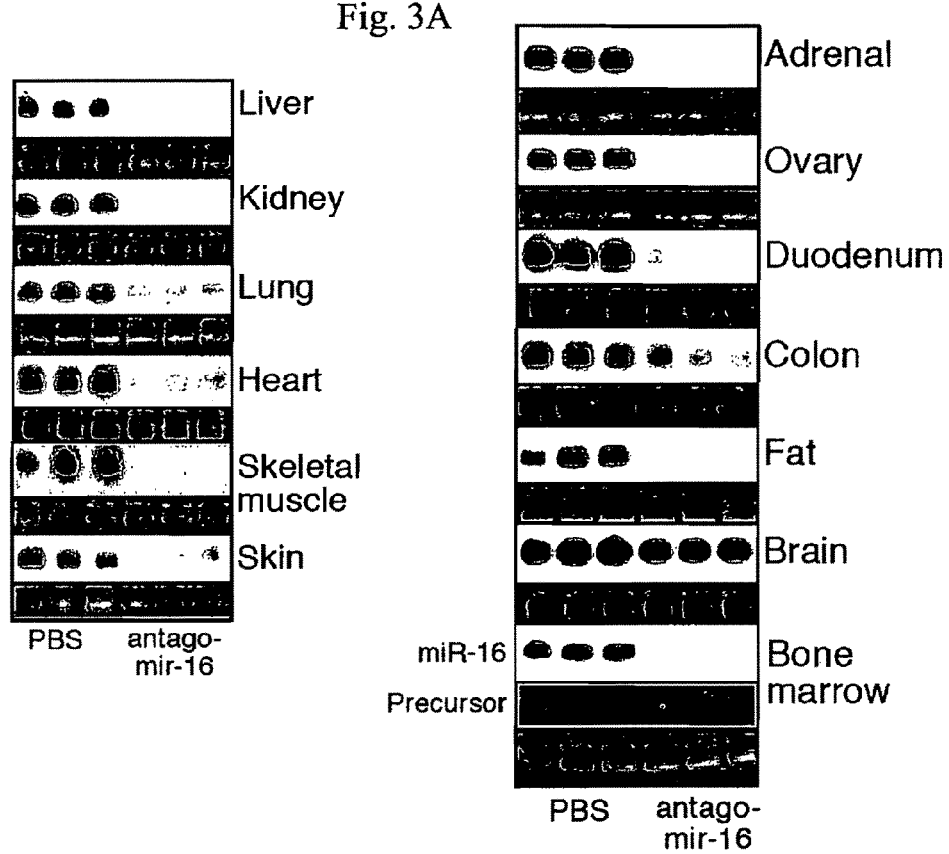
FIG. 3A is a panel of Northern blots of total RNA (10-30 μg) isolated from different mouse tissues 24 h after injection of antagomir-16 (n=3). Membranes were probed for miR-16. The precursor miR-16 transcript was visible on Northern blots of bone marrow and expression was similar in all mice. Ethidium bromide staining of tRNA is shown as a loading control.
Figure 3B:
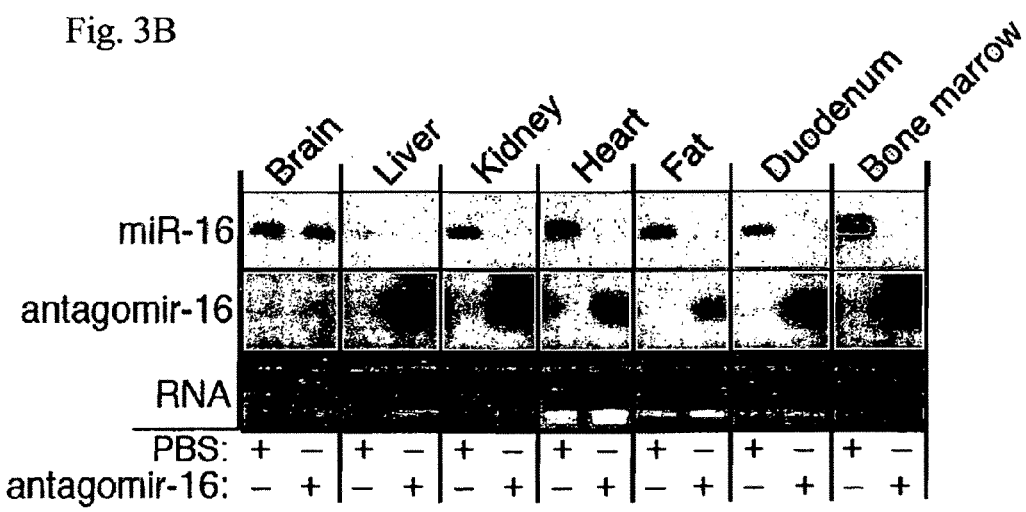
FIG. 3B is a panel of Northern blots of total RNA (10-30 μg) isolated from different mouse tissues 24 h after injection of antagomir-16 (n=3). Total RNA from 3 mice were pooled for the detection of miR-16 and the injected antagomir-16. Ethidium bromide staining of tRNA is shown as a loading control.

The duration of silencing with antagomir-122 was also measured. Levels of miR-122 were undetectable for as long as 23 days post-injection (FIG. 2B), indicating that silencing of miRNAs using antagomirs is long lasting. The injected antagomirs were well tolerated even during the course of the prolonged treatment; no alterations in bodyweight or serum markers of liver toxicity (alanine aminotransferase) were detected. To test the bioavailability of antagomirs in vivo and their ability to silence miRNA expression in different tissues, mice were injected with antagomir-16 directed to miR-16, which is abundantly expressed in all tissues (miR-16 is predicted to target one or both of Activin type II receptor gene, which is involved in TGFbeta signaling, and Hox-A5I (John et al., *PLoS Biology* 2:1862-1878, 2004; correction in *PLoS Biology* 3:1328, 2005)). Tissues were harvested one day after the final injection, and miRNA expression levels were compared to PBS-injected mice. Northern blot analysis revealed that expression of miR-16 was efficiently silenced in all tissues tested except brain (FIG. 3A). Antagomir-16 did not affect the expression of the 89 nt precursor of miR-16 as detected in bone marrow. The bioavailability of antagomir-16 was also assessed by Northern blotting in the above mentioned tissue samples. In concordance with the ability to silence miR-16 levels, significant levels of antagomir-16 were detected in all tissues except brain (FIG. 3B). Together, these data demonstrate that antagomirs achieve broad biodistribution and can efficiently silence miRNAs in most tissues in vivo.

Many miRNA genes have been found to be located in close proximity and to be coordinately transcribed. These polycistronic miRNA genes are transcribed to generate long primary transcripts (pri-miRNAs), which are processed by multiple enzymes in the nucleus and cytoplasm to generate the mature miRNA. To investigate if antagomirs targeting polycistronic miRNAs retain their target specificity with no effect on the expression of neighboring miRNAs, mice were injected with antagomirs targeting either miR-192 or miR-194 of the bicistronic cluster miR-192/194. Administration of antagomir-192 into mice resulted in silencing of miR-192 in liver and kidney, with no effect on the expression levels of miR-194. Conversely, injection of antagomir-194 into mice abolished miR-194 expression but had no demonstrable effect on the miR-192 levels compared to PBS-injected mice. These data demonstrate that antagomirs have the ability to differentially silence specific miRNAs that derive from the same primary transcript.

To test whether silencing of an miRNA can cause a corresponding increase in target protein and possibly mRNA levels, the expression of aldolase A, a gene that is repressed in hepatocytes and predicted to be a target of miR-122, was examined. The aldolase-A mRNA has a conserved nucleotide sequence with perfect sequence complementarity to miR-122 between nucleotides 29 and 36 downstream of the open reading frame. Aldolase-A expression was increased 4-5 fold in livers of mice injected with antagomir-122 compared to a scrambled control (mm-antagomir-122). This regulation was observed in multiple experiments and different time points after injection. The target was also independently confirmed by cloning the 3'UTR Aldolase-A downstream of the luciferase open reading frame and cotransfecting this vector with control miRNAs (miR-124 (5'-UAAGGCACGCG-GUGAAUGCCA-3 SEQ ID NO:41); see Krek et al., *Nature Genetics* 37:495-500, 2005, and Lim et al., *Nature* 433:769-773, 2005) and miR-192) and miR-122 into HEK293 cells, which lack miR-122 expression. Cotransfection of miR-122 resulted in a significant reduction in luciferase activity compared to miR-124 and miR-192 transfected cells. Together, these data indicate that aldolase-A is a physiological target of miR-122.

The upregulation of aldolase-A in mice treated with antagomir-122 demonstrates functional silencing of this miRNA. Aldolase-A is a housekeeping gene expressed in all cells. This gene is produced in large amounts in muscle where it can be as much as 5% of total cellular protein. In adult liver, aldolase-A expression is repressed and aldolase-B is produced. Conversely, dedifferentiated hepatocytes and transformed liver cells have increased aldolase-A expression levels and can even replace aldolase-B. Expression of miR-122 shows an inverse relationship with aldolase-A expression, with highest levels in differentiated adult hepatocytes and complete absence in undifferentiated cells such as HepG2. In contrast, the mRNA levels of aldolase-B, which lacks miR-122 target sites, were unaffected by antagomir-122. These findings provide non-genetic, pharmacologic evidence in mammals that microRNAs define tissue-specific gene expression.

To identify other genes regulated by miR-122, we carried out gene expression analysis using Affymetrix™ arrays (Affymetrix, Inc., Santa Clara, Calif.) in livers from mm-antagomir-122 and antagomir-122 treated mice. We identified 493 gene transcripts that were up-regulated ($\geq$1.4-fold) and 365 transcripts ($\leq$1.4-fold) that were down-regulated in antagomir-122 treated mice compared to controls. The regulation of genes that were up-regulated in antagomir-122-treated livers was confirmed by RT-PCR. Strikingly, these included those members of gene families that are usually repressed in hepatocytes, including alodolase A (aldo-A), N-Myc downstream regulated gene (Ndrg3), IQ motif containing GTPase activating protein-1 (Iggap1). MiR-122 could therefore contribute to the maintenance of the adult liver phenotype, as previously suggested for two other specific miRNAs (Lim et al., *Nature* 433:769-773, 2005). To assess further the motif contents of significantly up- and down-regulated genes, we analyzed the 3'UTR sequences of 9554 mRNAs. Of these, 142 mRNAs were significantly up-regulated and had a fold-change of at least 1.4. We observed a highly significant 2.6-fold increase in the probability to have at least one miR-122 nucleus in the 3'UTR of up-regulated genes compared to genes with no change in mRNA levels. Interestingly, the majority of the miR-122 nuclei in up-regulated genes had not been detected by previous prediction methods (see, e.g., Lewis et al., *Cell* 120:15-20, 2005), indicating that the number of direct miRNA targets is significantly larger then previously estimated.

To experimentally validate the link between repression and the presence of miR-122 nuclei matches within the 3'UTR, we cloned the 3' UTR of four genes repressed by antagomir-122 and containing a miR-122 nucleus into a luciferase reporter system. When co-transfected with miR-122, all reporters exhibited significant repression relative to co-transfections with control miRNA (si-124), suggesting that miR-122 binding to its nucleus contributes directly to mRNA repression. Surprisingly, we also observed that the probability for down-regulated genes to harbor a miR-122 nucleus was reduced by almost the same factor of 2.7-fold. To further analyze if over-representation and under-representation of miR-122 nuclei is specific, we analyzed the abundance of all 4096 possible 6-mer motifs across down-, up-, and "no change" transcripts. When comparing up-regulated versus no change genes, the miR-122 nucleus (CACTCC) was the most significantly over-represented 6-mer. Similarly, the miR-122 nucleus was within the top 0.5% of under-represented motifs for down-regulated transcripts, indicating an evolutionary tendency of down-regulated genes to lack binding sites for miR-122. These results indicate that up-regulated mRNAs are directly targeted and repressed by miR-122, but also that a significant number of down-regulated genes are likely to be either directly or indirectly activated by miR-122.

To assess the functional significance of altered gene regulation by miR-122 we analyzed the functional annotation of regulated genes for enrichment in Gene Ontology categories (see Methods). The top ranking functional category was "cholesterol biosynthesis" with a p-value of $1.6 \times 10^{-11}$ and was found for gene transcripts down-regulated by antagomir-122. The expression of at least 13 genes involved in cholesterol biosynthesis was decreased between 1.4 to 2.3-fold in antagomir-122 treated mice ; some of these were confirmed by RT-PCR. Interestingly, mice injected with an adenovirus expressing miR-122 (Ad-122) increased expression of some of these genes. One of these gene transcripts down-regulated by antagomir-122 treatment was HMG-CoA-reductase (Hmgcr), a rate-limiting enzyme of endogenous cholesterol biosynthesis and the target for statin-based drugs. We measured the enzymatic activity of Hmgcr in liver extracts and found a ~45% reduction in Hmgcr activity in antagomir-122 vs. mm-antagomir-122 treated mice (9.7±1.0 versus 17.2±2.3 pmol/mg microsomal protein/min, respectively; n=5, P=0.02). Consistent with this effect on Hmgcr activity, plasma cholesterol levels were decreased >40% in antagomir-122 treated animals while there was no detectable effect on plasma free fatty acids (FFA), triglyceride, bile acid and glucose levels. No decrease in plasma cholesterol was observed with antagomir-192, -194 and -16, showing that together with the absence of effects by mm-antagomir-122, the effects of antagomir-122 are sequence specific and unrelated to the use of a cholesterol-conjugated oligonucleotide per se. Reduced plasma cholesterol levels in antagomir-122 treated mice lasted for at least 2 weeks. Together, these data demonstrate that miR-122 is a regulator of the cholesterol biosynthetic pathway.

Figure 12:
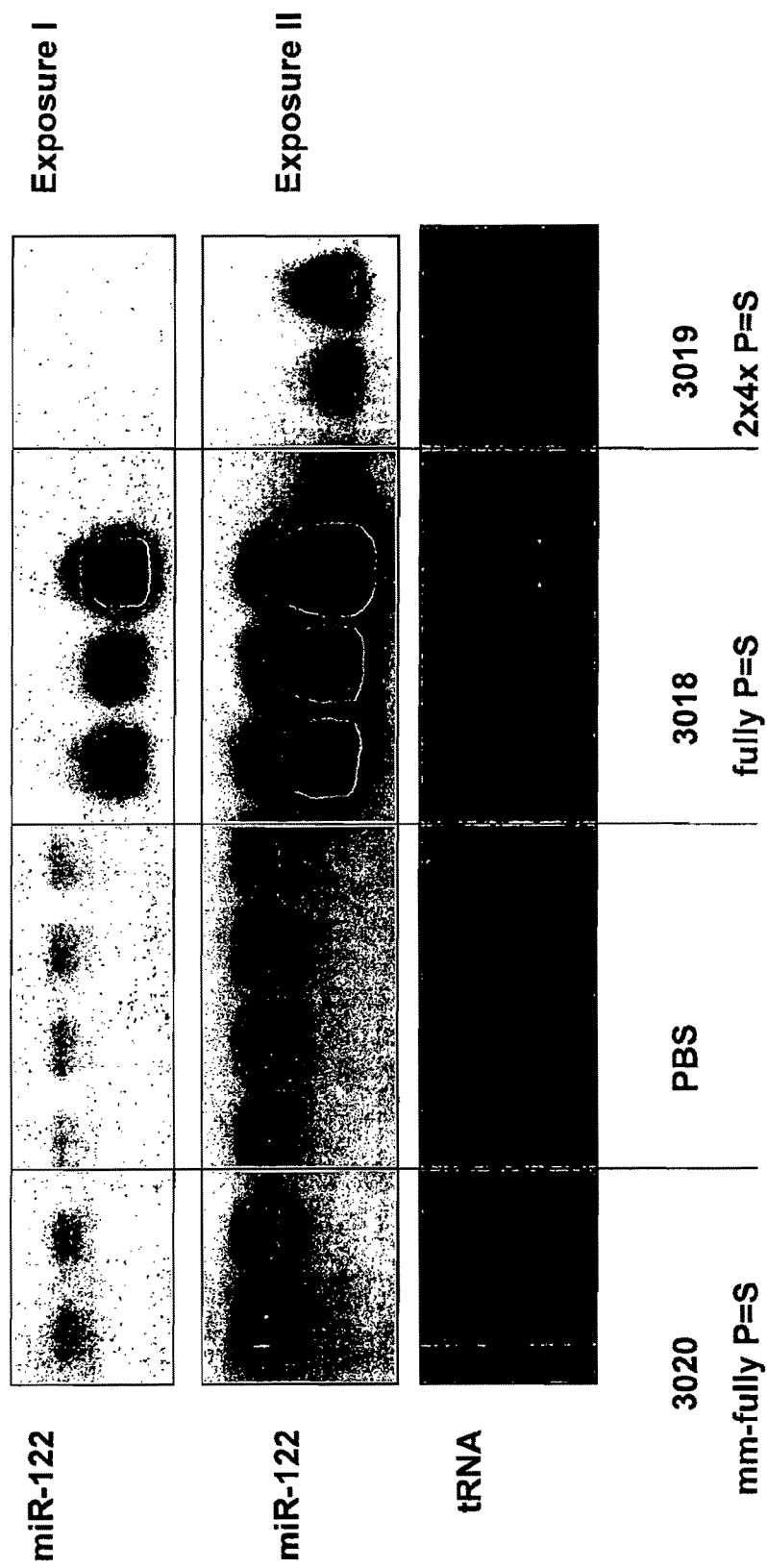
FIG. 12 depicts activity of double-stranded antagomirs (see Table 2f for the description of agents used).

To test whether double stranded antagomirs were effective, six-week old femaleC57BL/6 mice were injected via the tail vein with 80 mg/kg/day on three consecutive days with either PBS, or compounds AP-3018, -3019, -3020 in a total volume of 0.2 ml. The liver was harvested 24 hrs after the last injection and total RNA was isolated using Trizol (Invitrogen). 10 µg of total RNA was run on formamide containing polyacrylamide gels, blotted and probed for miR-122 using a 32P-labeled antisense oligo. Two different autoradiography exposures are shown (see FIG. 12). Each lane represents an individual animal. Double stranded antagomirs were able to reduce mircoRNA levels.

Our data demonstrate that antagomirs are effective inhibitors of miRNAs in vivo. Silencing of miR-122 by antagomirs allowed us to study gene regulation by a tissue-specific miRNA in vivo. Of the genes that were up-regulated, only 12 genes (including AldoA, citrate synthase and Iqgap1) had previously been predicted using bioinformatic approaches (Krek et al., *Nat. Genet.* 37:495-500, 2005). Since 52% of all up-regulated genes have at least one miR-122 nucleus in their 3'UTR sequence this indicates that they are likely direct targets. Notably, silencing of miR-122 also led to a reduction of a significant number of genes. We found that these genes have a drastically reduced probability to contain a miR-122 nucleus in their 3'UTR.

Methods

Synthesis of antagomirs RNAs were synthesized using commercially available 5'-O-(4,4'-dimethoxytrityl)-2'-O-methyl-3'-O-(2-cyanoethyl-N, N-diisopropyl) RNA phosphoramidite monomers of 6-N-benzoyladenosine (ABz), 4-N-benzoylcytidine (CBz), 2-N-isobutyrylguanosine (GiBu), and uridine (U), according to standard solid phase oligonucleotide synthesis protocols (Damha and Ogilvie, *Methods Mol. Biol.* 20:81-114, 1993). For antagomirs, i.e., cholesterol conjugated RNAs, the synthesis started from a controlled-pore glass solid support carrying a cholesterol-hydroxyprolinol linker (Manoharan et al., U.S. Pat. Appl. Publ. 20050107325). Antagomirs with phosphorothioate backbone at a given position were achieved by oxidation of phosphite with phenylacetyl disulfide (PADS) during oligonucleotide synthesis (Cheruvallath et al., *Nucleosides Nucleotides* 18:485-492, 1999). After cleavage and de-protection, antagomirs were purified by reverse-phase high-performance liquid chromatography, while the unconjugated RNA oligonucleotides were purified by anion-exchange high-performance liquid chromatography. Purified oligonucleotides were characterized by ES mass spectrometry and capillary gel electrophoresis.

Animals. All animal models were maintained in C57B1/6J background on a 12 hours light/dark cycle in a pathogen-free animal facility at Rockefeller University. Six week old mice received, on one to three consecutive days, tail vein injections of saline or different RNAs. RNAs were administered at doses of 80 mg/kg body weight in 0.2 ml per injection. Measurements of miRNA levels in tissues were performed 24 h after the last injection unless indicated otherwise. Tissues were harvested, snap frozen and stored at −80° C.

Generation of recombinant adenovirus. The recombinant adenovirus used to express miR-122 (Ad-122) was generated by PCR, amplifying a 344 by miRNA precursor sequence with primers 5'-AGTCAGATGTACAGTTATAAGCACAA-GAGGACCAG-3' (SEQ ID NO:42) and 5'-TTATTCAA-GATCCCGGGGCTCTTCC-3' (SEQ ID NO:43). The fragment was cloned into vector Ad5CMV-KnpA. Ad-EGFP (ViraQuest, North Liberty, Iowa) was used as a control. Mice were infected with $1 \times 10^9$ pfu/mouse by tail vein injection.

Gene expression analysis. Total RNA of mice treated with antagomirs or recombinant adenovirus was isolated three days after treatment. RNA was pooled from four animals for each group. The integrity of the RNA sample was assessed by denaturing formamide gel analysis. First strand cDNA synthesis was completed with total RNA (30 µg) cleaned with RNAeasy columns (Qiagen, Valencia, Calif.) and the Superscript Choice cDNA synthesis protocol (Invitrogen, Carlsbad, Calif.), except and HPLC purified T7-promoter-dT30 primer (Proligo LLC, Boulder, Colo.) was used to initiate the first strand reaction. Biotin labeled cRNA was synthesized from T7 cDNA using the RNA transcript labeling kit (Enzo Biochem, Farmingdale, N.Y.), supplemented with biotin 11-CTP and biotin-UTP (Enzo Biochem, Farmingdale, N.Y.) as specified by the Affymetrix protocol. The sample was cleaned with an RNAeasy column (Qiagen, Valencia, Calif.) to remove free nucleotides and then quantitated spectrophotometrically. Biotin-labeled cRNA was fragmented and hybridized to Mouse Expression Set 430 arrays (Affymetrix, Inc., Santa Clara, Calif.) according to the manufacturer's manual with a final concentration of fragmented cRNA of 0.05 µg/ul. The arrays were scanned using a Hewlett Packard confocal laser scanner and analyzed using ArrayAssist Lite and Affymetrix® Microarray Suite v.5 (MASS) software.

Northern blotting analysis. Total RNA was isolated using the Trizol® reagent (Invitrogen, Carlsbad, Calif.) and ethanol precipitation. RNA was separated at 45 mA on 14%-polyacrylamide gels that contained 8 M urea and 20% formamide. Antisense probes were designed according to the "microRNA registry" (Griffiths-Jones, *NAR* 32:D109-D111, 2004).

RT-PCR. Extraction of total RNA, synthesis of cDNA, and PCR were carried out as described in Shih et al. (*Proc. Natl. Acad. Sci. U.S.A.* 99:3818-3823, 2002).

Assay of luciferase activity. The mouse full length adolase-A 3'UTR was PCR-amplified using the following primers: 5' d-(CCAGAGCTGAACTAAGGCTGCTCCA)-3' (SEQ ID NO:44) and 5' d-(CCCCTTAAATAGTTGTTTAT TGGCA)-3' (SEQ ID NO:9) and cloned downstream of the stop codon in pRL-TK (Promega, Madison, Wis.). HEK293 cells were cultured in 24-well plates and each transfected with 50 ng of pRL-TK (Rr-luc), 50 ng of pGL3 control vector (Pp-luc) (Promega, Madison, Wis.) and 200 ng of double-stranded siRNA (Dharmacon, Lafayette, Colo.). Cells were harvested and assayed 24-30 h post-transfection.

3'UTR sequences and mapping of array probes to transcripts. We extracted mouse 3' UTRs using the Refseq data set (Pruitt et al., *Nucleic Acids Res.* 33:D501-D504, 2005). 17264 3' UTR sequences of at least 30 nucleotides in length were obtained. Affymetrix probe identifiers were assigned to the Refseq transcripts by using a mapping provided by Ensembl software (Hubbard et al., *Nucleic Acids Res.* 33 *Database issue:* D447-D453, 2005). When only one probe identifier mapped to a transcript, the significance call for a fold change and the fold change itself, as provided by the Affymetrix software, was taken at face value. When more than one probe identifier mapped to a transcript, we insisted that the significance call was consistent for all probes. Transcripts were discarded otherwise. The fold change assigned to a transcript was the average of all probes that mapped to the transcript. Finally, a cut-off of 0.5 in the logarithm (base 2) of fold changes was applied.

Gene Ontology analysis. Refseq identifiers were mapped to MGI identifiers using a map provided by Ensembl software (Hubbard et al., *Nucleic Acids Res.* 33 *Database issue:* D447-D453, 2005). We then used the program FuncAssociate (Castillo-Davis and Hartl, *Bioinformatics* 19:891-892, 2003) with default settings to search for overrepresented Gene Ontology terms. Results were sorted by LOD scores. Independently, we obtained very similar results with the program GeneMerge v.1.2 and by applying a conservative Bonferroni correction for multiple testing.

HMG-CoA reductase (HMGR) activity assay. Hepatic microsomal HMGR activity was assayed by a method modified from a previously published procedure (Nguyen, et al., *J. Clin. Invest.* 86:923-931, 1990). Briefly, hepatic microsomal protein extracts were preincubated with an NADPH-generating system (3.4 mM NADP+/30 mM glucose 6-phosphate/ 0.3 units of glucose-6-phosphate dehydrogenase) in buffer (50 mM $K_2PHO_4$/70 mM KCl/10 mM DTT/30 mM EDTA, pH 7.4). The reaction was started with the addition of 15 µl $^{14}$C-labeled substrate ([$^{14}$C]HMG CoA, (Amersham, Piscataway, N.J.)). The mixture was incubated for 15 min. and stopped with 15 µl 6 M HCl. [$^3$H]mevalonolactone and unlabeled mevalonolactone were added for recovery standard and product marker, respectively. After lactonization the products were extracted with ether and separated by TLC on Silica Gel 60 plates (VWR Scientific, West Chester, Pa.) with benzene/ acetone (1:1, vol/vol) as the solvent system. The immediate product ($^{14}$C-labeled mevalonolactone) was quantitated by scintillation spectrometry.

Statistical analysis. Results are given as mean±s.d. Statistical analyses were performed by using Student's t-test, and the null hypothesis was rejected at the 0.05 level.

Example 2

Trizol® Reagent and Ethanol Can be Used To Precipitate a miR-122/Antagomir-122 Duplex A Trizol® (Invitrogen, Carlsbad, Calif.) protocol was modified for precipitation of a miR-122/antagomir 122 duplex. A duplex containing a synthetic miR-122 (22 nt, Dharmacon, Lafayette, Colo.) and antagomir-122 molecule was formed by incubating equal amounts of miR-122 and antagomir-122 in water for 1 min. at 95° C. followed by an incubation at 37° C. for 1 hr. The duplex was then added to the aqueous phase of a Trizol®/liver extract and aliquots were subjected to different precipitation methods (10 min. at room temperature with 50% or 80% isopropanol followed by 10 min. centrifugation at 13,200 rpm at 4° C.; or 30 min. at −80° C. with 70% ethanol and 0.5 M ammonium acetate or 0.08 M sodium acetate followed by 20 min. centrifugation at 13,200 rpm at 4° C.). The precipitates were washed once with 85% ethanol, dissolved in water, separated on a 14% sequencing gel and visualized using ethidium bromide. The respective input of the duplex was loaded in comparison (1.4 mg/lane).

The duplex did precipitate in (i) 80% isopropanol, (ii) in 70% ethanol/0.5M NH$_4$-Acetate, and (iii) in 70% ethanol/0.08M Na-acetate. The duplex would not precipitate in 50% isopropanol, which follows the conventional Trizol® protocol.

Example 3

Trizol® Did Not Precipitate a miR/Antagomir Duplex in the Absence of Ethanol or Isopropanol Liver tissue was homogenized in Trizol®, aliquoted into eppendorf tubes (1 ml volume each) and preformed duplex miR-122/antagomir-122 or miR-16/antagomir-16 was added. Samples were vortexed and left at room temperature for 10 minutes. 200 ml of chloroform were added and samples vortexed for 2 min at room temperature, followed by centrifugation at 13,200 rpm at room temperature for 15 minutes. 400 ml of the supernatant were added to 1 ml 100% ethanol and 40 ml 3 M sodium acetate, pH 5.2. After 30 min. at −80° C. samples were centrifuged for 20 min. at 4° C. Precipitates were washed with 85% ethanol, dissolved in water, separated on a 14% sequencing gel and visualized using ethidium bromide. The input was loaded for comparison (5 mg per lane). The miR/antagomir duplex was not precipitated by this Trizol® protocol, which lacked ethanol or isopropanol, although a faint signal indicated some recovery of single-stranded miR.

In a similar assay, liver/Trizol® homogenates were processed exactly as described, but 4 mg each of (i) miR-122, (ii) antagomir-122, (iii) anti122pS, or (iv) miR-122 (4 mg) and antagomir-122 (4 mg) together were added to the homogenates. After the incubation and precipitation steps, only miR-122 was isolated. This was the result whether miR-122 alone was added to the homogenate, or whether miR-122 was added in combination with antagomir-122.

When preformed duplex of miR-122/antagomir-122 (4 mg of each) were added to the liver/Trizol® homogenates, miR-122, but not antagomir-122, was isolated from the preformed duplex.

To further test the Trizol® precipitation protocol, total liver RNA was isolated (using the protocol), and then the RNA was dissolved in water. 40 mg of the isolated RNA were incubated in a total volume of 50 ml water with the increasing amounts of antagomir-122 for 5 min. at 65° C. followed by 2 h at 37° C. and 30 min. at room temperature. The amounts of antagomir-122 tested were 6.4 pg, 320 pg, 16 ng, 0.8 µg, 40 µg, and 120 µg. 1 ml of Trizol® was added to the samples and Trizol® extraction was performed again as described above. The precipitates were dissolved in 60 ml water, and then 30 ml of each sample was separated on 14% polyacrylamide gels with or without 20% formamide. miR-122 was then detected using Northern blotting.

The miR-122 was precipitated and detected by gel electrophoresis in the presence of formamide regardless of the amount of antagomir-122 added to the precipitation mix. When 40 µg or 120 µg were used in the precipitation mix, a duplex between miR-122 and antagomir was visible when analyzed on a sequencing gel. Minor amounts of antagomir were always retrieved by the Trizol® protocol.

To test the precipitation protocol with smaller amounts of RNA, total RNA was isolated from liver or kidney using the Trizol® protocol and then the RNA was dissolved in water. 10 mg of RNA were incubated for 3 h at 37° C. in a total volume of 50 ml water together with 20 mg antagomir-122. The kidney RNA, which does not contain endogenous miR-122, was spiked with 20 fmoles of synthetic miR-122. 1 ml of Trizol® was added and then Trizol® extraction was performed again as described above. Precipitates were dissolved in 30 ml water and separated in a 14% polyacrylamide gel containing 20% formamide. First, miR-122 was detected using Northern blotting, then the membrane was re-probed against antagomir-122, which detected the presence of the antagomir-122. Incubation with antagomir-122 did not alter the miR-122 signal detected on the gel.

Mice were administered 80 mg/kg/day antagomir-122 or a scrambled control (mm-antagmir122) via tail-vein on three separate days. Livers were harvested at days 3, 6, 9, 13, and 23 post-injection, and subjected to Trizol® isolation as described above. Approximately 50 mg liver were homogenized in 1 ml Trizol®. Analysis by Northern blot indicated that antagomir-122 could be detected for at least 23 days post-injection.

Example 4

A bDNA Lysis Protocol Allows Quantitative Isolation of miR-122/Antagomir-122 Duplexes and miR-122 Single-Stranded Molecules 100 mg liver were sonicated in 2 ml T+C (Epicentre®, Madison, Wis.) in the presence of 350 mg proteinase K. 100 ml of the homogenate was supplemented with either miR-122/antagomir-122 duplexes (8 mg per lane), miR-122 (4 mg per lane) or antagomir-122 (4 mg per lane). 200 ml 1× STE-buffer was added, then 200 ml of phenol, pH 4 or pH 8. Samples were vortexed for 30 sec and left on ice for 2 min. After centrifugation for 10 min at 13,200 rpm (4° C.), 280 ml of the supernatant was added to 900 ml 100% ethanol and incubated for 90 min at 90° C. RNA was precipitated for 10 min at 13,200 rpm, washed once with 85% ethanol, dissolved in water and separated on a sequencing gel. miR-122/antagomir-122 duplexes and miR-122 (but not antagomir-122) were detected by ethidium bromide staining. The duplexes and miR-122 were successfully isolated with phenol at pH4 and at pH 8.

Example 5

Antagomir-122 Caused a Decrease in miR-122 Levels In Vivo

Figure 4:
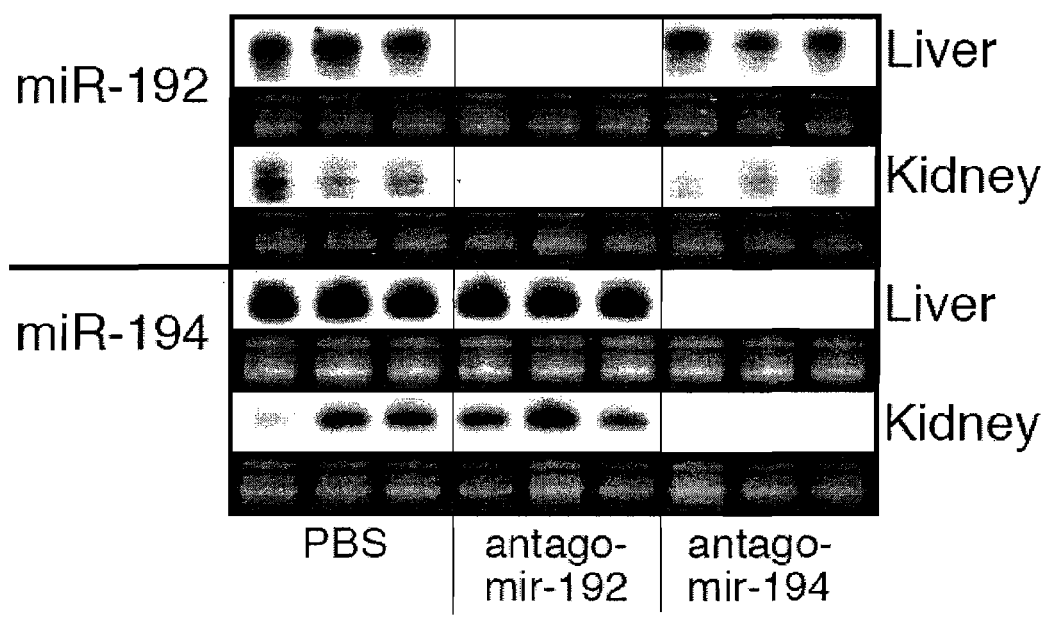
FIG. 4 includes a panel of Northern blots of total RNA isolated from livers of mice injected with antagomiR-122, mm-antagomir-122, or PBS. RNA was extracted 24 h after injection by a bDNA lysis method. Northern blots were probed with miR-122 and let7 microRNAs. Ethidium bromide staining of tRNA is shown as a loading control.
Figure 6A:
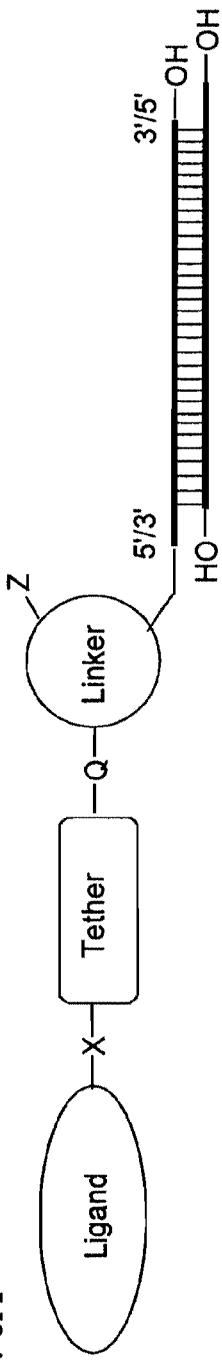
FIG. 6 depicts ligand conjugated double stranded oligonucleotide to modulate expression of miRNA: (a) ligand of interest is conjugated to the oligonucleotide via a tether and linker; (b) ligand of interest is conjugated to the oligonucleotide via a linker without a tether or tether without an additional linker and (c) a ligand of interest is attached directly to the oligonucleotide.
Figure 6B:
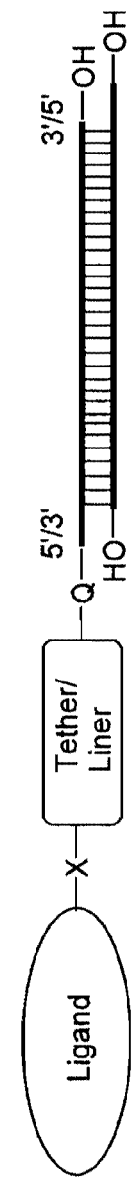
Figure 6C:
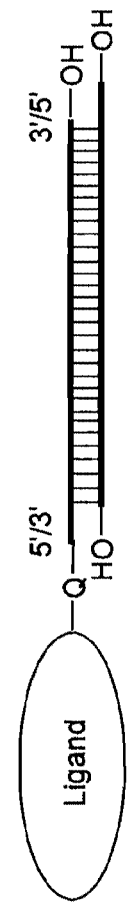
Figure 7:
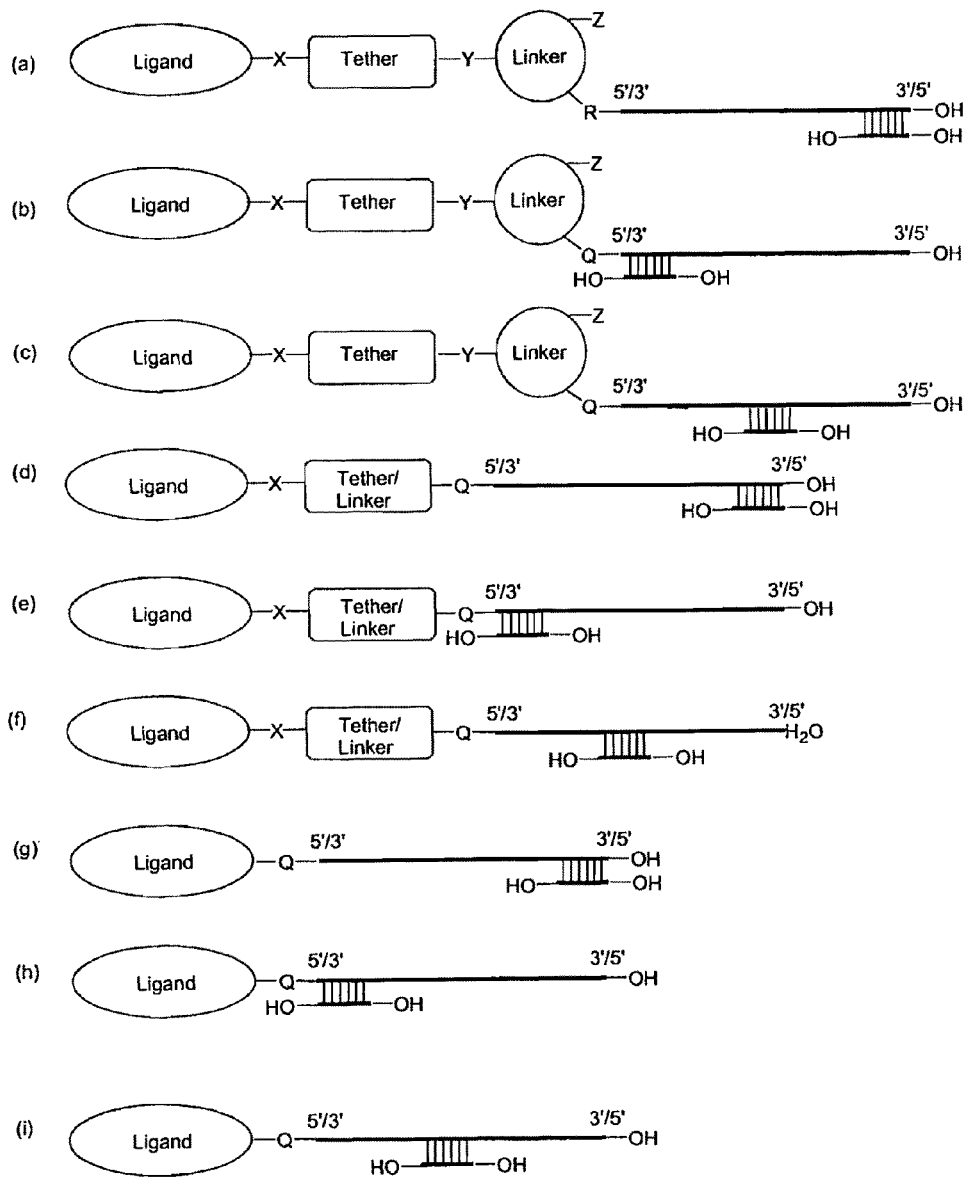
FIG. 7 depicts ligand conjugated antisense strand comprising partially double stranded oligonucleotides to modulate expression of miRNA. (a-c) ligand of interest is conjugated to the oligonucleotide via a tether and linker; (d-f) ligand of interest is conjugated to the oligonucleotide via a linker without a tether or tether without an additional linker and (g-i) a ligand of interest is attached directly to the oligonucleotide.
Figure 8:
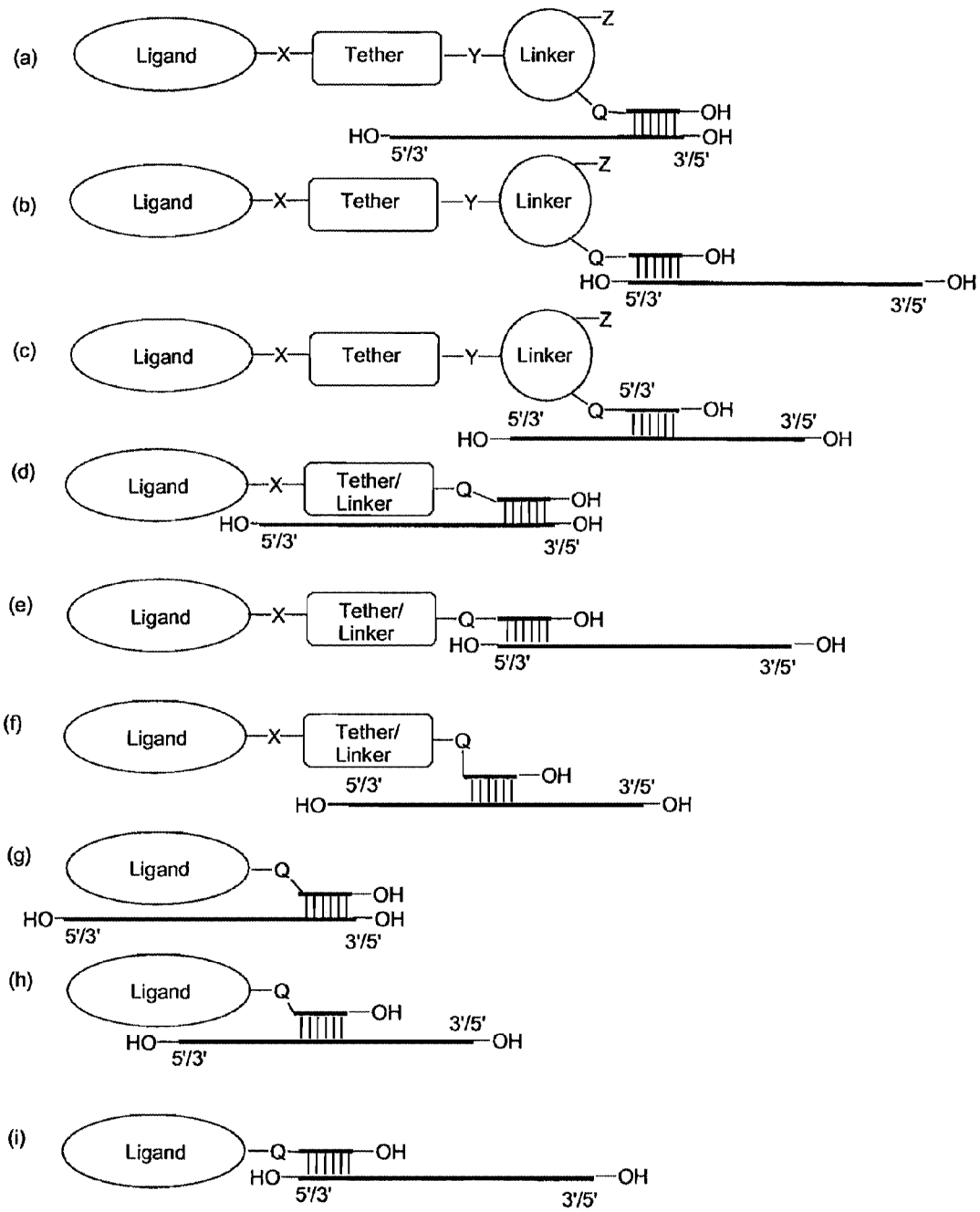
FIG. 8 depicts ligand conjugated partial sense strand comprising partially double stranded oligonucleotides to modulate expression of miRNA. (a-c) ligand of interest is conjugated to the oligonucleotide via a tether and linker; (d-f) ligand of interest is conjugated to the oligonucleotide via a linker without a tether or tether without an additional linker and (g-i) a ligand of interest is attached directly to the oligonucleotide.
Figure 9:
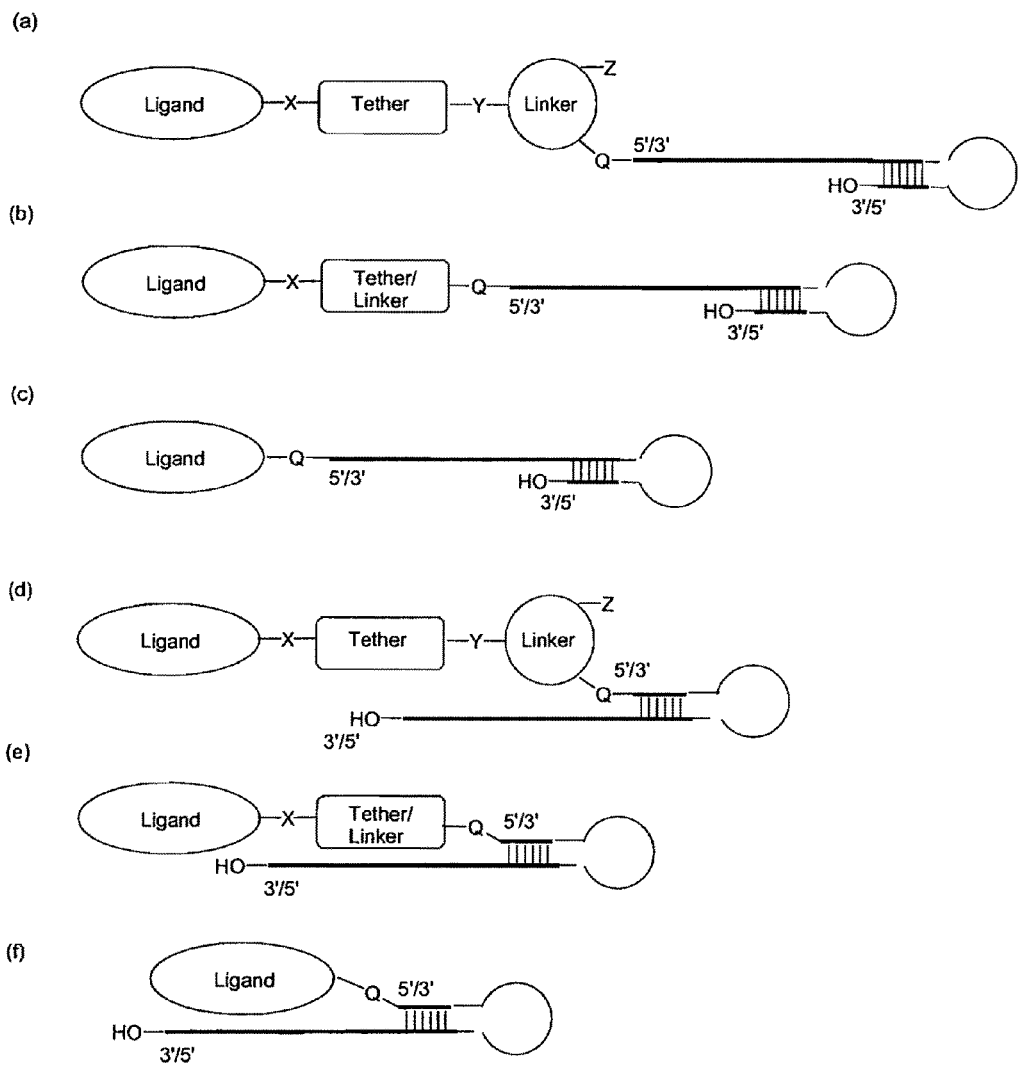
FIG. 9 depicts ligand conjugated partial hairpin oligonucleotides to modulate expression of miRNA. (a-b) ligand of interest is conjugated to either 3' or 5' end of the hairpin via a tether and linker; (c-d) ligand of interest is conjugated to the hairpin via a linker without a tether or tether without an additional linker and (e-f) a ligand of interest is attached directly to the oligonucleotide. The hairpin is comprised of nucleotides or non-nucleotide linkages.

To test the effect of antagomir-122 on miRNA levels in vivo, mice were administered PBS, mm-antagomir-122 or antagomir-122 (80 mg/kg/day) via tail-vein injection for 3 subsequent days. Livers were harvested 24 hrs after the last injection and ~20 mg of tissue was sonicated in 1 ml T+C (Epicentre®, Madison, Wis.) and proteinase K and processed as described in example 4. Precipitated RNA was dissolved in water and analyzed on 14% polyacrylamide gels that contained 20% formamide. Northern blotting was performed for miR-122 and let7 miRNAs. Mice injected with antagomir-122 revealed a striking decrease in the amount of miR-122 isolated from liver, as compared to mice injected with PBS or mm-antagomir-122 (FIG. 4). The level of let7 miRNA isolated from liver was similar in the three test groups.

To test the long-term effect of antagomir-122 on miRNA levels in vivo, mice were administered PBS, mm-antagomir-122 or antagomir-122 (80 mg/kg/day) via tail-vein injection for 3 subsequent days. Livers were then harvested 72 h, 10 days or 27 days after the last injection. Tissues were processed as described in example 4, and Northern blot analysis revealed a marked reduction of miR-122 in the antagomir-treated mice, even 27 days post-injection. As a further note, the Northern blot analysis revealed an RNA of higher molecular weight specifically detected by the miR-122 probe. This molecule is most likely an miR-122 precursor.

Example 6

Dose Response for Antagomir-122

Three groups of mice n=3, C57/B16, female, 6-8 weeks old) were injected with antagomir-122 at a dose of 3×20, 3×40 or 3×80 mg/kg body weight in a total volume of 0.2 ml on three consecutive days. Phosphate buffered saline (PBS) injected mice (3×0.2 ml) served as controls. Mice were sacrificed on day 4 and total RNA was extracted from livers for Northern blotting. Mir-122 expression was analyzed following Northern blotting using a $^{32}$P-labeled oligonucleotide with complementary sequence to miR-122. Expression levels of aldolase A, a validated target gene of miR-122, were analyzed by RT-PCR. Gapdh served as a loading control, Gapdh-RT indicates the absence of reverse transcriptase as a control for DNA contamination.

Figure 13:
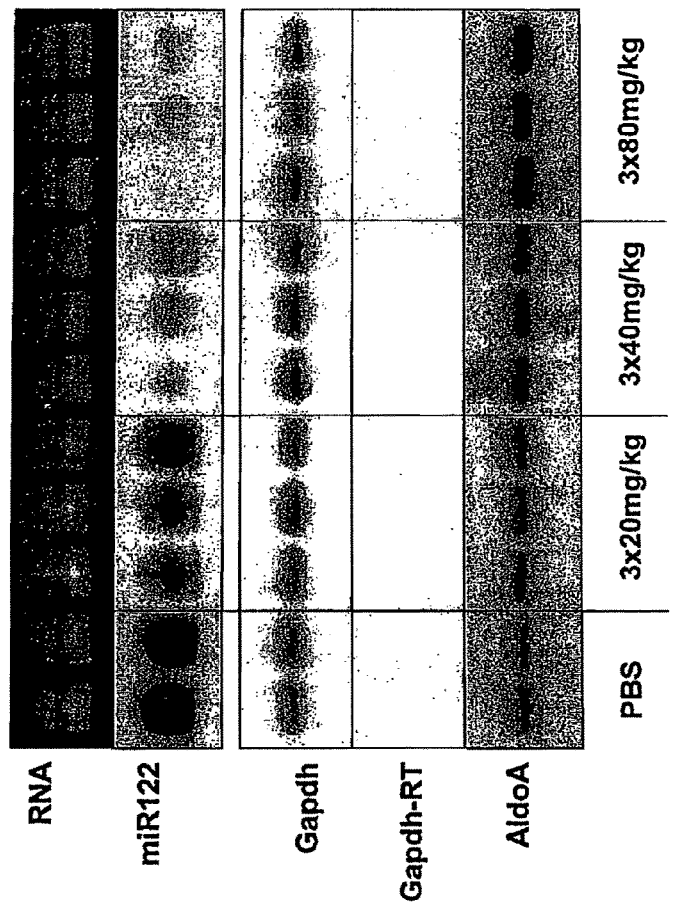
FIG. 13 depicts dose response for antagomir-122.

Results demonstrate that reduction of miR-122 can be achieved at a dose of 3×20 mg/kg bodyweight. A >90% reduction in miR-122 levels is required to detect a significant increase in aldolaseA expression (FIG. 13).

Example 7

Mismatch Control of Antagomir-122 Activity

Five groups of mice n=3, C57/B16, female, 6-8 weeks old) were injected with antagomir-122 harboring 4, 3, 2, 1 or no nucleotide exchange in the sequence of antagomir-122 (4 mm, 3 mm, 2 mm, 1 mm, antagomir-122, respectively). Mice were injected at a dose of 3×80 mg/kg body weight in a total volume of 0.2 ml on three consecutive days. Mice were sacrificed on day 4 and total RNA was extracted from livers for Northern blotting. Mir-122 expression was analyzed by Northern blotting using a $^{32}$P-labeled oligonucleotide with complementary sequence to miR-122.

Figure 14:
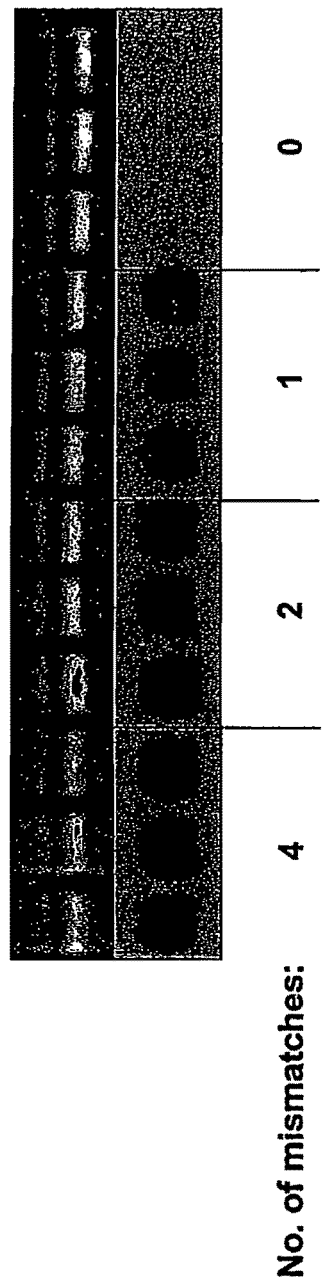
FIG. 14 depicts mismatch control for antagomir-122.

Results demonstrate that 4, 3 (data not shown), or 2 mismatches in antagomir-122 had no effect on miR-122 expression levels. A single mismatch resulted in a 20-30% reduction in miR-122 expression. These data demonstrate that antagomirs have exquisite target specificity (FIG. 14).

```
4 mm:
                                              (SEQ ID NO: 1)
oA*oC*oAoCoAoCoAoAoCoAoCoUoGoUoCoAoCoAoUoU*oC*o
C*oA*-CHOL 3 mm:
                                              (SEQ ID NO: 35)
oA*oC*oAoAoAoCoAoAoCoAoCoUoGoUoCoAoCoAoUoU*oC*o
C*oA*-CHOL 2 mm:
                                              (SEQ ID NO: 36)
oA*oC*oAoAoAoCoAoCoCoAoCoUoGoUoCoAoCoAoUoU*oC*oC*
oA*-CHOL
```

```
1 mm:
                                              (SEQ ID NO: 37)
oA*oC*oAoAoAoCoAoCoCoAoUoUoGoUoCoAoCoAoUoU*oC*oC*
oA*-CHOL

Antagomir-122
                                              (SEQ OD NO: 11)
oA*oC*oAoAoAoCoAoCoCoAoUoUoGoUoCoAoCoAoCoU*oC*oC*o
A*-CHOL
```

Example 8

Length Effect on Antagomir-122 Activity

Six groups of mice (n=3, C57/B16, female, 6-8 weeks old; only n=2 shown) were injected with antagomir-122, which differed in length between 25, 23 (antagomir-122), 21, 19 and 17 bp. Mice were injected at a dose of 3×80 mg/kg body weight in a total volume of 0.2 ml on three consecutive days. Mice were sacrificed on day 4 and total RNA was extracted from livers for Northern blotting. Mir-122 expression was analyzed by Northern blotting using a $^{32}$P-labeled oligonucleotide with complementary sequence to miR-122.

Figure 15:
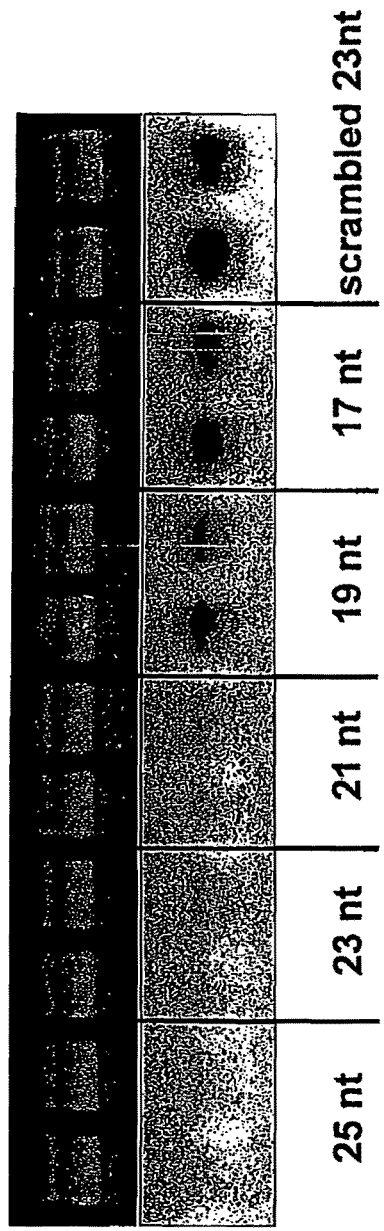
FIG. 15 depicts length effect on activity of antagomir-122.

Results demonstrate that an additional nucleotide at both 3' and 5' ends of antagomir-122 (25-mer), or a deletion at either end (21-mer) has no effect of the ability of antagomirs to silence miR-122. Further shortening of antagomirs (19- and 17-mers) result in a loss of antagomir activity (FIG. 15).

```
Antagomir-122 (23-mer)
                                              (SEQ ID NO: 5)
oA*oC*oAoAoAoCoAoCoCoAoUoUoGoUoCoAoCoAoCoU*oC*o
C*oA*-CHOL 25-mer:
                                              (SEQ ID NO: 31)
oC*oA*oCoAoAoAoCoAoCoCoAoUoUoGoUoCoAoCoAoCoUoC*o
C*oA*oC*-
CHOL 21-mer:
                                              (SEQ ID NO: 32)
oC*oA*oAoAoCoAoCoCoAoUoUoGoUoCoAoCoAoC*oU*oC*oC*-
CHOL 19-mer:
                                              (SEQ ID NO: 33)
oA*oA*oAoCoAoCoCoAoUoUoGoUoCoAoCoA*oC*oU*oC*-CHOL 17-mer:
                                              (SEQ ID NO: 34)
oA*oA*oCoAoCoCoAoUoUoGoUoCoAoC*oA*oC*oU*-CHOL
```

Example 9

Synthesis of Antagomirs

Step 1. Oligonucleotide Synthesis

All oligonucleotides were synthesized on an AKTAoligopilot synthesizer or on an ABI 394 DNA/RNA synthesizer. Commercially available controlled pore glass solid supports (rU-CPG, 2'-O-methly modified rA-CPG and 2'-O-methyl modified rG-CPG from Prime Synthesis) or the in-house synthesized solid support hydroxyprolinol-cholesterol-CPG were used for the synthesis. RNA phosphoramidites and 2'-O-methyl modified RNA phosphoramidites with standard protecting groups (5'-O-dimethoxytrityl-N6-benzoyl-2'-t-butyldimethylsilyl-adenosine-3'-O—N,N'-diisopropyl-2-cyanoethylphosphoramidite, 5'-O-dimethoxytrityl-N4- acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, 5'-O-dimethoxytrityl-2'-t-butyldimethylsilyl-uridine-3'-O—N,N'-diisopropyl-2-cyanoethylphosphoramidite, 5'-O-dimethoxytrityl-N6-benzoyl-2'-O-methyl-adenosine-3'-O—N,N'-diisopropyl-2-cyanoethylphosphoramidite, 5'-O-dimethoxytrityl-N4-acetyl-2'-O-methyl-cytidine-3'-O—N,N'-diisopropyl-2-cyanoethylphosphoramidite, 5'-O-dimethoxytrityl-N2-isobutryl-2'-O-methyl-guanosine-3'-O—N,N'-diisopropyl-2-cyanoethylphosphoramidite, and 5'-O-dimethoxytrityl-2'-O-methyl-uridine-3'-O—N,N'-diisopropyl-2-cyanoethylphosphoramidite) were obtained from Pierce Nucleic Acids Technologies and ChemGenes Research. The Quasar 570 phosphoramidite was obtained from Biosearch Technologies. The 5'-O-dimethoxytrityl-2't-butyldimethylsilyl-inosine-3'O—N,N'-diisopropyl-2-cyanoethylphosphoramidite was obtained from ChemGenes Research. For the syntheses on AKTAoligopilot synthesizer, all phosphoramidites were used at a concentration of 0.2 M in $CH_3CN$ except for guanosine and 2'-O-methyl-uridine, which were used at 0.2 M concentration in 10% $THF/CH_3CN$ (v/v). Coupling/recycling time of 16 minutes was used for all phosphoramidite couplings. The activator was 5-ethyl-thio-tetrazole (0.75 M, American International Chemicals). For the PO-oxidation, 50 mM iodine in water/pyridine (10:90 v/v) was used and for the PS-oxidation 2% PADS (GL Synthesis) in 2,6-lutidine/$CH_3CN$ (1:1 v/v) was used. For the syntheses on ABI 394 DNA/RNA synthesizer, all phosphoramidites were used at a concentration of 0.15 M in $CH_3CN$ except for 2'-O-methyl-uridine, which was used at 0.15 M concentration in 10% $THF/CH_3CN$ (v/v). Coupling time of 10 minutes was used for all phosphoramidite couplings. The activator was 5-ethyl-thio-tetrazole (0.25 M, Glen Research). For the PO-oxidation, 20 mM iodine in water/pyridine (Glen Research) was used and for the PS-oxidation 0.1M DDTT (AM Chemicals) in pyridine was used. Coupling of the Quasar 570 phosphoramidite was carried out on the ABI DNA/RNA synthesizer. The Quasar 570 phosphoramidite was used at a concentration of 0.1M in $CH_3CN$ with a coupling time of 10 mins. The activator was 5-ethyl-thio-tetrazole (0.25 M, Glen Research) and 0.1M DDTT (AM Chemicals) in pyridine was used for PS oxidation.

Step 2. Deprotection of Oligonucleotides

A. Sequences Synthesized on the AKTAoligopilot Synthesizer

After completion of synthesis, the support was transferred to a 100 mL glass bottle (VWR). The oligonucleotide was cleaved from the support with simultaneous deprotection of base and phosphate groups with 40 mL of a 40% aq. methyl amine (Aldrich) 90 mins at 45° C. The bottle was cooled briefly on ice and then the methylamine was filtered into a new 500 mL bottle. The CPG was washed three times with 40 mL portions of DMSO. The mixture was then cooled on dry ice.

In order to remove the tert-butyldimethylsilyl (TBDMS) groups at the 2' position, 60 mL triethylamine trihydrofluoride (Et3N-HF) was added to the above mixture. The mixture was heated at 40° C. for 60 minutes. The reaction was then quenched with 220 mL of 50 mM sodium acetate (pH 5.5) and stored in the freezer until purification.

B. Sequences Synthesized on the ABI DAN/RNA Synthesizer

After completion of synthesis, the support was transferred to a 15 mL tube (VWR). The oligonucleotide was cleaved from the support with simultaneous deprotection of base and phosphate groups with 7 mL of a 40% aq. methyl amine (Aldrich) 15 mins at 65° C. The bottle was cooled briefly on ice and then the methylamine was filtered into a 100 mL bottle (VWR). The CPG was washed three times with 7 mL portions of DMSO. The mixture was then cooled on dry ice.

In order to remove the tert-butyldimethylsilyl (TBDMS) groups at the 2' position, 10.5 mL triethylamine trihydrofluoride (Et3N-HF) was added to the above mixture. The mixture was heated at 60° C. for 15 minutes. The reaction was then quenched with 38.5 mL of 50 mM sodium acetate (pH 5.5) and stored in the freezer until purification.

Step 3. Quantitation of Crude Oligonucleotides

For all samples, a 10 μL aliquot was diluted with 990 μL of deionised nuclease free water (1.0 mL) and the absorbance reading at 260 nm was obtained.

Step 4. Purification of Oligonucleotides (a) Unconjugated Oligonucleotides

The unconjugated crude oligonucleotides were first analyzed by HPLC (Dionex PA 100). The buffers were 20 mM phosphate, pH 11 (buffer A); and 20 mM phosphate, 1.8 M NaBr, pH 11 (buffer B). The flow rate 1.0 mL/min and monitored wavelength was 260-280 nm. Injections of 5-15 μL were done for each sample.

The unconjugated samples were purified by HPLC on a TSK-Gel SuperQ-5PW (20) column packed in house (17.3×5 cm) or on a commercially available TSK-Gel SuperQ-5PW column (15×0.215 cm) available from TOSOH Bioscience. The buffers were 20 mM phosphate in 10% $CH_3CN$, pH 8.5 (buffer A) and 20 mM phosphate, 1.0 M NaBr in 10% $CH_3CN$, pH 8.5 (buffer B). The flow rate was 50.0 mL/min for the in house packed column and 10.0 ml/min for the commercially obtained column. Wavelengths of 260 and 294 nm were monitored. The fractions containing the full-length oligonucleotides were pooled together, evaporated, and reconstituted to ~100 mL with deionised water.

(b) Cholesterol-Conjugated Oligonucleotides

The cholesterol-conjugated crude oligonucleotides were first analyzed by LC/MS to determine purity. The cholesterol conjugated sequences were HPLC purified on RPC-Sourcel 5 reverse-phase columns packed in house (17.3×5 cm or 15×2 cm). The buffers were 20 mM NaOAc in 10% $CH_3CN$ (buffer A) and 20 mM NaOAc in 70% $CH_3CN$ (buffer B). The flow rate was 50.0 mL/min for the 17.3×5 cm column and 12.0 ml/min for the 15×2 cm column. Wavelengths of 260 and 284 nm were monitored. The fractions containing the full-length oligonucleotides were pooled, evaporated, and reconstituted to 100 mL with deionised water.

Step 5. Desalting of Purified Oligonucleotides

The purified oligonucleotides were desalted on either an AKTA Explorer or an AKTA Prime system (Amersham Biosciences) using a Sephadex G-25 column packed in house. First, the column was washed with water at a flow rate of 40 mL/min for 20-30 min. The sample was then applied in 40-60 mL fractions. The eluted salt-free fractions were combined, dried, and reconstituted in ~50 mL of RNase free water.

Step 6. Purity Analysis by Capillary Gel Electrophoresis (CGE), Ion-Exchange HPLC (IEX), and Electrospray LC/Ms Approximately 0.3 OD of each of the desalted oligonucleotides were diluted in water to 300 μL and were analyzed by CGE, ion exchange HPLC, and LC/MS.

Step 7. Duplex Formation

For the fully double stranded duplexes, equal amounts, by weight, of two RNA strands were mixed together. The mixtures were frozen at −80° C. and dried under vacuum on a speed vac. Dried samples were then dissolved in 1× PBS to a final concentration of 40 mg/ml. The dissolved samples were heated to 95° C. for 5 min and slowly cooled to room temperature.

TABLE 4 oligonucleotides synthesized to modulate microRNAs (SEQ ID NOs 1, 12, 10, 11, 13, 14, 21-37, 39, 30 and 10 respectively)

| AL-SQ # | Sequence | Target | Calc Mass | Found Mass | Purity (%) |
|---|---|---|---|---|---|
| 3035 | UGG AGU GUG ACA AUG GUG UUU GU | miR-122A | 7422.44 | 7422.20 | 94.1* |
| 3036 | UGG AAU GUG ACA GUG UUG UGU GU | miR-122A | 7422.42 | 7422.24 | 95.3* |
| 3037 | $A_{OMe}sC_{OMe}sA_{OMe}sA_{OMe}sA_{OMe}sC_{OMe}sA_{OMe}sC_{OMe}sC_{OMe}sA_{OMe}sU_{OMe}sU_{OMe}sG_{OMe}sU_{OMe}sC_{OMe}sA_{OMe}sC_{OMe}sA_{OMe}sC_{OMe}sU_{OMe}sC_{OMe}sC_{OMe}sA_{OMe}s$-Chol | miR-122A | 8613.43 | 8614.53 | 82.7 |
| 3038 | $A_{OMe}sC_{OMe}sA_{OMe}A_{OMe}A_{OMe}C_{OMe}A_{OMe}C_{OMe}C_{OMe}A_{OMe}U_{OMe}U_{OMe}G_{OMe}U_{OMe}C_{OMe}A_{OMe}C_{OMe}A_{OMe}C_{OMe}U_{OMe}sC_{OMe}sC_{OMe}sA_{OMe}s$-Chol | miR-122A | 8340.09 | 8341.23 | 99.2 |
| 3039 | $A_{OMe}sC_{OMe}sA_{OMe}sC_{OMe}sA_{OMe}sC_{OMe}sA_{OMe}sA_{OMe}sC_{OMe}sA_{OMe}sC_{OMe}sU_{OMe}sG_{OMe}sU_{OMe}sC_{OMe}sA_{OMe}sC_{OMe}sA_{OMe}sU_{OMe}sU_{OMe}sC_{OMe}sC_{OMe}sA_{OMe}s$-Chol | miR-122A | 8613.43 | 8614.75 | 86.6 |
| 3040 | $A_{OMe}sC_{OMe}sA_{OMe}C_{OMe}A_{OMe}C_{OMe}A_{OMe}A_{OMe}C_{OMe}A_{OMe}C_{OMe}U_{OMe}G_{OMe}U_{OMe}C_{OMe}A_{OMe}C_{OMe}A_{OMe}U_{OMe}U_{OMe}sC_{OMe}sC_{OMe}sA_{OMe}s$-Chol | miR-122A | 8340.09 | 8341.15 | 85.2 |
| 3223 | $U_{OMe}sG_{OMe}sG_{OMe}A_{OMe}G_{OMe}U_{OMe}G_{OMe}U_{OMe}G_{OMe}A_{OMe}C_{OMe}A_{OMe}A_{OMe}U_{OMe}G_{OMe}G_{OMe}U_{OMe}G_{OMe}U_{OMe}U_{OMe}sU_{OMe}sG_{OMe}sU_{OMe}s$-Chol | miR-122A | 8545.13 | 8546.19 | 95.8 |
| 3224 | $U_{OMe}sG_{OMe}sG_{OMe}A_{OMe}A_{OMe}U_{OMe}G_{OMe}U_{OMe}G_{OMe}A_{OMe}C_{OMe}A_{OMe}G_{OMe}U_{OMe}G_{OMe}U_{OMe}U_{OMe}G_{OMe}U_{OMe}sG_{OMe}sU_{OMe}s$-Chol | miR-122A | 8545.13 | 8546.28 | 92.3 |
| 3225 | $A_{OMe}sC_{OMe}sA_{OMe}sA_{OMe}sA_{OMe}sC_{OMe}sA_{OMe}sC_{OMe}sC_{OMe}sA_{OMe}sU_{OMe}sU_{OMe}sG_{OMe}sU_{OMe}sC_{OMe}sA_{OMe}sC_{OMe}sA_{OMe}sC_{OMe}sU_{OMe}sC_{OMe}sC_{OMe}sA_{OMe}$ | miR-122A | 7892.09 | 7892.92 | 84.0 |
| 3226 | $A_{OMe}sC_{OMe}sA_{OMe}A_{OMe}A_{OMe}C_{OMe}A_{OMe}C_{OMe}C_{OMe}A_{OMe}U_{OMe}U_{OMe}G_{OMe}U_{OMe}C_{OMe}A_{OMe}C_{OMe}A_{OMe}C_{OMe}U_{OMe}sC_{OMe}sC_{OMe}sA_{OMe}$ | miR-122A | 7604.09 | 7604.04 | 81.5 |
| 3227 | $C_{OMe}sG_{OMe}sC_{OMe}C_{OMe}A_{OMe}A_{OMe}U_{OMe}A_{OMe}U_{OMe}U_{OMe}U_{OMe}A_{OMe}C_{OMe}G_{OMe}U_{OMe}G_{OMe}C_{OMe}U_{OMe}G_{OMe}sC_{OMe}sU_{OMe}sA_{OMe}s$-chol | miR-16 | 8047.82 | 8048.88 | 94.0* |
| 3228 | $G_{OMe}sG_{OMe}sC_{OMe}U_{OMe}G_{OMe}U_{OMe}C_{OMe}A_{OMe}A_{OMe}U_{OMe}U_{OMe}C_{OMe}A_{OMe}U_{OMe}A_{OMe}G_{OMe}G_{OMe}U_{OMe}C_{OMe}A_{OMe}sG_{OMe}s$-Chol | miR-192 | 7807.68 | 7808.49 | 97.1* |
| 3229 | $U_{OMe}sC_{OMe}sC_{OMe}A_{OMe}C_{OMe}A_{OMe}U_{OMe}G_{OMe}G_{OMe}A_{OMe}G_{OMe}U_{OMe}U_{OMe}G_{OMe}C_{OMe}U_{OMe}G_{OMe}U_{OMe}U_{OMe}A_{OMe}sC_{OMe}sA_{OMe}s$-Chol | miR-194 | 8088.84 | 8089.69 | 92.7* |
| 3230 | $U_{OMe}sC_{OMe}sA_{OMe}C_{OMe}G_{OMe}C_{OMe}G_{OMe}A_{OMe}G_{OMe}C_{OMe}C_{OMe}G_{OMe}A_{OMe}A_{OMe}C_{OMe}G_{OMe}A_{OMe}A_{OMe}C_{OMe}sA_{OMe}sA_{OMe}sA_{OMe}s$-Chol | miR-375 | 8178.03 | 8178.77 | 100* |
| 3344 | UGG IGU GUG ICI IUG GUG UUU GU | miR-122A | 7120.19 | 7119.36 | 83.0* |
| 3350 | $A_{OMe}C_{OMe}A_{OMe}A_{OMe}A_{OMe}C_{OMe}A_{OMe}C_{OMe}C_{OMe}A_{OMe}U_{OMe}U_{OMe}G_{OMe}U_{OMe}C_{OMe}A_{OMe}C_{OMe}A_{OMe}C_{OMe}U_{OMe}C_{OMe}C_{OMe}A_{OMe}$-Chol | miR-122A | 8244.09 | 8244.13 | 8.0* |
| 3351 | $C_{OMe}sA_{OMe}sC_{OMe}A_{OMe}A_{OMe}A_{OMe}C_{OMe}A_{OMe}C_{OMe}C_{OMe}A_{OMe}U_{OMe}U_{OMe}G_{OMe}U_{OMe}C_{OMe}A_{OMe}C_{OMe}A_{OMe}C_{OMe}U_{OMe}sC_{OMe}sA_{OMe}sC_{OMe}s$-Chol | miR-122A | 8978.51 | 8979.07 | 97.1* |
| 3352 | $C_{OMe}sA_{OMe}sA_{OMe}A_{OMe}C_{OMe}A_{OMe}C_{OMe}C_{OMe}A_{OMe}U_{OMe}U_{OMe}G_{OMe}U_{OMe}C_{OMe}A_{OMe}C_{OMe}A_{OMe}sU_{OMe}sC_{OMe}sC_{OMe}s$-Chol | miR-122A | 7653.61 | 7653.92 | 89.0* |
| 3353 | $A_{OMe}sA_{OMe}sA_{OMe}C_{OMe}A_{OMe}C_{OMe}C_{OMe}A_{OMe}U_{OMe}U_{OMe}G_{OMe}U_{OMe}C_{OMe}A_{OMe}C_{OMe}A_{OMe}sC_{OMe}sU_{OMe}sC_{OMe}s$-Chol | miR-122A | 7015.19 | 7015.7 | 97.9* |
| 3354 | $A_{OMe}sA_{OMe}sC_{OMe}A_{OMe}C_{OMe}C_{OMe}A_{OMe}U_{OMe}U_{OMe}G_{OMe}U_{OMe}C_{OMe}A_{OMe}C_{OMe}sA_{OMe}sC_{OMe}sU_{OMe}s$-Chol | miR-122A | 6352.74 | 6353.29 | 97.9* |
| 3355 | $A_{OMe}sC_{OMe}sA_{OMe}A_{OMe}C_{OMe}A_{OMe}A_{OMe}A_{OMe}C_{OMe}A_{OMe}C_{OMe}C_{OMe}A_{OMe}U_{OMe}G_{OMe}U_{OMe}C_{OMe}A_{OMe}C_{OMe}A_{OMe}U_{OMe}sC_{OMe}sC_{OMe}sA_{OMe}s$-Chol | miR-122A | 8364.13 | 8364.45 | 90.2* |
| 3356 | $A_{OMe}sC_{OMe}sA_{OMe}A_{OMe}A_{OMe}C_{OMe}A_{OMe}C_{OMe}C_{OMe}A_{OMe}C_{OMe}U_{OMe}G_{OMe}U_{OMe}C_{OMe}A_{OMe}C_{OMe}A_{OMe}U_{OMe}U_{OMe}sC_{OMe}sC_{OMe}sA_{OMe}s$-Chol | miR-122A | 8340.09 | 8340.46 | 86.0* |

TABLE 4-continued oligonucleotides synthesized to modulate microRNAs (SEQ ID NOs 1, 12, 10, 11, 13, 14, 21-37, 39, 30 and 10 respectively)

| AL-SQ # | Sequence | Target | Calc Mass | Found Mass | Purity (%) |
|---|---|---|---|---|---|
| 3357 | $A_{OMe}sC_{OMe}sA_{OMe}A_{OMe}A_{OMe}C_{OMe}A_{OMe}C_{OMe}C_{OMe}A_{OMe}U_{OMe}U_{OMe}$ $G_{OMe}U_{OMe}C_{OMe}A_{OMe}C_{OMe}A_{OMe}U_{OMe}U_{OMe}sC_{OMe}sC_{OMe}sA_{OMe}s$-Chol | miR-122A | 8341.08 | 8341.43 | 79.0* |
| 3359 | Quasar5s$A_{OMe}sC_{OMe}A_{OMe}C_{OMe}A_{OMe}C_{OMe}A_{OMe}A_{OMe}C_{OMe}A_{OMe}C_{OMe}$ $U_{OMe}G_{OMe}U_{OMe}C_{OMe}A_{OMe}C_{OMe}A_{OMe}U_{OMe}U_{OMe}sC_{OMe}sC_{OMe}sA_{OMe}$s-Chol | miR-122A | 8960.91 | 8960.78 | 93.0* |
| 3383 | $A_{OMe}C_{OMe}A_{OMe}A_{OMe}A_{OMe}C_{OMe}A_{OMe}C_{OMe}C_{OMe}A_{OMe}U_{OMe}U_{OMe}G_{OMe}$ $U_{OMe}C_{OMe}A_{OMe}C_{OMe}A_{OMe}C_{OMe}U_{OMe}C_{OMe}C_{OMe}A_{OMe}$s-Chol | miR-122A | 8260.09 | 8260.13 | 86.0* |
| 3474 | Quasar5s$A_{OMe}sC_{OMe}A_{OMe}A_{OMe}A_{OMe}C_{OMe}A_{OMe}C_{OMe}C_{OMe}A_{OMe}U_{OMe}$ $U_{OMe}G_{OMe}U_{OMe}C_{OMe}A_{OMe}C_{OMe}A_{OMe}C_{OMe}U_{OMe}sC_{OMe}sC_{OMe}sA_{OMe}$s-Chol | miR-122A | 8960.91 | 8960.65 | 98.9* |

The strands are shown written 5' to 3'. Lower case "s" indicates a phosphorothioate linkage. "Chol-" indicates a hydroxyprolinol cholesterol conjugate. Subscript "OMe" indicates a 2'-O-methyl sugar. "I" is ribo-Inosine nucleoside. Purity was determined by CGE except for the where indicated by (*), in these cases purity was determined by anion-exchange HPLC.

TABLE 5

Double stranded oligonucleotides to modulate microRNAs

| AL-DP # | Strand 1 | Strand 2 | Target |
|---|---|---|---|
| 3018 | AL-SQ-3035 | AL-SQ-3037 | miR-122A |
| 3019 | AL-SQ-3035 | AL-SQ-3038 | miR-122A |
| 3020 | AL-SQ-3036 | AL-SQ-3039 | miR-122A |
| 3021 | AL-SQ-3036 | AL-SQ-3040 | miR-122A |

TABLE 6

Description of oligonucleotides synthesized to modulate microRNAs

| Sequence # | Description |
|---|---|
| 3035 | complementary to antagomir-122 |
| 3036 | complementary to mm-antagomir-122 |
| 3037 | antagomir-122-fullyPS |
| 3038 | antagomir-122 |
| 3039 | mm-antagomir-122-fullyPS |
| 3040 | mm-antagomir-122 |
| 3223 | complementary to antagomir-122 |
| 3224 | complementary to mm-antagomir-122 |
| 3225 | anti-122-fully-PS |
| 3226 | anti-122-partial_PS |
| 3227 | antagomir-16 |
| 3228 | antagomir-192 |
| 3229 | antagomir-194 |
| 3230 | antagomir-375 |
| 3344 | complementary to antagomir-122 with Adenosine -> Inosine modification |
| 3350 | antagomir-122-noPS |
| 3351 | antagomir-122-25mer |
| 3352 | antagomir-122-21mer |
| 3353 | antagomir-122-19mer |
| 3354 | antagomir-122-17mer |
| 3355 | mm-antagomir-122-3mm |
| 3356 | mm-antagomir-122-2mm |
| 3357 | mm-antagomir-122-1mm |
| 3359 | mm-antagomir-122-5'-Quasar570 |
| 3383 | Same as AL-3350 with P=S between 3'-end and Cholesterol |
| 3474 | antagomir-122-5'-Quasar570 |

Example 10

Characterization of Antagomirs

The following experiments were designed to further characterize the properties and function of antagomirs in mice. The results presented herein demonstrate that antagomirs that have optimized phosphorothioate modification and are preferably greater than 19 nucleotides in length exhibit the highest biological efficiency, and can discriminate between single nucleotide mismatches of the targeted miRNA.

The observation that degradation of different chemically protected miRNA/antagomir duplexes in mouse livers and localization of antagomirs in a cytosolic compartment that is distinct from processing (P)-bodies indicates a degradation mechanism independent of the RNA interference (RNAi) pathway.

It was also observed that although antagomirs are incapable of silencing miRNAs in the central nervous system (CNS) when injected systemically, the antagomirs efficiently targeted miRNAs in the CNS when injected locally into the mouse cortex. The data presented herein further validate the effectiveness of antagomirs in vivo, particularly in clinically relevant settings.

The materials and methods employed in the experiments disclosed herein are now described.

Synthesis of Antagomirs

Figure 16:
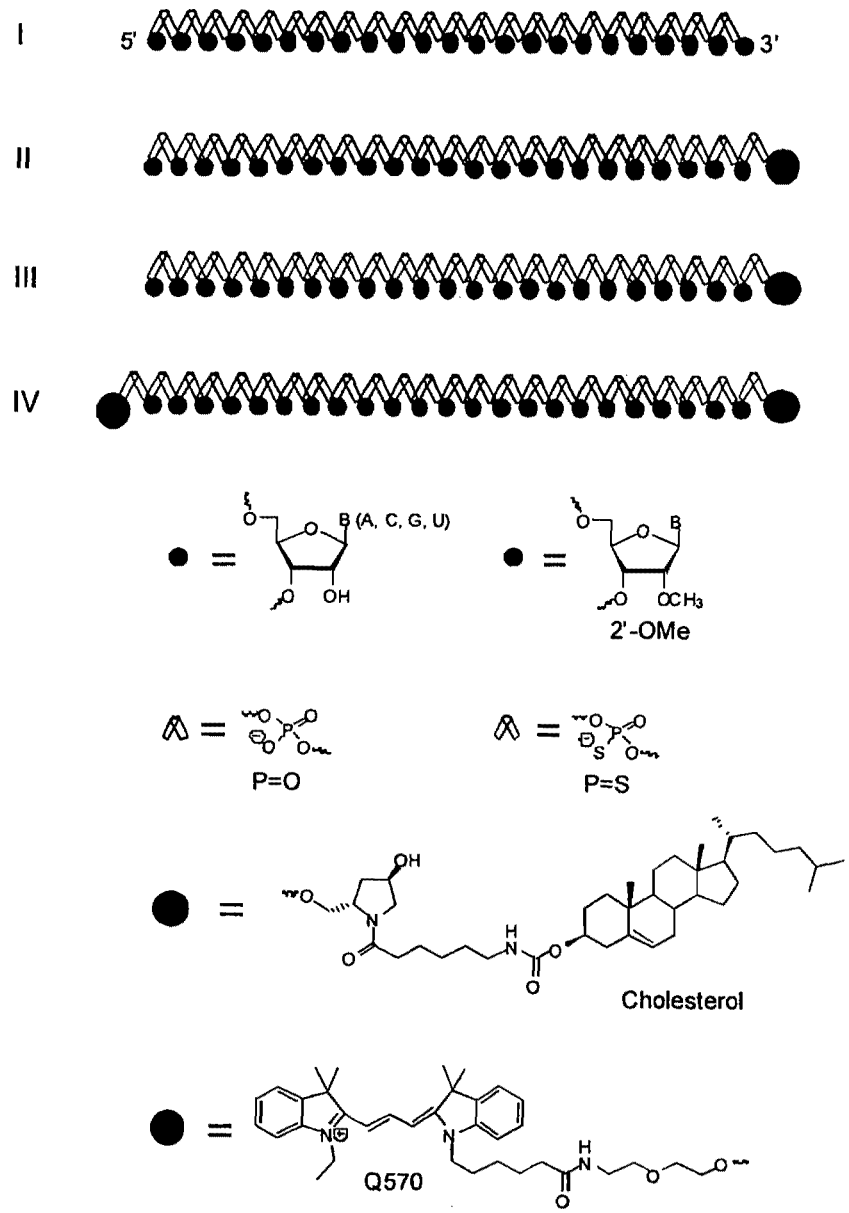
FIG. 16 is a schematic representation of various chemical modifications to an antagomir. The designation of (I), (II), (III), and (IV) corresponds to miR-122, antagomir-122, antagomir-122 all P=S and 5'-Quasar570 labeled antagomir-122, respectively.

Single-stranded RNAs and modified RNA analogs (antagomirs) were synthesized as previously elsewhere herein. The oligonucleotides used in this study are listed in Table 7 and a schematic representation of the chemical modifications is shown in FIG. 16. Quasar-570 (Q570) phosphoramidite from Biosearch Technologies was coupled to the 5'-terminal under standard solid phase phosphoramidite synthesis conditions to obtain fluorophore tagged antagomir 122 and mm-antagomir-122. Extended 15 minute coupling of quasar-570 phosphoramidite was carried out at a concentration of 0.1M in $CH_3CN$ in the presence of 5-(ethylthio)-1H-tetrazole activator followed by standard capping, oxidation and deprotection afforded labeled oligonucleotides. The Q570 conjugated sequences were HPLC purified on an in-house packed RPC-Sourcel 5 reverse-phase column. The buffers were 20 mM NaOAc in 10% $CH_3CN$ (buffer A) and 20 mM NaOAc in 70%

CH₃CN (buffer B). Fractions containing full-length oligonucleotides were pooled and desalted. Analytical HPLC, CGE and ES LC-MS established the integrity of the compounds. For duplex generation, equal molar mounts of miR-122 and antagomir were heated in 1× PBS at 95° C. for 5 minutes and slowly cooled to room temperature.

Northern Blotting Analysis

Total RNA was isolated using the Trizol protocol with ethanol precipitation and Northern blot analysis was performed using formamide-containing PAGE as described elsewhere herein.

RT-PCR

TABLE 7*

Antagomirs of mir-122 and mir-16

| S. No | Sequence | Description |
|---|---|---|
| 1 | 5'-UGGAGUGUGACAAUGGUGUUUGU-3' | Mir-122 |
| 5 | 5'-a$_s$c$_s$aaacaccåugucacåu$_s$c$_s$c$_s$a$_s$-Chol-3' | Antagomir-122 (23nt, 6xP=S) |
| 31 | 5'-c$_s$a$_s$caaacaccauugucacacuc$_s$c$_s$a$_s$c$_s$-Chol-3' | Antagomir-122 (25nt, 6xP=S) |
| 32 | 5'-c$_s$a$_s$aacaccauugucacac$_s$u$_s$c$_s$c$_s$-Chol-3' | Antagomir-122 (21nt, 6xP=S) |
| 33 | 5'-a$_s$a$_s$acaccauugucaca$_s$c$_s$u$_s$c$_s$-Chol-3' | Antagomir-122 (19nt, 6xP=S) |
| 34 | 5'-a$_s$a$_s$caccauugucac$_s$a$_s$c$_s$u$_s$-Chol-3' | Antagomir-122 (17nt, 6xP=S) |
| 30 | 5'-acaaacaccauugucacacucca-Chol-3' | Antagomir-122 (23nt, no P=S) |
| 45 | 5'-acaaacaccauugucacacucca$_s$-Chol-3' | Antagomir-122, (23nt, 1xP=S) |
| 9 | 5'-a$_s$c$_s$a$_s$a$_s$a$_s$c$_s$a$_s$c$_s$c$_s$a$_s$u$_s$u$_s$g$_s$u$_s$c$_s$a$_s$c$_s$a$_s$c$_s$u$_s$c$_s$c$_s$a$_s$-Chol-3' | Antagomir-122, (23nt, 23xP=S) |
| 14 | 5'-a$_s$c$_s$acacaacacugucacauu$_s$c$_s$c$_s$a$_s$-Chol-3' | mm-antagomir-122 (23nt, 6xP=S, 4 mm) |
| 36 | 5'-a$_s$c$_s$aaacaccåugucacåu$_s$c$_s$c$_s$a$_s$-Chol-3' | mm-antagomir-122 (23nt, 6xP=S, 2 mm) |
| 37 | 5'-a$_s$c$_s$aaacaccauugucacåu$_s$c$_s$c$_s$a$_s$-Chol-3' | mm-antagomir-122 (23nt, 6xP=S, 1 mm at nt19) |
| 46 | 5'-å̊c$_s$aaacaccauugucacacu$_s$c$_s$c$_s$a$_s$-Chol-3' | mm-antagomir-122 (23nt, 6xP=S, 1 mm at nt1) |
| 47 | 5'-a$_s$c$_s$aaacaccåugucacacu$_s$c$_s$c$_s$a$_s$-Chol-3' | mm-antagomir-122 (23nt, 6xP=S, 1 mm at nt11) |
| 48 | 5'-UGGAGUGUGACAauGGUGUUUGU-3' | miR-122 (2'-O-Me at 10 & 11) |
| 49 | 5'-U$_s$G$_s$GAGUGUGACAAUGGUGUUU$_s$G$_s$U-3' | miR-122 (2xP=S at each end) |
| 50 | 5'-Q570$_s$-a$_s$caaacaccauugucacacu$_s$c$_s$c$_s$a$_s$-Chol-3' | Antagomir-122 (5'-Quasar570) |
| 51 | 5'-Q570$_s$-a$_s$cacacaacacugucacauu$_s$c$_s$c$_s$a$_s$-Chol-3' | mm-antagomir-122 (4 mm, 5'-Quasar570) |
| 6 | 5'-c$_s$g$_s$ccaauauuuacgugcug$_s$c$_s$u$_s$a$_s$-Chor-3' | Antagomir-16 |

*Lower case letters indicate 2'-O-methyl-modified nucleotides; subscript 's' indicates a phosphorothioate linkage and 'chol' represents cholesterol linked through a hydroxyprolinol linkage.

Animals

All animals were maintained in a C57Bl/6J background on a 12 hour light/dark cycle in a pathogen-free animal facility at Rockefeller University. Six-week-old mice received on three consecutive days tail vein injections of saline or different RNAs in 0.2 ml per injection at normal pressure. Liver tissue was harvested 24 hours after the last injection or as otherwise indicated.

For cerebral injections, mice were anaesthetized and antagomir-16 was injected into the left frontal cortex (~800 ng). Injections of equal volume PBS into the contralateral area of the right hemisphere served as controls. After 72 hours, mice were sacrificed, blood was removed through systemic perfusion of the left ventricle with PBS and a ~0.4 cm³ area surrounding the injection site was excised from the cortex for analysis.

Extraction of total RNA, synthesis of cDNA, and PCR were performed as described elsewhere herein.

Sucrose Density Gradient Fractionation of Liver Homogenates

Mice were perfused with ice-cold PBS through the left ventricle and ~100 mg liver tissue excised. Cells were fractionated on continuous sucrose density gradients from 0.4-2M. Fractions were separated on 14% PAGE containing 8M urea and 20% formamide. Concentration of 5'-Q570-labeled antagomir in liver fractions was measured using an fmax spectrophotometer from Molecular devices.

Immunofluorescence

For immunofluorescence of P-bodies and antagomirs, 1 mg of Q570-labeled antagomirs were injected in 0.2 ml and normal pressure on day 1, followed by injection of 50 µg of a Gfp-GW182-expressing DNA-plasmid (10) in 2 ml PBS and high pressure on day 2. On day 3, mice were anesthetized and perfused through the left ventricle with 2% paraformaldehyde. Livers were incubated overnight at 4° C. in 4% paraformaldehyde, followed by a 16 hour incubation period in 30% sucrose/PBS (v/v). Frozen sections (7 μm) were mounted on glass slides and analyzed using a laser-scanning microscope.

Statistical Analysis

Results are given as means±standard errors. Statistical analysis was performed with Student's t-test, and the null hypothesis was rejected at the 0.05 level. Results are typically presented as means±standard errors.

The results of the experiments presented in this Example are now described.

Phosphorothioate Modifications and Length of Antagomir-122

The antagomir-122 chemistry includes 6 phosphorothioate backbone modifications. Two phosphorothioates are located at the 5'-end and four at the 3'-end. The following experiment was designed to test whether the number of phosphorothioates is critical for the ability of antagomir-122 to silence miR-122. Four different antagomir-122 molecules that only differ in the number of phosphorothioate modification (P=S) were compared. Injection of antagomir-122 at 3×20 mg/kg bw with no P=S into mice did not influence miR-122 levels in the liver (FIG. 17A). The addition of a single P=S did not significantly alter miR-122 levels as compared to the antagomir-122 with six P=S (FIG. 17B). Complete P=S modification of the antagomir-122 did not further increase the effect on miR-122 levels (FIG. 17B). These results demonstrate that phosphorothioates are important for antagomir-122 function. However, it was observed that complete replacement of P=O by P=S decreases its efficiency. Without wishing to be bound by any particular theory, the result can be explained by the enhanced stability provided by the terminal P=S linked antagomir and the reduced thermodynamic stability of the fully modified P=S antagomir duplex with targeted miRNA.

Experiments were also designed to determine the optimal nucleotide length of antagomirs for silencing endogenous miR-122 levels in vivo. It was observed that the addition of two nucleotides or shortening of antagomir-122 by two nucleotides did not significantly alter its efficiency (FIG. 17C). However, silencing of miR-122 was abolished at 3×20 mg/kg bw when the length of antagomir-122 was reduced to 19 nucleotides. Together, these results demonstrate a preferred optimal number of phosphorothioate modifications and minimum length of antagomirs for their biological function in vivo. Without wishing to be bound by any particular theory, it is believed that the tendency for improved activity of 25 mer antagomir can be explained on the basis of improved thermodynamic binding affinity of the 25 mer, which should also have higher biostability from exonucleases for the core 23 mer.

Dose- and Time Dependency of Antagomir-122

Figure 18:
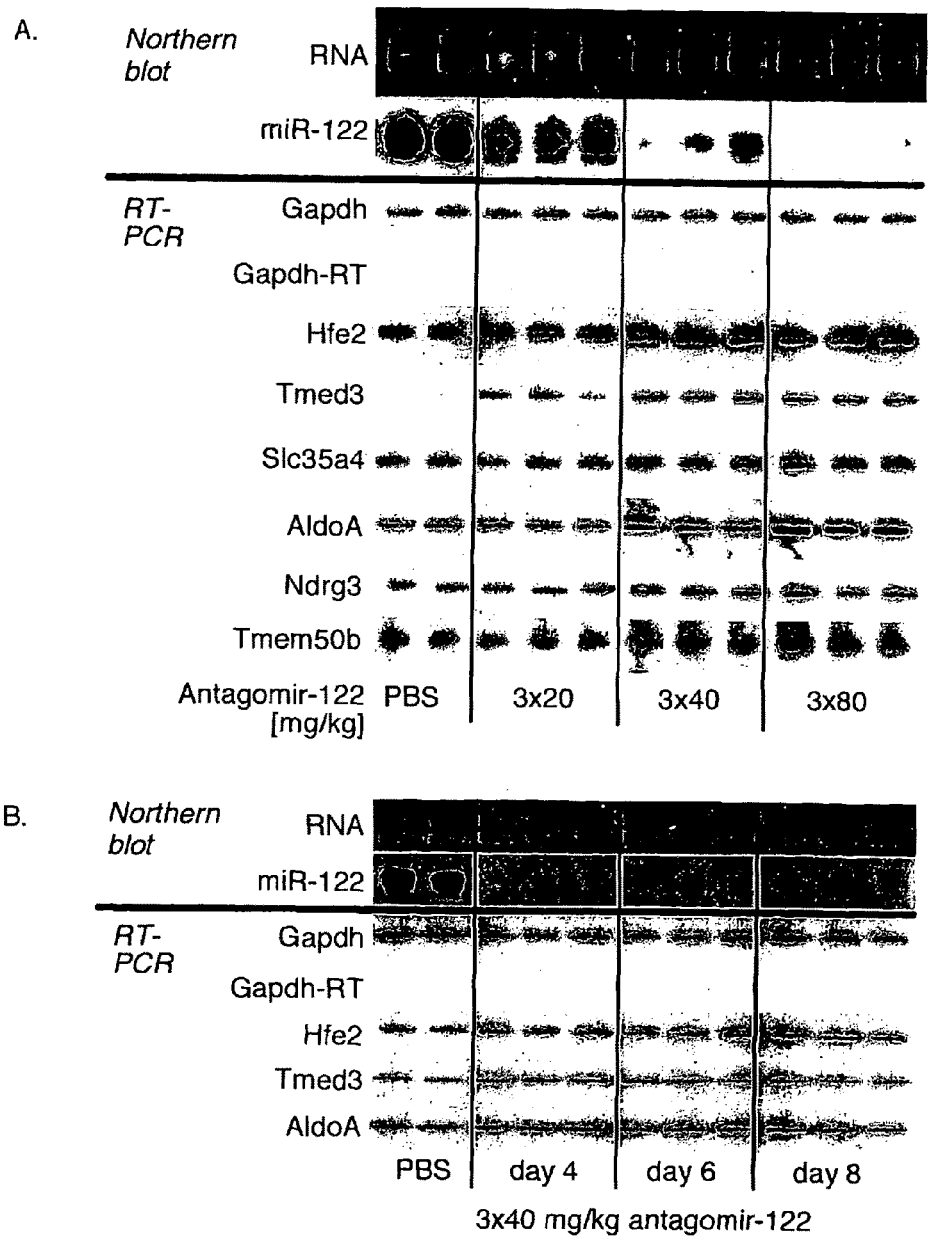
FIG. 18, comprising

To investigate the optimal dose- and time-dependency of antagomir-122, miR-122 levels as well as mRNA levels of endogenous miR-122 targets were analyized. Northern blots show that optimal reduction of miR-122 levels is achieved at antagomir concentrations between 3×40 and 3×80 mg/kg bw (FIG. 18A). The effect of 3×40 mg/kg on miR-122 levels is stable for at least 8 days (=5 days after the last injection) (FIG. 18B). The expression of miR-122 targets correlated with the reduction of miR-122 levels in Northern blots and showed highest upregulation at antagomir concentrations between 3×40 and 3×80 mg/kg bw (FIG. 18A). All targets analyzed showed stable upregulation for at least 5 days after the last injection (FIG. 18A). The results presented herein demonstrate that robust and lasting upregulation of miR-122 targets is achieved at antagomir concentration between 3×40 and 3×80 mg/kg bw as early as 24 hours after the last injection.

Mismatch Discrimination of Antagomirs

Figure 19:
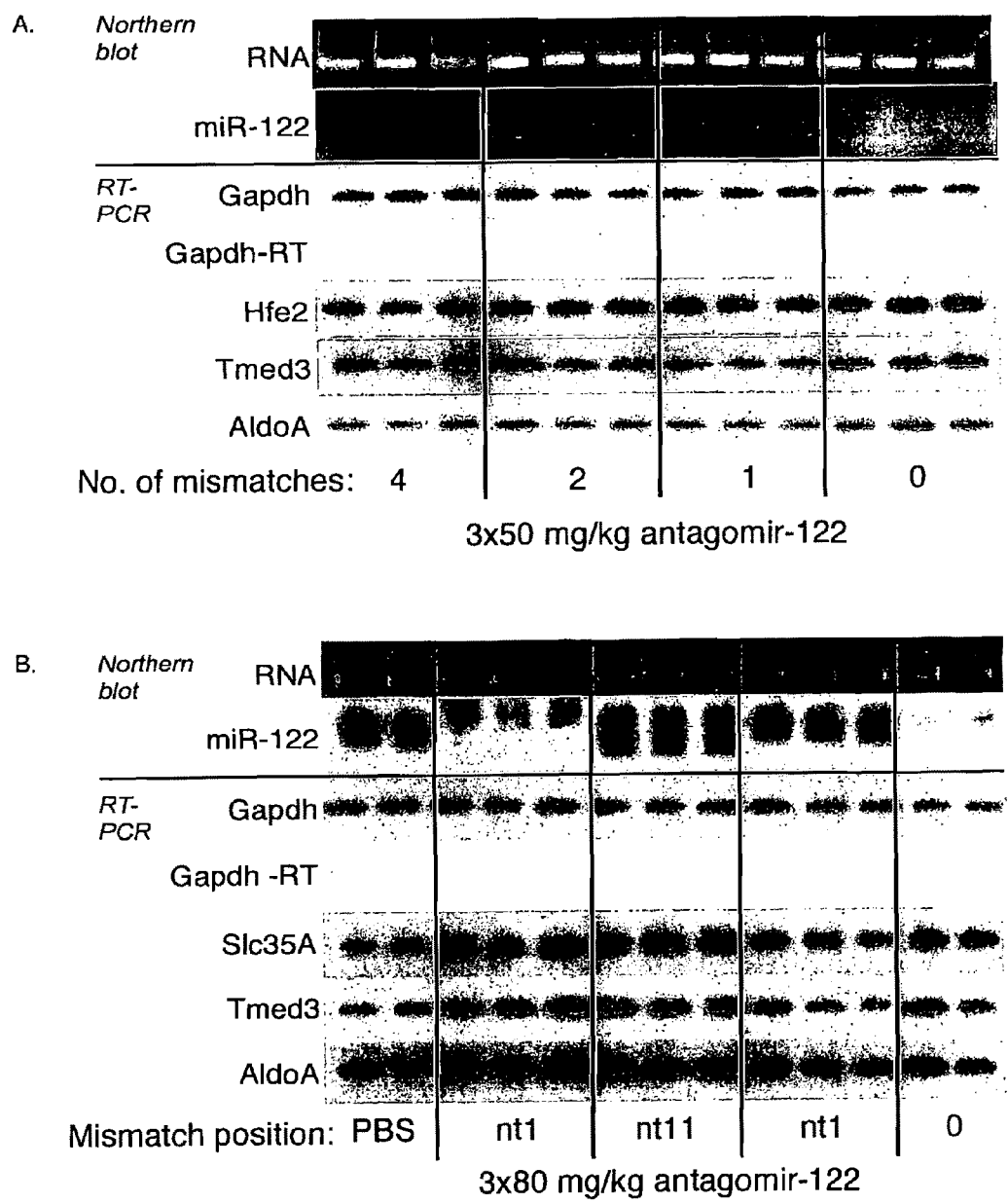
FIG. 19, comprising

The following set of experiments were conducted to test the impact of different mismatch numbers in the antagomir sequence on miR-122 levels and miR-122 targets. Four mismatches, two mismatches or a single mismatch at position 19 was sufficient to prevent downregulation of miR-122 and upregulation of three different miR-122 targets (AldoA, Tmed3 and Hfe2) as measured by RT-PCR (FIG. 19A). However, it was observed that single nucleotide mismatches at two different positions (nt1 or nt11) did not prevent downregulation of miR-122 levels or target regulation (FIG. 4B). Without wishing to be bound by any particular theory, these data demonstrate that antagomirs can exhibit high sequence specificity. However, discrimination at the single nucleotide level is position-dependent and testing for each microRNA sequence that is being targeted may be necessary. However, once armed with the present invention, such testing is well within the skill of the artisan trained in the field.

Regulation of miR-122 Targets by Stabilized Duplexes of miR-122/antagomir-122

The next series of experiments were designed to analyze the ability of antagomirs to induce degradation of preformed duplexes in order to address whether antagomir-mediated miRNA silencing involves degradation of the miRNA. Duplexes of antagomir-122 and a synthetic miR-122 that harbors modifications to protect against different RNAse activities were synthesized. MiR-122 was either protected at the outside ("out") with a phosphorothioate modification to protect against exonucleases or at two consecutive internal positions (nt13 and nt14 of miR-122; "in") using 2'-O-methyl sugar modification (FIG. 20A) to protect against endonuclease activity. Injection of both types of duplexes led to the appearance of degradation products of the synthetic miR-122 (FIG. 20B). These degradation products did not appear when the duplexes were directly analyzed on the polyacrylamide gels or after they had been subjected to the RNA isolation protocol (FIG. 20B, "spiked control"). Furthermore, the spiked control data demonstrate that the synthetic miRNA was not lost during the isolation procedure. These data establish that both types of stabilized miR-122 that were bound to the antagomir-122 had been degraded. Accordingly, both types of protected duplexes upregulated three different miR-122 targets (FIG. 20B). Without wishing to be bound by any particular theory, it is believed that antagomir-mediated-silencing of miRNAs involves target degradation. However, this process does not depend on exonuclease activity and differs from the RNAi pathway.

Cellular Localization of Antagomirs

Figure 21:
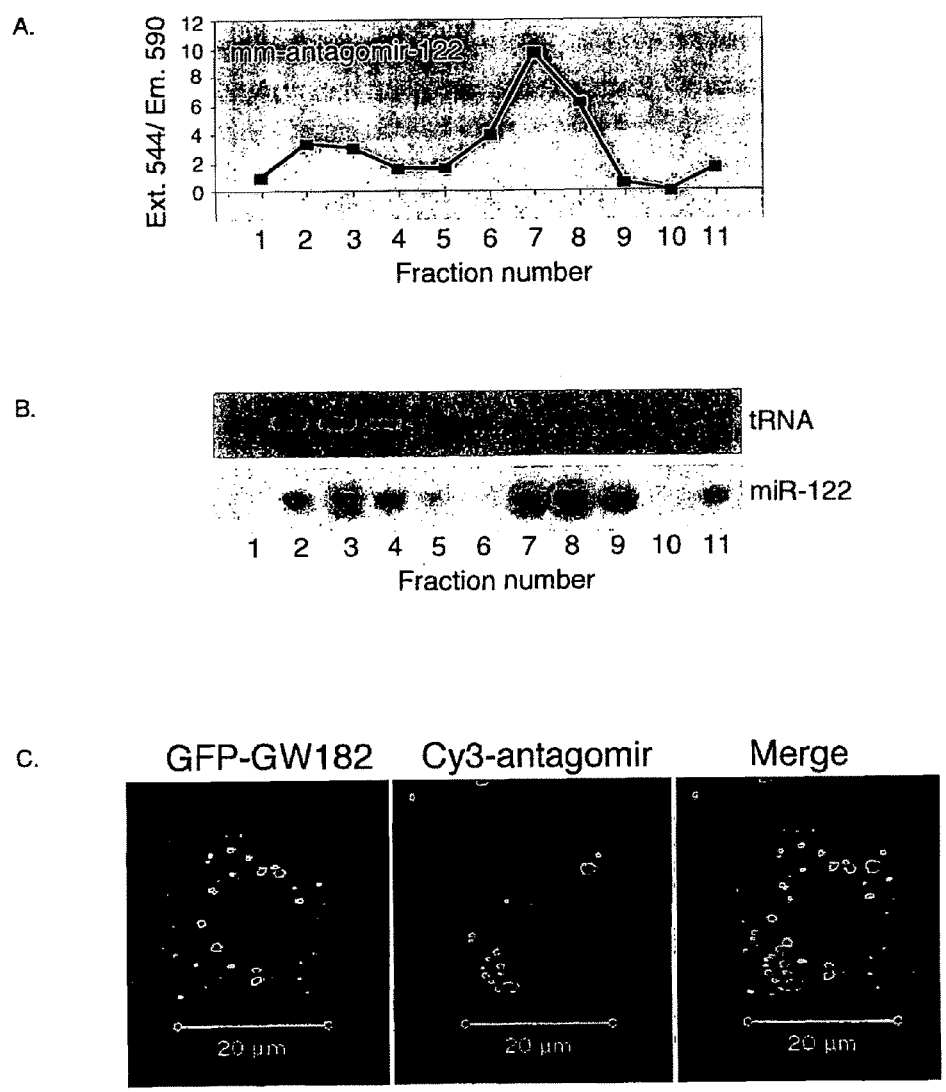
FIG. 21, comprising

To localize antagomirs and miRNA in subcellular compartments, 5'-Q570-labeled antagomir-122 or Q570-labeled mm-antagomir-122 was used. It was observed that Q570-labeling did not impair antagomir-122 function, although silencing efficiency was slightly decreased. Liver homogenates from mice that had been treated with Q570-mm-antagomir-122 were fractionated by ultracentrifugation on sucrose gradients. Northern blot analysis of various fractions showed a single peak of tRNA in fraction 2 (FIG. 21A). In contrast, miR-122 and mm-antagomir-122 localized both to two peaks, fraction ⅔ and fraction ⅞ (FIG. 21).

The next set of experiments were designed to investigate whether co-localization of antagomirs and miRNAs involves the P-body compartment. In order to visualize P-bodies in mouse liver in vivo, a GFP-expressing construct (GFP-GW182) that has previously been demonstrated to act as a marker for the P-body compartment was used (10). GFP- GW182 was overexpressed in liver using high-pressure high-volume tail vein injections. GFP- and Q570-fluorescence was analyzed using laser-scanning microscopy. It was observed that Q570-labeled antagomirs were exclusively localized in the cytosol and were distinct from P-bodies (FIG. 21C). There was no observable overlap between these two compartments. Without wishing to be bound by any particular theory, it is believed that antagomirs and miRNA interact in a cytoplasmic compartment upstream of P-bodies.

Intracerebral Application of Antagomirs

Figure 22:
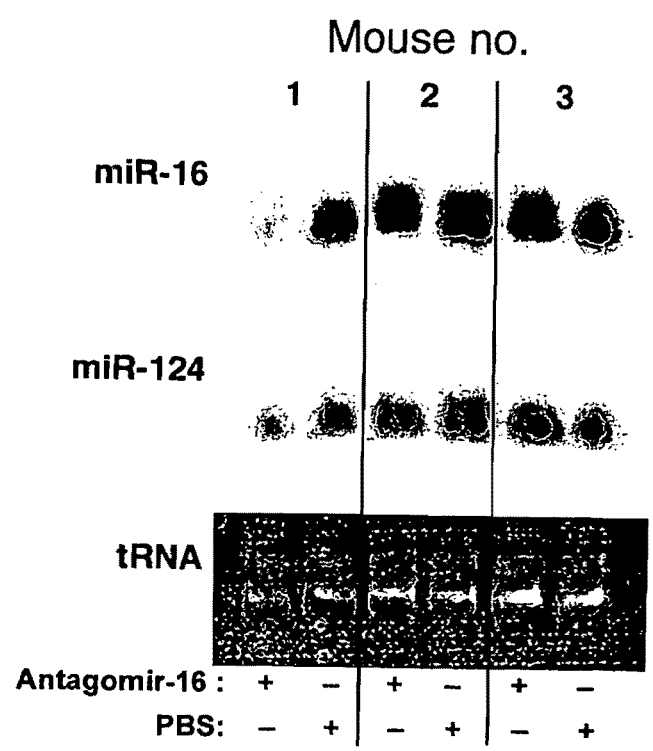
FIG. 22 is a chart depicting Northern blots of miR-16 and miR-124 from total RNA isolated from mouse cerebral cortex that had been injected with antagomir-16 or PBS into the right and left cerebral hemispheres, respectively.

It has been disclosed elsewhere herein that systemic injections of antagomir-16 into tail veins of mice did not influence the steady-state levels of miR-16 in the brain even though miR-16 is ubiquitously expressed in neurons. The following experiments were designed to determine whether antagomir-16 can decrease miRNA levels in the brain when injected directly into the cortex of anesthetized mice. PBS-injections into the contra-lateral side of the same animal served as a control. A single injection of about 0.8 μg of antagomir led to an observable decrease in miR-16 expression at 3 days after the injection (FIG. 22). These results demonstrate that direct application of antagomirs can efficiently target miRNAs in tissues that cannot be reached through tail vein injections.

Example 11

Specificity, Duplex Degradation and Subcellular Localization of Antagomirs

The results presented herein characterize the inhibition of miRNAs with antagomirs in vivo and their therapeutic use. Our study provides a unique platform since its major read-out is based on the dose-and time-dependent regulation of several endogenous and validated targets of miR-122.

Specificity of drug-like oligonucleotides is important to minimize off-target effects and to discriminate between related miRNAs that sometimes differ by only a single nucleotide. In line with this, antagomir chemistry enables discrimination of a single nucleotide. This effect depends on the position of the mismatch within the antagomir sequence. It has been observed that nucleotide exchanges at the very 5'-end of the antagomir or in the center did not prevent downregulation of miR-122 levels in Northern blots and upregulation of miR-122 targets. Without wishing to be bound by any particular theory, it appears that asymmetry of a single nucleotide mismatch may therefore be more detrimental for targeting miRNAs than symmetric changes. These data are important for the design of antagomirs that target specific members of miRNA families or when off-target effects are being considered.

The experiments presented herein were designed to address whether antagomir-mediated silencing of miRNA involves a RNA-induced silencing complex (RISC)-dependent cleavage mechanism. In the RNAi pathway, the siRNA duplex of passenger strand and guide strand is integrated into the RISC complex and the argonaute-2 (Ago2) protein subsequently cleaves the passenger strand across from the guide strand's phosphate bond between position 10 and 11 (Rand, et al., 2005 *Cell,* 123:621-9, and Matranga, et al., 2005 *Cell* 123:607-20). This cleavage was inhibited by a single 2'-O-methylation of the passenger strand corresponding to nucleotide 11 of the guide strand (Rand, et al., 2005 *Cell,* 123:621-9). It is believed that, antagomirs could cleave miRNAs within RISC with the antagomir acting as the guide strand.

miRNA/antagomir-duplexes were injected into mice that harbored a 2'-O-methyl endonuclease protection of the microRNA corresponding to nucleotide 10 and 11 of the antagomir. However, endonuclease protection between nucleotides 10 and 11 did not prevent the degradation of the miRNA as demonstrated by abundant miRNA fragments in Northern analysis, nor did it prevent the upregulation of miR-122 targets. Thus Ago2-mediated cleavage is unlikely to mediate this process. Similar results were obtained when the miRNA was protected at the outside positions using phosphorothioates, indicating that the miRNA targeting does not dependent on exonuclease activity either. However, the fact that miRNA/antagomir-duplexes regulated miRNA targets suggests antagomir recycling. The appearance of miRNA fragments of decreased length also suggests that degradation is involved in this recycling process.

To address the subcellular compartment where interaction of miRNA and antagomir occurs, flurophore labeled antagomirs were engineered. Flurophore labeling of siRNA has previously been used to evaluate cellular uptake of siRNA (Grunweller, et al., 2003 *Oligonucleotides,* 13:345-52, and Lingor, et al., 2005 *Brain* 128:550-8). Q570-labeled antagomirs were cleared from the plasma at a $t_{1/2}$ of approximately 30 minutes, which is considerably faster than the plasma-clearance of cholesterol-conjugated siRNA of about 90 minutes (Soutschek, et al., 2004 *Nature* 432:173-8). A striking overlap of the subcellular localization profiles of antagomirs and miRNAs by sucrose gradient ultracentrifugation analysis of liver homogenates indicates that they may share subcellular compartments. It was observed that antagomir localization within hepatocytes was strictly limited to the cytosol. Without wishing to be bound by any particular theory, it is believed that antagmir localization to the cytosol explains why antagomirs did not influence steady-state levels of the nuclear precursors of miRNAs (Krutzfeldt, et al., 2005 *Nature* 438:685-9).

Experiments were also designed to address whether antagomirs could localize to P-bodies, since this compartment has been linked to the miRNA pathway. P-bodies are enriched in Ago2 as well as mRNA that is targeted by miRNAs. There was no observation of any co-localization of antagomirs with P-bodies. Therefore, it is believed that the interaction of antagomirs with miRNAs occurs upstream of this compartment.

Different types of chemical modifications on antagomirs were also assessed. Phosphorothioate modifications provide protection against RNase activity and their lipophilicity contributes to enhanced tissue uptake. Phosphorothioates also decrease the melting temperature of RNA duplexes (Davis, et al., 2006 *Nucleic Acids Res* 34:2294-304) and have been shown to be general inhibitors of cellular RNAse activity (Crooke, et al., 2000 *J Pharmacol Exp Ther* 292:140-9). The results presented herein indicate a critical balance of the number of phosphorothioates within the antagomir chemistry. While a significant number of phosphorothioates increases efficiency, complete phosphorothioate modification decreased efficiency. For example, it was demonstrated that antagomirs require >19 nucleotides length for optimal function.

Results presented herein also demonstrate that antagomirs can efficiently decrease miR-16 levels in mouse brain when injected locally. Systemic infusions of antagomir-16 do not result in an observable change in the brain levels of miR-16. This is because it is believed that antagomir-16 does not have the ability to cross the blood-brain barrier. Local injections of small amounts of antagomir-16 efficiently reduced expression of this miR-16 in the cortex. This inhibition was specific since the expression of other miRNAs was not affected and no alteration in miR-16 levels were measured in the contra-lateral hemisphere that was injected with PBS. These results suggest that miRNA-inhibitors could facilitate the elucidation of miRNA function in the CNS.

For further characterization of antagomirs, expression levels of endogenous miR-122 targets were used as a read-out. The results presented herein demonstrate that antagomirs can be used in a time and dose-dependent fashion to study miRNA targets. Furthermore, the characterization of the antagomirs with regard to specificity, functional minimal length requirements and effectiveness in the CNS following direct application further support the use of miRNA inhibitors in a clinical setting as a therapeutic composition.

Example 12

Strategy to Study miRNA Function In Vivo

The following experiments are designed to study miRNA function in vivo. Typically, gene expression profiling, bioinformatics analysis, metabolic profiling, and biochemical target validation is performed. Using methods discussed elsewhere herein, miR-122 was observed to regulate levels of many target genes (FIG. 23). Moreover, miR-122 was observed to regulate the expression of cholesterol biosynthesis genes (FIG. 24). Based on the genes observed to be regulated by miR-122, metabolic parameters of antagomir-122 treated mice were evaluated. The results demonstrated that mice treated with antagomir-122 exhibited a decreased levels of at least cholesterol as compared with mice treated with mm-antagomir (FIG. 25). The results presented herein characterize the inhibition of miRNAs with antagomirs in vivo and their therapeutic use with respect to cholesterol levels.

OTHER EMBODIMENTS

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The disclosures of each and every patent, patent application, and publication cited herein are hereby incorporated herein by reference in their entirety.

What is claimed is:

1. A method of reducing plasma cholesterol levels in a mammal, the method comprising administering an antagomir to the mammal, wherein the antagomir is 15 to 25 nucleotides in length and has no more than two mismatches to the sequence of miR-122 (SEQ ID NO: 1), further wherein said antagomir comprises a non-nucleotide moiety at the 3'-end, a 2'-modification at each nucleotide, a phosphorothioate at the first and second internucleotide linkages at the 5' end of the nucleotide sequence, a phosphorothioate at each of the first three internucleotide linkages at the 3' end of the nucleotide sequence, and a phosphorothioate linkage between the 3' terminal nucleotide and the non-nucleotide moiety, and wherein the remaining internucleotide linkages are phosphodiester.

2. The method of claim 1, wherein the non-nucleotide moiety is a cholesterol moiety.

3. The method of claim 1, wherein the 2'-modified nucleotide comprises a modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

4. The method of claim 3, wherein the 2'-modified nucleotide comprises a 2'-O-methyl.

5. The method of claim 1, wherein the antagomir has no more than 1 mismatches to the target sequence.

6. The method of claim 1, wherein the antagomir has no mismatches to the target sequence.

7. The method of claim 1, wherein the antagomir is 18 to 25 nucleotides in length.

8. The method of claim 1, wherein the antagomir is present in a pharmaceutical composition.

9. The method of claim 1, wherein the administering comprises parenteral administration.

10. The method of claim 1, wherein the administering comprises intravenous administration.

11. The method of claim 1, further comprising reducing HMG-CoA reductase activity.

12. The method of claim 1, wherein the antagomir has the sequence of SEQ ID NO: 5, and the non-nucleotide moiety is a cholesterol moiety.

* * * * *